(12) United States Patent
Rodgers et al.

(10) Patent No.: US 8,632,989 B1
(45) Date of Patent: Jan. 21, 2014

(54) MUTANT INSULIN DEGRADING ENZYME AND METHODS OF USE

(75) Inventors: David W. Rodgers, Lexington, KY (US); Louis B. Hersh, Lexington, KY (US); Nicholas Noinaj, Bethesda, MD (US); Eun Suk Song, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 13/484,573

(22) Filed: May 31, 2012

Related U.S. Application Data

(60) Provisional application No. 61/491,481, filed on May 31, 2011, provisional application No. 61/494,248, filed on Jun. 7, 2011.

(51) Int. Cl.
*C12N 9/64* (2006.01)

(52) U.S. Cl.
USPC .......................................................... 435/7.72

(58) Field of Classification Search
USPC ................................................. 435/7.6, 7.72
See application file for complete search history.

*Primary Examiner* — Tekchand Saidha
*Assistant Examiner* — Rama P Ramanujam
(74) *Attorney, Agent, or Firm* — McDermott, Will & Emery LLP

(57) ABSTRACT

In one aspect, the present invention provides an isolated mutant insulin degrading enzyme (IDE) having an amino acid sequence that is at least 90% identical to SEQ ID NO:1 over its entire length and comprises at least one amino acid substitution at any of amino acid residues 332, 339, 341, 359, 360, 361, 374, 429, 609, 898, 899 or 901 of the sequence. The mutant IDE has a differential activity relative to that of wild-type IDE. Also provided is a polynucleotide encoding the polypeptide of the invention.

19 Claims, 19 Drawing Sheets

SEQ ID NO:1

```
  1 MRNGLVWLLH PALPSTLHSI LGARPPPVKR LCGFPKQIYS TMNNPAIQRI EDHIVKSPED
 61 KREYRGLELA NGIKVLLISD PTTDKSSAAL DVHIGSLSDP PNIPGLSHFC EHMLFLGTKK
121 YPKENEYSQF LSEHAGSSNA FTSGEHTNYY FDVSHEHLEG ALDRFAQFFL CPLFDASCKD
181 REVNAVDSEH EKNVMNDAWR LFQLEKATGN PKHPFSKFGT GNKYTLETRP NQEGIDVREE
241 LLKFHSTYYS SNLMAICVLG RESLDDLTNL VVKLFSEVEN KNVPLPEFPE HPFQEEHLKQ
301 LYKIVPIKDI RNLYVTFPIP DLQQYYKSNP GHYLGHLIGH EGPGSLLSEL KSKGWVNTLV
361 GGQKEGARGF MFFIINVDLT EEGLLHVEDI ILHMFQYIQK LRAEGPQEWV FQECKDLNAV
421 AFRFKDKERP RGYTSKIAGK LHYYPLNGVL TAEYLLEEFR PDLIDMVLDK LRPENVRVAI
481 VSKSFEGKTD RTEQWYGTQY KQEAIPEDVI QKWQNADLNG KFKLPTKNEF IPTNFEILAL
541 EKDATPYPAL IKDTAMSKLW FKQDDKFFLP KACLNFEFFS PFAYVDPLHC NMAYLYLELL
601 KDSLNEYAYA AELAGLSYDL QNTIYGMYLS VKGYNDKQPI LLKKITEKMA TFEIDKKRFE
661 IIKEAYMRSL NNFRAEQPHQ HAMYYLRLLM TEVAWTKDEL KEALDDVTLP RLKAFIPQLL
721 SRLHIEALLH GNITKQAALG VMQMVEDTLI EHAHTKPLLP SQLVRYREVQ LPDRGWFVYQ
781 RRNEVHNNCG IEIYYQTDMQ STSENMFLEL FCQIISEPCF NTLRTKEQLG YIVFSGPRRA
841 NGIQGLRFII QSEKPPHYLE SRVEAFLITM EKAIEDMTEE AFQKHIQALA IRRLDKPKKL
901 SAECAKYWGE IISQQYNYDR DNIEVAYLKT LSKDDIIKFY KEMLAVDAPR RHKVSVHVLA
961 REMDSCPVVG EFPSQNDINL SEAPPLPQPE VIHNMTEFKR GLPLFPLVKP HINFMAAKL
```

Figure 12

SEQ ID NO:2

```
  1 MRYRLAWLLH PALPSTFRSV LGARLPPPER LCGFQKKTYS KMNNPAIKRI GNHITKSPED
 61 KREYRGLELA NGIKVLLISD PTTDKSSAAL DVHIGSLSDP PNIAGLSHFC EHMLFLGTKK
121 YPKENEYSQF LSEHAGSSNA FTSGEHTNYY FDVSHEHLEG ALDRFAQFFL CPLFDESCKD
181 REVNAVDSEH EKNVMNDAWR LFQLEKATGN PKHPFSKFGT GNKYTLETRP NQEGIDVRQE
241 LLKFHSAYYS SNLMAVCVLG RESLDDLTNL VVKLFSEVEN KNVPLPEFPE HPFQEEHLKQ
301 LYKIVPIKDI RNLYVTFPIP DLQKYYKSNP GHYLGHLIGH EGPGSLLSEL KSKGWVNTLV
361 GGQKEGARGF MFFIINVDLT EEGLLHVEDI ILHMFQYIQK LRAEGPQEWV FQECKDLNAV
421 AFRFKDKERP RGYTSKIAGI LHYYPLEEVL TAEYLLEEFR PDLIEMVLDK LRPENVRVAI
481 VSKSFEGKTD RTEEWYGTQY KQEAIPDEVI KKWQNADLNG KFKLPTKNEF IPTNFEILPL
541 EKEATPYPAL IKDTAMSKLW FKQDDKFFLP KACLNFEFFS PFAYVDPLHC NMAYLYLELL
601 KDSLNEYAYA AELAGLSYDL QNTIYGMYLS VKGYNDKQPI LLKKIIEKMA TFEIDEKRFE
661 IIKEAYMRSL NNFRAEQPHQ HAMYYLRLLM TEVAWTKDEL KEALDDVTLP RLKAFIPQLL
721 SRLHIEALLH GNITKQAALG IMQMVEDTLI EHAHTKPLLP SQLVRYREVQ LPDRGWFVYQ
781 QRNEVHNNCG IEIYYQTDMQ STSENMFLEL FCQIISEPCF NTLRTKEQLG YIVFSGPRRA
841 NGIQGLRFII QSEKPPHYLE SRVEAFLITM EKSIEDMTEE AFQKHIQALA IRRLDKPKKL
901 SAECAKYWGE IISQQYNFDR DNTEVAYLKT LTKEDIIKFY KEMLAVDAPR RHKVSVHVLA
961 REMDSCPVVG EFPCQNDINL SQAPALPQPE VIQNMTEFKR GLPLFPLVKP HINFMAAKL
```

Figure 13

SEQUENCE LISTING

```
<160> NUMBER OF SEQ ID NOS: 18

<210> SEQ ID NO 1
<211> LENGTH: 1019
<212> TYPE: PRT
<213> ORGANISM: Rattus norvegicus
<220> FEATURE:
<221> NAME/KEY: MISC_FEATURE
<223> OTHER INFORMATION: wild-type Insulin Degrading Enzyme (IDE) from
      rat

<400> SEQUENCE: 1

Met Arg Asn Gly Leu Val Trp Leu Leu His Pro Ala Leu Pro Ser Thr
1               5                   10                  15

Leu His Ser Ile Leu Gly Ala Arg Pro Pro Val Lys Arg Leu Cys
            20                  25                  30

Gly Phe Pro Lys Gln Ile Tyr Ser Thr Met Asn Asn Pro Ala Ile Gln
        35                  40                  45

Arg Ile Glu Asp His Ile Val Lys Ser Pro Glu Asp Lys Arg Glu Tyr
    50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95

Leu Ser Asp Pro Pro Asn Ile Pro Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Ala
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
        195                 200                 205

Gly Asn Pro Lys His Pro Phe Ser Lys Phe Gly Thr Gly Asn Lys Tyr
    210                 215                 220

Thr Leu Glu Thr Arg Pro Asn Gln Glu Gly Ile Asp Val Arg Glu Glu
225                 230                 235                 240

Leu Leu Lys Phe His Ser Thr Tyr Tyr Ser Ser Asn Leu Met Ala Ile
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
        275                 280                 285

Pro Glu His Pro Phe Gln Glu Glu His Leu Lys Gln Leu Tyr Lys Ile
    290                 295                 300

Val Pro Ile Lys Asp Ile Arg Asn Leu Tyr Val Thr Phe Pro Ile Pro
305                 310                 315                 320
```

```
Asp Leu Gln Gln Tyr Tyr Lys Ser Asn Pro Gly His Tyr Leu Gly His
                325                 330                 335

Leu Ile Gly His Glu Gly Pro Gly Ser Leu Leu Ser Glu Leu Lys Ser
                340                 345                 350

Lys Gly Trp Val Asn Thr Leu Val Gly Gly Gln Lys Glu Gly Ala Arg
                355                 360                 365

Gly Phe Met Phe Phe Ile Ile Asn Val Asp Leu Thr Glu Glu Gly Leu
                370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
                420                 425                 430

Tyr Thr Ser Lys Ile Ala Gly Lys Leu His Tyr Tyr Pro Leu Asn Gly
                435                 440                 445

Val Leu Thr Ala Glu Tyr Leu Leu Glu Glu Phe Arg Pro Asp Leu Ile
                450                 455                 460

Asp Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Gln Trp Tyr
                485                 490                 495

Gly Thr Gln Tyr Lys Gln Glu Ala Ile Pro Glu Asp Val Ile Gln Lys
                500                 505                 510

Trp Gln Asn Ala Asp Leu Asn Gly Lys Phe Lys Leu Pro Thr Lys Asn
                515                 520                 525

Glu Phe Ile Pro Thr Asn Phe Glu Ile Leu Ala Leu Glu Lys Asp Ala
                530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Phe Leu Pro Lys Ala Cys Leu Asn Phe
                565                 570                 575

Glu Phe Phe Ser Pro Phe Ala Tyr Val Asp Pro Leu His Cys Asn Met
                580                 585                 590

Ala Tyr Leu Tyr Leu Glu Leu Leu Lys Asp Ser Leu Asn Glu Tyr Ala
                595                 600                 605

Tyr Ala Ala Glu Leu Ala Gly Leu Ser Tyr Asp Leu Gln Asn Thr Ile
                610                 615                 620

Tyr Gly Met Tyr Leu Ser Val Lys Gly Tyr Asn Asp Lys Gln Pro Ile
625                 630                 635                 640

Leu Leu Lys Lys Ile Thr Glu Lys Met Ala Thr Phe Glu Ile Asp Lys
                645                 650                 655

Lys Arg Phe Glu Ile Ile Lys Glu Ala Tyr Met Arg Ser Leu Asn Asn
                660                 665                 670

Phe Arg Ala Glu Gln Pro His Gln His Ala Met Tyr Tyr Leu Arg Leu
                675                 680                 685

Leu Met Thr Glu Val Ala Trp Thr Lys Asp Glu Leu Lys Glu Ala Leu
                690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                725                 730                 735

Ala Ala Leu Gly Val Met Gln Met Val Glu Asp Thr Leu Ile Glu His
                740                 745                 750
```

-continued

```
Ala His Thr Lys Pro Leu Leu Pro Ser Gln Leu Val Arg Tyr Arg Glu
        755                 760                 765

Val Gln Leu Pro Asp Arg Gly Trp Phe Val Tyr Gln Arg Arg Asn Glu
    770                 775                 780

Val His Asn Asn Cys Gly Ile Glu Ile Tyr Tyr Gln Thr Asp Met Gln
785                 790                 795                 800

Ser Thr Ser Glu Asn Met Phe Leu Glu Leu Phe Cys Gln Ile Ile Ser
            805                 810                 815

Glu Pro Cys Phe Asn Thr Leu Arg Thr Lys Glu Gln Leu Gly Tyr Ile
                820                 825                 830

Val Phe Ser Gly Pro Arg Arg Ala Asn Gly Ile Gln Gly Leu Arg Phe
            835                 840                 845

Ile Ile Gln Ser Glu Lys Pro Pro His Tyr Leu Glu Ser Arg Val Glu
        850                 855                 860

Ala Phe Leu Ile Thr Met Glu Lys Ala Ile Glu Asp Met Thr Glu Glu
865                 870                 875                 880

Ala Phe Gln Lys His Ile Gln Ala Leu Ala Ile Arg Arg Leu Asp Lys
                885                 890                 895

Pro Lys Lys Leu Ser Ala Glu Cys Ala Lys Tyr Trp Gly Glu Ile Ile
                900                 905                 910

Ser Gln Gln Tyr Asn Tyr Asp Arg Asp Asn Ile Glu Val Ala Tyr Leu
            915                 920                 925

Lys Thr Leu Ser Lys Asp Asp Ile Ile Lys Phe Tyr Lys Glu Met Leu
    930                 935                 940

Ala Val Asp Ala Pro Arg Arg His Lys Val Ser Val His Val Leu Ala
945                 950                 955                 960

Arg Glu Met Asp Ser Cys Pro Val Val Gly Glu Phe Pro Ser Gln Asn
                965                 970                 975

Asp Ile Asn Leu Ser Glu Ala Pro Pro Leu Pro Gln Pro Glu Val Ile
            980                 985                 990

His Asn Met Thr Glu Phe Lys Arg  Gly Leu Pro Leu Phe  Pro Leu Val
        995                 1000                1005

Lys Pro  His Ile Asn Phe Met  Ala Ala Lys Leu
   1010                 1015
```

<210> SEQ ID NO 2
<211> LENGTH: 1019
<212> TYPE: PRT
<213> ORGANISM: Rattus norvegicus
<220> FEATURE:
<221> NAME/KEY: MISC_FEATURE
<223> OTHER INFORMATION: wild-type Insulin Degrading Enzyme (IDE) from rat

<400> SEQUENCE: 2

```
Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Glu Arg Leu Cys
            20                  25                  30

Gly Phe Gln Lys Lys Thr Tyr Ser Lys Met Asn Asn Pro Ala Ile Lys
        35                  40                  45

Arg Ile Gly Asn His Ile Thr Lys Ser Pro Glu Asp Lys Arg Glu Tyr
    50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95
```

-continued

```
Leu Ser Asp Pro Pro Asn Ile Ala Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
        195                 200                 205

Gly Asn Pro Lys His Pro Phe Ser Lys Phe Gly Thr Gly Asn Lys Tyr
    210                 215                 220

Thr Leu Glu Thr Arg Pro Asn Gln Glu Gly Ile Asp Val Arg Gln Glu
225                 230                 235                 240

Leu Leu Lys Phe His Ser Ala Tyr Tyr Ser Ser Asn Leu Met Ala Val
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
        275                 280                 285

Pro Glu His Pro Phe Gln Glu Glu His Leu Lys Gln Leu Tyr Lys Ile
    290                 295                 300

Val Pro Ile Lys Asp Ile Arg Asn Leu Tyr Val Thr Phe Pro Ile Pro
305                 310                 315                 320

Asp Leu Gln Lys Tyr Tyr Lys Ser Asn Pro Gly His Tyr Leu Gly His
                325                 330                 335

Leu Ile Gly His Glu Gly Pro Gly Ser Leu Leu Ser Glu Leu Lys Ser
            340                 345                 350

Lys Gly Trp Val Asn Thr Leu Val Gly Gly Gln Lys Glu Gly Ala Arg
        355                 360                 365

Gly Phe Met Phe Phe Ile Ile Asn Val Asp Leu Thr Glu Glu Gly Leu
    370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
            420                 425                 430

Tyr Thr Ser Lys Ile Ala Gly Ile Leu His Tyr Tyr Pro Leu Glu Glu
        435                 440                 445

Val Leu Thr Ala Glu Tyr Leu Leu Glu Glu Phe Arg Pro Asp Leu Ile
    450                 455                 460

Glu Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Glu Trp Tyr
                485                 490                 495

Gly Thr Gln Tyr Lys Gln Glu Ala Ile Pro Asp Glu Val Ile Lys Lys
            500                 505                 510

Trp Gln Asn Ala Asp Leu Asn Gly Lys Phe Lys Leu Pro Thr Lys Asn
        515                 520                 525
```

```
Glu Phe Ile Pro Thr Asn Phe Glu Ile Leu Pro Leu Glu Lys Glu Ala
530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Phe Leu Pro Lys Ala Cys Leu Asn Phe
                565                 570                 575

Glu Phe Phe Ser Pro Phe Ala Tyr Val Asp Pro Leu His Cys Asn Met
            580                 585                 590

Ala Tyr Leu Tyr Leu Glu Leu Leu Lys Asp Ser Leu Asn Glu Tyr Ala
        595                 600                 605

Tyr Ala Ala Glu Leu Ala Gly Leu Ser Tyr Asp Leu Gln Asn Thr Ile
610                 615                 620

Tyr Gly Met Tyr Leu Ser Val Lys Gly Tyr Asn Asp Lys Gln Pro Ile
625                 630                 635                 640

Leu Leu Lys Lys Ile Ile Glu Lys Met Ala Thr Phe Glu Ile Asp Glu
                645                 650                 655

Lys Arg Phe Glu Ile Ile Lys Glu Ala Tyr Met Arg Ser Leu Asn Asn
                660                 665                 670

Phe Arg Ala Glu Gln Pro His Gln His Ala Met Tyr Tyr Leu Arg Leu
            675                 680                 685

Leu Met Thr Glu Val Ala Trp Thr Lys Asp Glu Leu Lys Glu Ala Leu
        690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                725                 730                 735

Ala Ala Leu Gly Ile Met Gln Met Val Glu Asp Thr Leu Ile Glu His
            740                 745                 750

Ala His Thr Lys Pro Leu Leu Pro Ser Gln Leu Val Arg Tyr Arg Glu
        755                 760                 765

Val Gln Leu Pro Asp Arg Gly Trp Phe Val Tyr Gln Gln Arg Asn Glu
770                 775                 780

Val His Asn Asn Cys Gly Ile Glu Ile Tyr Tyr Gln Thr Asp Met Gln
785                 790                 795                 800

Ser Thr Ser Glu Asn Met Phe Leu Glu Leu Phe Cys Gln Ile Ile Ser
                805                 810                 815

Glu Pro Cys Phe Asn Thr Leu Arg Thr Lys Glu Gln Leu Gly Tyr Ile
            820                 825                 830

Val Phe Ser Gly Pro Arg Arg Ala Asn Gly Ile Gln Gly Leu Arg Phe
        835                 840                 845

Ile Ile Gln Ser Glu Lys Pro Pro His Tyr Leu Glu Ser Arg Val Glu
850                 855                 860

Ala Phe Leu Ile Thr Met Glu Lys Ser Ile Glu Asp Met Thr Glu Glu
865                 870                 875                 880

Ala Phe Gln Lys His Ile Gln Ala Leu Ala Ile Arg Arg Leu Asp Lys
                885                 890                 895

Pro Lys Lys Leu Ser Ala Glu Cys Ala Lys Tyr Trp Gly Glu Ile Ile
            900                 905                 910

Ser Gln Gln Tyr Asn Phe Asp Arg Asp Asn Thr Glu Val Ala Tyr Leu
        915                 920                 925

Lys Thr Leu Thr Lys Glu Asp Ile Ile Lys Phe Tyr Lys Glu Met Leu
930                 935                 940

Ala Val Asp Ala Pro Arg Arg His Lys Val Ser Val His Val Leu Ala
945                 950                 955                 960
```

-continued

```
Arg Glu Met Asp Ser Cys Pro Val Val Gly Glu Phe Pro Cys Gln Asn
            965                 970                 975

Asp Ile Asn Leu Ser Gln Ala Pro Ala Leu Pro Gln Pro Glu Val Ile
        980                 985                 990

Gln Asn Met Thr Glu Phe Lys Arg  Gly Leu Pro Leu Phe  Pro Leu Val
    995                 1000                1005

Lys Pro  His Ile Asn Phe Met  Ala Ala Lys Leu
    1010                1015

<210> SEQ ID NO 3
<211> LENGTH: 9
<212> TYPE: PRT
<213> ORGANISM: Artificial
<220> FEATURE:
<223> OTHER INFORMATION: Chemically synthesized
<220> FEATURE:
<221> NAME/KEY: BINDING
<222> LOCATION: (1)..(1)
<223> OTHER INFORMATION: Amino benzoic acid
<220> FEATURE:
<221> NAME/KEY: BINDING
<222> LOCATION: (9)..(9)
<223> OTHER INFORMATION: N -(2,4-dinitrophenyl)-ethylenediamine]

<400> SEQUENCE: 3

Gly Gly Phe Leu Arg Lys His Gly Gln
1               5

<210> SEQ ID NO 4
<211> LENGTH: 33
<212> TYPE: DNA
<213> ORGANISM: Artificial Sequence
<220> FEATURE:
<223> OTHER INFORMATION: Forward Primer

<400> SEQUENCE: 4
cgactcgaca aaccagcgaa actctctgca gag                                33

<210> SEQ ID NO 5
<211> LENGTH: 33
<212> TYPE: DNA
<213> ORGANISM: Artificial Sequence
<220> FEATURE:
<223> OTHER INFORMATION: Reverse Primer

<400> SEQUENCE: 5
ctctgcagag agtttcgctg gtttgtcgag tcg                                33

<210> SEQ ID NO 6
<211> LENGTH: 33
<212> TYPE: DNA
<213> ORGANISM: Artificial Sequence
<220> FEATURE:
<223> OTHER INFORMATION: Forward Primer

<400> SEQUENCE: 6
ctcgacaaac cagcggcact ctctgcagag tgc                                33

<210> SEQ ID NO 7
<211> LENGTH: 33
<212> TYPE: DNA
<213> ORGANISM: Artificial Sequence
<220> FEATURE:
<223> OTHER INFORMATION: Reverse Primer

<400> SEQUENCE: 7
gcactctgca gagagtgccg ctggtttgtc gag                                33
```

```
<210> SEQ ID NO 8
<211> LENGTH: 33
<212> TYPE: DNA
<213> ORGANISM: Artificial Sequence
<220> FEATURE:
<223> OTHER INFORMATION: Forward Primer

<400> SEQUENCE: 8
aaaccagcgg cactcgctgc agagtgcgcg aag                                    33

<210> SEQ ID NO 9
<211> LENGTH: 33
<212> TYPE: DNA
<213> ORGANISM: Artificial Sequence
<220> FEATURE:
<223> OTHER INFORMATION: Reverse Primer

<400> SEQUENCE: 9
cttcgcgcac tctgcagcga gtgccgctgg ttt                                    33

<210> SEQ ID NO 10
<211> LENGTH: 33
<212> TYPE: DNA
<213> ORGANISM: Artificial Sequence
<220> FEATURE:
<223> OTHER INFORMATION: Forward Primer

<400> SEQUENCE: 10
tttaaagata aagagagccc acgaggctac aca                                    33

<210> SEQ ID NO 11
<211> LENGTH: 33
<212> TYPE: DNA
<213> ORGANISM: Artificial Sequence
<220> FEATURE:
<223> OTHER INFORMATION: Reverse Primer

<400> SEQUENCE: 11
tgtgtagcct cgtgggctct ctttatcttt aaa                                    33

<210> SEQ ID NO 12
<211> LENGTH: 33
<212> TYPE: DNA
<213> ORGANISM: Artificial Sequence
<220> FEATURE:
<223> OTHER INFORMATION: Forward Primer

<400> SEQUENCE: 12
ctcaacgact atgcatttgc agcagagcta gca                                    33

<210> SEQ ID NO 13
<211> LENGTH: 33
<212> TYPE: DNA
<213> ORGANISM: Artificial Sequence
<220> FEATURE:
<223> OTHER INFORMATION: Reverse Primer

<400> SEQUENCE: 13
tgctagctgt gctgcaaatg catactcgtt gag                                    33

<210> SEQ ID NO 14
<211> LENGTH: 33
<212> TYPE: DNA
<213> ORGANISM: Artificial Sequence
<220> FEATURE:
<223> OTHER INFORMATION: Forward Primer
```

-continued

```
<400> SEQUENCE: 14
tgggtaaaca ccctgtctgg gggacagaag gaa                                    33

<210> SEQ ID NO 15
<211> LENGTH: 33
<212> TYPE: DNA
<213> ORGANISM: Artificial Sequence
<220> FEATURE:
<223> OTHER INFORMATION: Reverse Primer

<400> SEQUENCE: 15
ttccttctgt cccccagaca gggtgtttac cca                                    33

<210> SEQ ID NO 16
<211> LENGTH: 33
<212> TYPE: DNA
<213> ORGANISM: Artificial Sequence
<220> FEATURE:
<223> OTHER INFORMATION: Forward Primer

<400> SEQUENCE: 16
ggttttatgt tttttccat taatgtggac tta                                     33

<210> SEQ ID NO 17
<211> LENGTH: 33
<212> TYPE: DNA
<213> ORGANISM: Artificial Sequence
<220> FEATURE:
<223> OTHER INFORMATION: Reverse Primer

<400> SEQUENCE: 17
taagtccaca ttaatggaaa aaaacataaa acc                                    33

<210> SEQ ID NO 18
<211> LENGTH: 22
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: acetylation of N-terminal serine

<400> SEQUENCE: 18

Ser Tyr Tyr His His His His His His Asp Tyr Asp Ile Pro Thr Thr
1               5                   10                  15

Glu Asn Leu Tyr Phe Gln
            20
```

MUTANT INSULIN DEGRADING ENZYME AND METHODS OF USE

RELATED APPLICATIONS

This application claims the benefit of U.S. Provisional Application Nos. 61/491,481, filed May 31, 2011; and 61/494,248, filed Jun. 7, 2011. The entire content of each of the above applications is incorporated herein by reference in its entirety as though fully set forth herein.

STATEMENT REGARDING GOVERNMENT RIGHTS

This invention was supported in part by United States Public Health Services grants DA02243, NS38041, DA016176, T32 DA016176 and P20 RR20171. The United States government has certain rights in this invention.

SEQUENCE LISTING

The application contains a Sequence Listing which has been submitted in ASCII format via EFS-Web and is hereby incorporated by reference in its entirety. Said ASCII copy, created on May 15, 2013, is named SEQUENCE_LISTING.txt and is 24,576 bytes in size.

FIELD OF THE INVENTION

The present invention relates to insulin degrading enzyme known as IDE or insulysin; more particularly to a mutant IDE and method of use thereof.

BACKGROUND OF THE INVENTION

Insulin-degrading enzyme (IDE) (EC 3.4.24.56, formerly listed as EC 3.4.22.11) is a zinc metallopeptidase from the M16 family that has been extensively studied due to its role in regulating cellular insulin. More recently, IDE has received considerable attention for its role in degrading amyloid β peptides, and a genetic link between IDE and late onset Alzheimer's disease has been reported. IDE degrades a number of other physiological peptides in vitro, including IGF-1 and IGF-2, glucagon, atrial natriuretic peptide, TGF-α, and γ-endorphin. In addition to its metabolic role in peptide degradation, IDE has been reported to play a role in the inhibition of proteasome function by insulin, to degrade oxidized proteins in peroxisomes, to serve as a receptor accessory factor that enhances androgen and glucocorticoid receptor binding to DNA, and to serve as a receptor for the Varicella-Zoster virus. Thus, IDE has a central role in mammalian physiology, and modulating its function can prove valuable for the treatment of disease states, most notably diabetes and Alzheimer's disease. There is a need in the art for improved understanding of the interaction between IDE and its allosteric regulators to facilitate development of compositions and methods for modulating the IDE activity.

SUMMARY OF THE INVENTION

In one aspect, the present invention relates to an isolated mutant insulin degrading enzyme (IDE) having at least one amino acid substitution at any of amino acid residues 332, 339, 341, 359, 360, 361, 374, 429, 609, 898, 899 or 901 of SEQ ID NO:1 or SEQ ID NO:2. In a related embodiment, the isolated mutant IDE has peptidase activity. In another related embodiment, the mutant IDE has a substantially similar, increased, or decreased peptidase activity relative to peptidase activity of a wild-type IDE set forth in SEQ ID NO: 1 or SEQ ID NO:2. In another related embodiment, the mutant IDE further has a chemical modification that increases stability of the mutant IDE. In another related embodiment, the chemical modification includes addition of a component selected from the group consisting of a polymer and a second polypeptide. In another related embodiment, the polymer is PEG.

In another aspect, the present invention relates to an isolated mutant insulin degrading enzyme (IDE) having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence. In a related embodiment, the isolated mutant IDE has peptidase activity. In another related embodiment, the mutant IDE has a substantially similar, increased, or decreased peptidase activity relative to peptidase activity of a wild-type IDE of SEQ ID NO: 1. In another embodiment, the amino acid sequence is at least 95% identical to SEQ ID NO:1 over its entire length. In another related embodiment, the mutant IDE further has a chemical modification that increases stability of the mutant IDE. In another related embodiment, the chemical modification includes addition of a component selected from the group consisting of a polymer and a second polypeptide. In another related embodiment, the polymer is PEG.

In another aspect, the present invention provides a polynucleotide encoding any of the polypeptides of the invention. In a related embodiment, the polynucleotide encodes a mutant IDE having at least one amino acid substitution at any of amino acid residues 332, 339, 341, 359, 360, 361, 374, 429, 609, 898, 899 or 901 of SEQ ID NO:1 or SEQ ID NO:2, wherein the mutant IDE has peptidase activity. In a related embodiment, the polynucleotide encodes a mutant IDE having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence, wherein the mutant IDE has peptidase activity. In another related embodiment, the polynucleotide sequence encoding the mutant IDE is operably linked to a promoter.

In another aspect, the present invention provides a vector including any of the polynucleotide sequences encoding the IDE mutants of the invention.

In another aspect, the present invention provides a host cell into which has been incorporated the polynucleotide sequence encoding any of the IDE mutants of the invention.

In another aspect, the present invention provides a method of screening agents that modulate the activity of a mutant IDE; said method including the steps of (a) contacting a test agent with the mutant IDE in the presence of an IDE substrate, wherein the mutant IDE comprises an amino acid sequence that is at least 90% identical to SEQ ID NO:1 over its entire length and comprises at least one amino acid substitution at any of amino acid residues 332, 339, 341, 359, 360, 361, 374, 429, 609, 898, 899 or 901 of the sequence; (b) assessing the effect of a test agent on activity of the mutant IDE, wherein activity is measured as effect of the test agent on the affinity of the mutant IDE for the IDE substrate or the test agent, rate of the IDE substrate cleavage, or stability of the mutant IDE, relative to a control lacking the test agent; and (c) selecting any test agent that modulates the affinity of the mutant IDE for the IDE substrate or the test agent, the rate of the IDE substrate cleavage, or the stability of the mutant IDE. In a related embodiment, the test agent is selected from the group consisting of a peptidomimetic, analog of a peptide activators, peptide derivative or analog of Aβ, saccharide, fatty acid, purine, pyrimidine, nucleic acid, derivative or analog thereof, complex organic or simple or complex inorganic molecules, metal-containing compounds, steroids, or steroid analog, fluorogenic peptide or derivative or analog thereof, and any such molecules in combination. In another related embodiment, the activity is assessed by measuring the effect of the test agent on the affinity of the mutant IDE for an IDE substrate. In another related embodiment, the substrate is labeled with a detectable label. In another related embodiment, the substrate is monitored via high performance liquid chromatography.

In another aspect, the present invention provides a method of identifying agents that modulate the activity of a mutant IDE; said method including the steps of (a) contacting a test agent with the mutant IDE in the presence of an IDE substrate, wherein the mutant IDE comprises an amino acid sequence that is at least 90% identical to SEQ ID NO:1 over its entire length and comprises at least one amino acid substitution at any of amino acid residues 332, 339, 341, 359, 360, 361, 374, 429, 609, 898, 899 or 901 of the sequence; (b) assessing the effect of a test agent on activity of the mutant IDE, wherein activity is measured as effect of the test agent on the affinity of the mutant IDE for the IDE substrate or the test agent, rate of the IDE substrate cleavage, or stability of the mutant IDE, relative to a control lacking the test agent; and (c) identifying any test agent that modulates the affinity of the mutant IDE for the IDE substrate or the test agent, the rate of the IDE substrate cleavage, or the stability of the mutant IDE.

It is to be understood that both the foregoing general description and the following detailed description are exemplary and explanatory only and are not restrictive of the invention, as claimed.

BRIEF DESCRIPTION OF THE DRAWINGS

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the invention.

FIG. 12 shows the amino acid sequence of SEQ ID NO:1 corresponding to native/unmodified rat IDE.

FIG. 13 shows the amino acid sequence of SEQ ID NO:2 corresponding to native/unmodified human IDE.

DETAILED DESCRIPTION OF THE INVENTION

Figure 1:
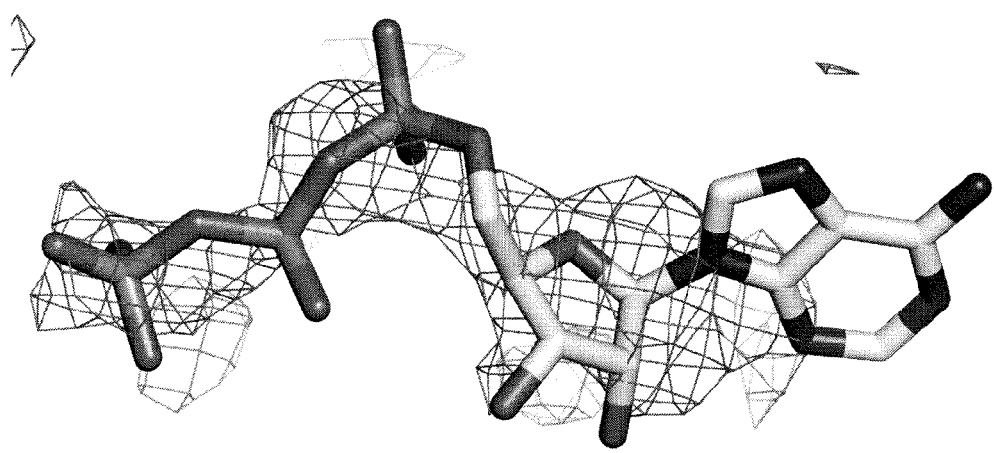
FIG. 1 shows the difference in electron density (Fo-Fc) assigned to bound ATP. The density (displayed with a cutoff of 2.0 the r.m.s. of the map) was phased from the rigidly refined IDE structure, which was used as a molecular replacement object. ATP modeled into the difference density is shown in a stick representation.

Insulin degrading enzyme (IDE, EC 3.4.24.56; also known as insulysin) is a zinc metallopeptidase in the M16 family that has been extensively studied because of its role in cellular insulin degradation and amyloid beta peptide catabolism. The importance of IDE in regulating insulin metabolism became evident from studies of the GK rat model of type II diabetes mellitus where variants of IDE with reduced catalytic activity were found to be associated with elevated insulin levels. In addition, mice with homozygous deletions of IDE show a marked decrease in insulin degradation, while IDE polymorphisms have been associated with type 2 diabetes in humans. Recently, IDE has received considerable attention for its role in the degradation of amyloid beta (Aβ) peptide, and a number of studies have provided evidence for a genetic link between IDE and Alzheimer's disease. IDE can degrade many bioactive peptides of varying size in addition to insulin and the amyloid beta peptide, although its role in regulating the levels other peptides in vivo has not been established.

IDE exists predominantly as a dimer in equilibrium with tetramers and to a lesser extent monomers. It is unique among the enzymes comprising the zinc metallopeptidase M16 family in that it exhibits allosteric kinetic behavior with substrate peptides increasing its activity. In addition, IDE contains a distinct regulatory site first reported by Camberos and coworkers (Camberos M C, Perez A A, Udrisar D P, Wanderley M I, Cresto J C (2001) ATP inhibits insulin-degrading enzyme activity, Exp Biol Med (Maywood) 226: 334-341). This site was shown to be distinct from the active site and to primarily interact with the triphosphate moiety (Song E S, Juliano M A, Juliano L, Fried M G, Wagner S L, et al. (2004) ATP effects on insulin-degrading enzyme are mediated primarily through its triphosphate moiety. J Biol Chem 279: 54216-54220). Binding at this site was shown to increase the rate of hydrolysis of some, but not all, IDE substrates (Song et al., (2004); Yao H, Hersh L B (2006) Characterization of the binding of the fluorescent ATP analog TNP-ATP to insulysin. Arch Biochem Biophys 451: 175-181).

Crystal structures of human IDE (hIDE) complexed with peptides show that the enzyme consists of four structurally related domains that adopt a clamshell-like structure enclosing a large central chamber. Both the liganded and unliganded structures of human IDE have been recently reported (Shen et al., *Nature* 443, 870-874 (2006) and Im et al., *Journal of Biological Chemistry* 282, 25453-25463 (2007)). The tertiary structure resembles a clamshell composed of four structurally similar domains arranged to enclose a large central chamber. Substrates appear trapped in the central chamber, which has a volume of ~43,000 Å$^3$, and it is believed that a hinge-like conformational change is necessary for substrate binding and product release. Although the four domains have the same overall fold, only the N-terminal domain, domain 1, has an intact active site characteristic of zinc metallopeptidases. Substrate binding requires a conformational change that opens the central chamber, making internal binding sites accessible. Substrates bind at the active site in a manner consistent with other zinc metallopeptidases, but larger peptides can also interact with a distal binding site located in a separate domain of the enzyme. The unliganded structure of hIDE was found to be in the same closed conformation first observed in the peptide complex structures, further indicating that the rate-limiting step for catalysis is the conformational switch from the closed to open state.

The present invention is based in part on the discovery of the allosteric site on IDE where ATP or polyanions bind to and modulate the activity of IDE. This allosteric site is represented by four amino acid residues (i.e., Lys898, Lys899, Ser901 and Arg429) in SEQ ID NO:1 or SEQ ID NO:2 or variants thereof. The binding of ATP or polyanion to this allosteric site activates IDE by altering the partitioning between open and closed conformations of the enzyme and is independent of the ATP hydrolysis activity reported for IDE.

The present invention is also based in part on the discovery of an allosteric regulatory site in IDE, which is independent from the enzyme's polyanion allosteric or substrate binding sites. This allosteric regulatory site is located in the distal site of domain 2 in IDE and is represented by eight amino acid residues (i.e., His332, Gly339, Glu341, Leu359, Val360, Gly361, Ile374, Tyr609) in SEQ ID NO:1 or SEQ ID NO:2 or variants thereof. The binding of regulatory agents such as peptides to this site can affect the allosterism of the enzyme and its catalytic activities.

Thus, in one aspect, the present invention relates to mutant or recombinant IDEs having at least one amino acid substitution at any of amino acid residues 332, 339, 341, 359, 360, 361, 374, 429, 609, 898, 899 or 901 of SEQ ID NO:1 or SEQ ID NO:2. The mutant IDE has insulin degrading activity. In a related embodiment, the isolated mutant IDE has peptidase activity. In another related embodiment, the mutant IDE has a substantially similar, increased, or decreased peptidase activity relative to peptidase activity of a wild-type IDE set forth in SEQ ID NO: 1 or SEQ ID NO:2. In another related embodiment, the mutant IDE has an increased activity relative to that of native or wild-type IDE set forth in SEQ ID NO: 1 or SEQ ID NO:2. In another related embodiment, the recombinant IDE has a decreased activity relative to that of native or wild-type IDE set forth in SEQ ID NO: 1 or SEQ ID NO:2. For example, such mutants can be constitutively more active than unmodified IDE in degrading amyloid β.

In another aspect, the present invention relates to an isolated mutant insulin degrading enzyme (IDE) having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence. In a related embodiment, the isolated mutant IDE has peptidase activity. In another related embodiment, the mutant IDE has a substantially similar, increased, or decreased peptidase activity relative to peptidase activity of a wild-type IDE of SEQ ID NO: 1. In another embodiment, the amino acid sequence is at least 95% identical to SEQ ID NO:1 over its entire length. In another embodiment, the amino acid sequence is at least 97% identical to SEQ ID NO:1 over its entire length.

As used herein, the term "mutant" refers to a native or wild-type IDE sequence such as that shown as SEQ ID NO:1 or SEQ ID NO:2 or variants thereof, with at least one amino acid substitution. The term "mutant" is not limited to any of the mutations described herein which are reflected in amino acid substitutions of the amino acid residues in IDE, but may also include, but are not limited to, other deletions or insertions of nucleotides which may result in changes in the amino acid residues in the amino acid sequence of IDE.

As used herein the term "modulator," "modulating," or "modulate" in connection with the mutant IDEs of the invention refers to any agent that has a functional effect on protein, including physical binding to the protein, alterations of the quantity or quality of expression of the protein, altering any measurable or detectable activity, property, or behavior of the protein, or in the way a substrate or any other compounds or molecules interact with the protein.

As used herein the term "polypeptide" refers to a polymer of amino acids. This term also does not specify, or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those described below can occur anywhere in a polypeptide, including the peptide backbone, the amino acid side-chains and the amino or carboxyl termini. It will be appreciated that the same type of modification maybe present in the same or varying degrees at several sites in a given polypeptide. Also, a given polypeptide may contain many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. [See, for instance, Seifter, et al., Meth Enzymol 182:626-646 (1990)]. Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

As used herein, the term "polynucleotide" refers to a single nucleotide or a polymer of nucleic acid residues of any length. The polynucleotide may contain deoxyribonucleotides, ribonucleotides, and/or their analogs and may be double-stranded or single stranded. A polynucleotide can comprise modified nucleic acids (e.g., methylated), nucleic acid analogs or non-naturally occurring nucleic acids and can be interrupted by non-nucleic acid residues. For example a polynucleotide includes a gene, a gene fragment, cDNA, isolated DNA, mRNA, tRNA, rRNA, isolated RNA of any sequence, recombinant polynucleotides, primers, probes, plasmids, and vectors. Included within the definition are nucleic acid polymers that have been modified, whether naturally or by intervention.

As used herein, the term "operably linked" refers to a linkage of polynucleotide elements in a functional relationship. A sequence which is "operably linked" to a regulatory sequence such as a promoter means that said regulatory element is in the correct location and orientation in relation to the nucleic acid to control RNA polymerase initiation and expression of the nucleic acid of interest. For instance, a promoter or enhancer, is operably linked to a coding sequence if it affects the transcription of the coding sequence.

As used herein, the term "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein, the term "pharmaceutical acceptable carrier" encompasses one or more excipients. In preparing formulations of the compounds of the invention, care should be taken to ensure bioavailability of an effective amount of the agent. Suitable pharmaceutical carriers and formulation techniques are found in standard texts, such as Remington's Pharmaceutical Sciences, Mack Publishing Co., Easton, Pa.

The term "variant" in relation to the amino acid sequence of IDE refers to a naturally occurring allelic variant of IDEs shown in SEQ ID NO:1 or SEQ ID NO:2 or an enzyme which includes any substitution of, variation of, modification of, replacement of, deletion of or addition of one (or more) amino acid from or to the sequence providing the resultant enzyme has an IDE activity, preferably being at least as biologically active as the enzymes shown in SEQ ID NO:1 or SEQ ID NO:2. For example, a variant of IDE can have at least 85%, or at least 90%, or at least 95%, or at least 98% homology (over its entire length) to the sequences shown as SEQ ID NO:1 or SEQ ID NO:2.

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB [Pearson and Lipman, (1988), Proc. Natl. Acad. Sci. USA 85(8): 2444-2448; Altschul et al., (1990), J. Mol. Biol. 215(3):403-410; Thompson et al. (1994), Nucleic Acids. Res. 22(2): 4673-4680; Higgins et al., (1996), Meth. Enzymol. 266:383-402; Altschul et al., (1993), Nature Genetics 3:266-272; Brutlag et al. (1990) Comp. App. Biosci. 6:237-24], the disclosures of which are incorporated by reference in their entireties. In an embodiment, protein and nucleic acid sequence identities are evaluated using the Basic Local Alignment Search Tool ("BLAST") which is well known in the art [e.g., Karlin and Altschul, (1990), Proc. Natl. Acad. Sci. USA 87:2267-2268; Altschul et al., (1997), Nuc. Acids Res. 25:3389-3402] the disclosures of which are incorporated by reference in their entireties.

The terms "native" or "wild-type" as use herein encompass naturally occurring IDEs including SEQ ID NO:1, SEQ ID NO:2 and the allelic variants thereof.

As described above, it is an object of the present invention to provide an isolated mutant insulin degrading enzyme (IDE). In an embodiment, the isolated mutant IDE has at least one amino acid substitution at any of amino acid residues 332, 339, 341, 359, 360, 361, 374, 429, 609, 898, 899 or 901 of SEQ ID NO:1 or SEQ ID NO:2.

By virtue of the present invention, the identification of the location of the allosteric site and the allosteric regulatory of IDE, permits the identification of a equivalent sites on other IDEs which are homologous, by at least 90% sequence identity or by at least 95% sequence identity, to IDE of SEQ ID NO:1 or SEQ ID NO:2. Accordingly, desirable sites for mutation corresponding to the allosteric or allosteric regulatory sites can be identified on other homologous or variant IDEs. In another embodiment other mutations in other amino acid residues of IDE can also be applied in conjunction with the one or more mutations at any of residues 332, 339, 341, 359, 360, 361, 374, 429, 609, 898, 899 or 901 of SEQ ID NO:1 or SEQ ID NO:2; or the corresponding residues in polypeptide sequences with at least 90% sequence identity or at least 95% sequence identity throughout the entire peptide length to SEQ ID NO:1. Such mutations can result in an altered surface charge as compared to the wild-type enzyme. Alternatively, an amino acid residue in IDE's allosteric site and/or allosteric regulatory site can be chosen for replacement or mutation based on its hydrophilic or hydrophobic characteristics.

In accordance to the present invention, the allosteric site of IDE is located on a portion of the substrate binding chamber wall arising largely from domain 4 of the four domain IDE. See FIGS. 2A and B. As described in the Examples that follow, two variants with mutated residues in this site (e.g., IDE$^{K898A,K899A,S901A}$ and IDE$^{R429S}$) showed altered activation by the polyphosphate anions ATP and polyanions (PPPi). It was further shown that IDE$^{K898A,K899A,S901A}$ had an altered intracellular function relative to unmodified IDE, consistent with a role for polyphophate or other polyanion regulation of IDE activity in vivo.

Furthermore, in accordance to the present invention, the allosteric regulatory site of IDE is located at a distal site in domain 2 of IDE. See FIG. 1B. As described in the Examples that follow, the study of several variants with mutated residues in this site (e.g., IDE$^{Y609F}$, IDE$^{V360S}$ and IDE$^{1374S}$) show that the allostery present in the wild type enzyme as well as the enzyme kinetics are affected by these mutations.

In one aspect, the present invention relates to an isolated mutant insulin degrading enzyme (IDE) having at least one amino acid substitution at any of amino acid residues 332, 339, 341, 359, 360, 361, 374, 429, 609, 898, 899 or 901 of SEQ ID NO:1 or SEQ ID NO:2. In a related embodiment, the isolated mutant IDE has peptidase activity. In another related embodiment, the mutant IDE has a substantially similar, increased, or decreased peptidase activity relative to peptidase activity of a wild-type IDE set forth in SEQ ID NO: 1 or SEQ ID NO:2. In another related embodiment, the mutant IDE further has a chemical modification that increases stability of the mutant IDE. In another related embodiment, the chemical modification includes addition of a component selected from the group consisting of a polymer and a second polypeptide. In another related embodiment, the polymer is PEG.

In another aspect, the present invention relates to an isolated mutant insulin degrading enzyme (IDE) having at least two amino acid substitution at any of amino acid residues 332, 339, 341, 359, 360, 361, 374, 429, 609, 898, 899 or 901 of SEQ ID NO:1 or SEQ ID NO:2.

In another aspect, the present invention relates to an isolated mutant insulin degrading enzyme (IDE) having at least one amino acid substitution at any of amino acid residues 332, 339, 341, 359, 360, 361, 374, 429, 609, 898, 899 or 901 of SEQ ID NO:1 or SEQ ID NO:2, with the proviso that if residue 899 is to be substituted, the mutant IDE must also include at least one other amino acid substitution at any of amino acid residues 332, 339, 341, 359, 360, 361, 374, 429, 609, 898, or 901 of SEQ ID NO:1 or SEQ ID NO:2.

In another aspect, the present invention relates to an isolated mutant insulin degrading enzyme (IDE) having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence. In a related embodiment, the isolated mutant IDE has peptidase activity. In another related embodiment, the mutant IDE has a substantially similar, increased, or decreased peptidase activity relative to peptidase activity of a wild-type IDE of SEQ ID NO: 1. In another embodiment, the amino acid sequence is at least 95% identical to SEQ ID NO:1 over its entire length. In another related embodiment, the mutant IDE further has a chemical modification that increases stability of the mutant IDE. In another related embodiment, the chemical modification includes addition of a component selected from the group consisting of a polymer and a second polypeptide. In another related embodiment, the polymer is PEG.

In another aspect, the present invention relates to an isolated mutant insulin degrading enzyme (IDE) having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence; with the proviso that if residue 899 is to be substituted, the mutant IDE must also include at least one other amino acid substitution at any of amino acid residues 332, 339, 341, 359, 360, 361, 374, 429, 609, 898, or 901 of SEQ ID NO:1.

In another aspect, the present invention provides a polynucleotide encoding any of the mutant IDEs of the invention.

In another aspect, the present invention provides a vector including the polynucleotide sequence encoding any of the mutant IDEs of the invention.

In another aspect, the present invention provides a host cell into which has been incorporated the polynucleotide sequence encoding any of the mutant IDEs of the invention.

In another aspect, the present invention provides a pharmaceutical composition having a therapeutically effective amount of a mutant IDE having at least one amino acid substitution at any of amino acid residues 332, 339, 341, 359, 360, 361, 374, 429, 609, 898, 899 or 901 of SEQ ID NO:1 or SEQ ID NO:2. In a related embodiment, the mutant IDE has a peptidase activity. In another related embodiment, the mutant IDE has insulin degrading activity. In another related embodiment, the mutant IDE has amyloid peptide inactivating activity. In another related embodiment, the mutant IDE has amyloid β degrading activity.

In another aspect, the present invention provides a method of treating a condition or disease associated with abnormal IDE levels or activity in a subject in need thereof, said method includes administering to the subject a pharmaceutical composition which has a therapeutically effective amount of a mutant IDE having at least one amino acid substitution at any of amino acid residues 332, 339, 341, 359, 360, 361, 374, 429, 609, 898, 899 or 901 of SEQ ID NO:1 or SEQ ID NO:2.

In another aspect, the present invention provides a method of screening or identifying agents that bind to a mutant IDE; said method includes the steps of (a) contacting an agent with the mutant IDE, wherein the mutant IDE has at least one amino acid substitution at any of amino acid residues 332, 339, 341, 359, 360, 361, 374, 429, 609, 898, 899 or 901 of SEQ ID NO:1 or SEQ ID NO:2; and (b) screening for the binding of the agent to the mutant IDE; and (c) selecting the agent that binds to the mutant IDE.

In another aspect, the present invention provides a method of screening or identifying agents that modulate the activity of a mutant IDE; said method including the steps of (a) contacting a test agent with the mutant IDE in the presence of an IDE substrate, wherein the mutant IDE comprises an amino acid sequence that is at least 90% identical to SEQ ID NO:1 over its entire length and comprises at least one amino acid substitution at any of amino acid residues 332, 339, 341, 359, 360, 361, 374, 429, 609, 898, 899 or 901 of the sequence; (b) assessing the effect of a test agent on activity of the mutant IDE, wherein activity is measured as effect of the test agent on the affinity of the mutant IDE for the IDE substrate or the test agent, rate of the IDE substrate cleavage, or stability of the mutant IDE, relative to a control lacking the test agent; and (c) selecting or identifying any test agent that modulates the affinity of the mutant IDE for the IDE substrate or the test agent, the rate of the IDE substrate cleavage, or the stability of the mutant IDE. In a related embodiment, the test agent is selected from the group consisting of a peptidomimetic, analog of a peptide activators, peptide derivative or analog of Aβ, saccharide, fatty acid, purine, pyrimidine, nucleic acid, derivative or analog thereof, complex organic or simple or complex inorganic molecules, metal-containing compounds, steroids, or steroid analog, fluorogenic peptide or derivative or analog thereof, and any such molecules in combination. In another related embodiment, the activity is assessed by measuring the effect of the test agent on the affinity of the mutant IDE for an IDE substrate. In another related embodiment, the substrate is labeled with a detectable label. In another related embodiment, the substrate is monitored via high performance liquid chromatography.

In another aspect, the present invention provides a method for reducing amyloid β or modulating insulin levels in a subject in need thereof, said method includes administering to said subject an agent that binds to and/or modulate the activity of the mutant IDE in an amount effective to reduce amyloid β (Aβ) or insulin.

The present invention provides extensive information regarding the discovery of an allosteric site and an allosteric regulatory site on IDE, which involve amino acid residues H332, G339, E341, L359, V360, G361, I374, R429, Y609, K898, K899 or S901 of SEQ ID NO:1 or SEQ ID NO:2 or variants thereof. This information makes it possible for one skilled in the art to design mutant IDE polypeptides having increased or decreased activities or particular substrate-binding specificities useful for particular use such as for treating Alzheimer's disease or diabetes. In addition, a skilled artisan can use the information provided herein to design mutant IDEs for therapeutic purposes such as for treating conditions or diseases associated with IDE including Alzheimer's disease or diabetes. Further, the mutant IDEs of the present invention can be used for screening agents (e.g., small molecules, peptides, etc.) that bind to and modulate the activity of IDE. Also, the information presented herein can be used to design diagnostic methods for identifying the particular IDE mutation(s) in subjects suffering from or being susceptible to IDE associated diseases or conditions. Once, such mutations are diagnosed, methods such as gene therapy may be used to correct or compensate for the native IDE malfunction.

Polypeptides—

The mutant IDEs of the present invention may be prepared in a number of ways that are known by a person skilled in the art. For example, mutations may be introduced by means of oligonucleotide-directed mutagenesis or other conventional methods. Alternatively, mutants of IDE may be generated by site specific replacement of a particular amino acid with an unnaturally occurring amino acid. This may be achieved by growing a host organism capable of expressing either the wild-type or mutant polypeptide on a growth medium depleted of one or more natural amino acids but enriched in one or more corresponding unnaturally occurring amino acids. The expression, activity (eg. kinetic constants) and/or the crystallization properties of the mutants may be determined using the methods described in the Examples.

In an embodiment, the present disclosure encompasses an isolated mutant insulin degrading enzyme (IDE) having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence. As used herein, "percent identity" or "% identity" of a mutant of IDE is determined by comparing the whole of SEQ ID NO:1 or SEQ ID NO:2 to the whole of sequence of the mutant using a computer implemented algorithm, specifically, the algorithm of Karlin and Altschul (Proc. Natl. Acad. Sci. 87: 2264-68 (1990), modified Proc. Natl. Acad. Sci. 90: 5873-77 (1993)), using the default parameters. Because of the extensive amino acid identity between rat IDE and other mammalian homologs including human IDE, it is envisioned that, using the guidance provided herein, analogous mutants of homologs of rat IDE having altered activity could readily be made and used. One exemplary homolog of SEQ ID NO:1 with at least 95% amino acid homology is SEQ ID NO:2 depicted in FIG. 13.

In another embodiment, a mutant IDE according to the teaching of the present invention has at least 70%, 80%, 90%, 95%, 98%, 99% amino acid sequence identity with SEQ ID NO:1. In general, the mutant exhibits substantially the same or greater IDE activity than a native IDE or than the activity of IDE represented by SEQ ID NO:1 or SEQ ID NO:2.

In general, IDE mutants of the invention include variants in which at least one residue at positions 332, 339, 341, 359, 360, 361, 374, 429, 609, 898, 899 or 901 (in SEQ ID NO:1 or SEQ ID NO:2) has been substituted by other amino acids, and may further include the possibility of inserting an additional residue or residues as well as the possibility of deleting one or more residues from the parent sequence or adding one or more residues to the parent sequence. Any amino acid substitution, insertion, or deletion is encompassed by the invention.

For example, substantial modifications in the biological properties of the peptide/polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe. Non-conservative substitutions will entail exchanging a member of one of these classes for another class.

For increased stability and half-life, the mutant polypeptides of the invention can be modified by chemical moieties and/or functional groups such as an amine, carboxyl, thiol or hydroxyl group. See, e.g., Kochendoerfer et al., Science, 299: 884-887 (2003) which is incorporated herein by reference in its entirety. Chemicals useful in making such modifications include, but are not limited to, polymers like polyethylene glycol (PEG), polypeptides such as the Fc portion of an antibody or chemical groups.

The polypeptides of the invention can be differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity. See. U.S. Pat. No. 4,179,337. The chemical moieties for derivatization may be selected. See, U.S. Pat. No. 4,179,337 which disclosure is hereby incorporated by reference in its entirety. The chemical moieties for derivatization can be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three, or more attached chemical moieties. The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384 and Malik et al., Exp Hematol. 20(8):1028-35 (1992), which disclosures are hereby incorporated by reference in their entireties. For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary), may be by purification of the N-terminally pegylated material from a population of pegylated protein molecules. Selective proteins chemically modified at the N-terminus modification may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

In addition, chemical modifications, such as polymer conjugation or addition of an Fc polypeptide to proteins, may increase protein solubility and stability. Polymer conjugation has been shown to also reduce protein immunogenicity and prolong the plasma half-life of proteins through prevention of renal elimination and avoidance of receptor-mediated protein uptake by cells of the reticuloendothelial system. See Vicent and Duncan, Trends Biotechnol 24:39-47 (2006). The size of the polymer used may be determined by one of skill in the art, but suitably ranges between 5,000 and 40,000 g/mol, suitably between 7,000 and 30,000 g/mol.

Polynucleotides—

Another aspect of the invention relates to polynucleotide sequences encoding the mutant IDE proteins of the invention. Further included in the present invention are polynucleotides encoding the polypeptides of the present invention that are fused in frame to the coding sequences for additional heterologous amino acid sequences. Also included in the present invention are nucleic acids encoding polypeptides of the present invention together with additional, non-coding sequences, including, but not limited to, non-coding 5' and 3' sequences, vector sequence, sequences used for purification, probing, or priming. For example, heterologous sequences include transcribed, untranslated sequences that may play a role in transcription and mRNA processing, such as ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification or detection of the fused polypeptide. In certain embodiments of this aspect of the invention, the tag amino acid sequence is a hexa-histidine peptide, such as the tag provided in a pQE vector (QIAGEN), or in any of a number of additional, commercially available vectors. For instance, hexa-histidine provides for the convenient purification of the fusion protein (see, Gentz et al., Proc Natl Acad Sci USA February; 86(3):821-4 (1989)). The "HA" tag is another peptide useful for purification which corresponds to an epitope derived from the influenza hemagglutinin protein (see, Wilson, et al., Cell July; 37(3):767-78 (1984)).

Polynucleotides of the invention capable of selectively hybridizing to the nucleotide sequences encoding polypeptide shown in SEQ ID NO:1, or to its complement, will be generally at least 70%, preferably at least 80 or 90% and more preferably at least 95% or 98% homologous to the SEQ ID NO:1 corresponding nucleotide sequence over a region of at least 20, preferably at least 25 or 30, for instance at least 40, 60 or 100 or more contiguous nucleotides. Polynucleotides of the invention will be capable of encoding a mutant IDE with at least one amino acid substitution at any of amino acid residues 332, 339, 341, 359, 360, 361, 374, 429, 609, 898, 899 or 901 of SEQ ID NO:1 or SEQ ID NO:2 or variants thereof.

variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the sequence in the attached sequence listings under conditions of medium to high stringency. Similar considerations apply to obtaining species homologues and allelic variants of the polypeptide or nucleotide sequences of the invention.

Polynucleotide variants and strain/species homologues capable of coding for mutant IDEs of the invention may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterized sequences. This may be useful where for example silent codon changes are required to sequences to optimize codon preferences for a particular host cell in which the polynucleotide sequences are being expressed. Other sequence changes may be desired in order to introduce restriction enzyme recognition sites, or to alter the property or function of the mutant IDE polypeptides encoded by the polynucleotides.

Constructs—

In another aspect of the invention, the coding polynucleotide sequences encoding the mutant IDE proteins of the invention may be operably linked to a promoter in a DNA construct using conventional cloning technology. The promoter may be a homologous or a heterologous promoter, i.e., a promoter not natively associated with the coding sequence. The promoter may be constitutive or inducible. Suitably, the promoter includes an expression control sequence near the start site of transcription. A promoter may include enhancer or repressor elements that may be non-contiguous with the start site of transcription. The polynucleotide may be provided within a vector, for example, a plasmid, cosmid, or virus.

The construct may even contain or express a marker which allows for the selection of the genetic construct in, for example, a bacterium. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

Vectors—

The term "vector" includes expression vectors and transformation vectors and shuttle vectors. The term "expression vector" means a construct capable of in vivo or in vitro expression. The expression vector can be any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained in U.S. Pat. No. 5,082,767, which disclosure is hereby incorporated by reference in its entirety.

The vectors of the present invention may be transformed into a suitable host cell as described below to provide for expression of a polypeptide of the present invention. Thus, in a further aspect the invention provides a process for preparing polypeptides according to the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter.

The vectors of the present invention may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in filamentous fungi), the ampicillin resistance gene (E. coli), the neomycin resistance gene (Bacillus) and the E. coli uidA gene, coding for .beta.-glucuronidase (GUS).

Vectors may be used in vitro, for example for the production of RNA or used to transfect or transform a host cell.

Thus, polynucleotides of the present invention can be incorporated into a recombinant vector (typically a replicable vector), for example a cloning or expression vector. The vector may be used to replicate the nucleic acid in a compatible host cell. Thus in a further embodiment, the invention provides a method of making polynucleotides of the present invention by introducing a polynucleotide of the present invention into a replicable vector, introducing the vector into a compatible host cell, and growing the host cell under conditions which bring about replication of the vector. The vector may be recovered from the host cell. Suitable host cells are described below in connection with expression vectors.

Host Cells—

Another aspect of the invention relates to a cell comprising the polynucleotides described above. The cell is not limited to any particular cell type, but must be capable of expressing the polypeptide encoded by the construct under suitable conditions. Thus, a further embodiment of the present invention provides host cells transformed or transfected with a polynucleotide of the present invention. Preferably said polynucleotide is carried in a vector for the replication and expression of said polynucleotides. The cells will be chosen to be compatible with the said vector and may for example be prokaryotic (for example bacterial), fungal, yeast or plant cells. The gram-negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*. Suitable cell types for expression of the polypeptides of the present invention include prokaryotic cells such as bacteria, or eukaryotic cells, including, for example, tumor cells, immortalized cells, primary cells, stem cells, BALB/C cells, neuronal cells, and the like. The polynucleotides may be introduced into cells of a target tissue or into a cell in culture by way of any suitable means. Many such approaches are routinely practiced in the art. For example, one of skill in the art can select any method by which a polynucleotide (e.g., DNA) can be introduced into an organelle, a cell, a tissue or an organism. Cells may be selected to study the effects of a mutant IDE activity on specific cell types, or may be selected as a model for diseases that are correlated with altered IDE activity or IDE substrate concentration. Cells used in the assay described in the Examples are also suitable. Suitable methods of administering the construct to a cell may include, but are not limited to, use of non-viral and viral vectors. Suitable viral vectors may include, but are not limited to, retroviruses (including lentiviruses), adenoviruses, adeno-associated viruses and herpes simplex virus type 1 or type 2. In vitro delivery methods include, but are not limited to, transfection, including microinjection, electroporation, calcium phosphate precipitation, using DEAE-dextran followed by polyethylene glycol, direct sonic loading, liposome-mediated transfection and receptor-mediated transfection, microprojectile bombardment, agitation with silicon carbide fibers, desiccation/inhibition-mediated DNA uptake, transduction by viral vector, and/or any combination of such methods.

Transfection of a mutant IDE expression vector into mouse NTH 3T3 cells is but one embodiment of introducing polynucleotides into host cells. Introduction of a polynucleotide encoding a polypeptide into a host cell can be effected by calcium phosphate transfection, DEAE-dextran mediated transfection, cationic lipid-mediated transfection, electroporation, transduction, infection, or other methods. Such methods are described in many standard laboratory, manuals, such as Davis et al., (1986) Basic Methods in Molecular Biology; ed., Elsevier Press, NY, which disclosure is hereby incorporated by reference in its entirety. It is specifically contemplated that the polypeptides of the present invention may in fact be expressed by a host cell lacking a recombinant vector or naturally produced by a cell.

Alternatively, the mutant IDE polypeptide to be expressed may also be a product of transgenic animals, i.e., as a component of the milk of transgenic cows, goats, pigs or sheep which are characterized by somatic or germ cells containing a nucleotide sequence encoding the protein of interest.

Recovery and Purification of Polypeptides—

A polypeptide of this invention can be recovered/isolated and purified from recombinant cell cultures by well-known methods including differential extraction, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In one embodiment, high performance liquid chromatography ("HPLC") is employed for purification. A recombinantly produced version of a mutant IDE polypeptide can be substantially purified using techniques described herein or otherwise known in the art, such as, for example, by the one-step method described in Smith et al., Gene 67(1): 31-40 (1988). Polypeptides of the invention can also be purified from recombinant sources using antibodies directed against the polypeptides of the invention, such as those described herein, in methods which are well known in the art of protein purification.

In an embodiment, the recombinantly expressed mutant IDE polypeptide is purified using standard immunochromatography techniques such as Immunoaffinity Chromatography. In such procedures, a solution containing the protein of interest, such as the culture medium or a cell extract, is applied to a column having antibodies against the protein attached to the chromatography matrix. The recombinant protein is allowed to bind the immunochromatography column. Thereafter, the column is washed to remove non-specifically bound proteins. The specifically bound secreted protein is then released from the column and recovered using standard techniques.

Compositions and/or Pharmaceuticals—

Another aspect of the invention provides compositions comprising a polypeptide, or polynucleotide of the invention, a mutant IDE or a polynucleotide encoding same, or other molecules or agents that can increase or decrease the levels or the activity of IDE (that are identified by the screening methods of the present invention). Such compositions may be pharmaceutical compositions formulated for use as a therapeutic.

In one embodiment, the invention provides a composition that comprises a mutant polypeptide of insulin degrading enzyme (IDE) at least one amino acid substitution at any of amino acid residues 332, 339, 341, 359, 360, 361, 374, 429, 609, 898, 899 or 901 of SEQ ID NO:1 or SEQ ID NO:2. In one embodiment, the invention provides a composition that comprises a mutant polypeptide of insulin degrading enzyme (IDE) having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence. Alternatively, the invention provides a composition that comprises a polynucleotide which encodes a polypeptide of the invention or vector that express a polypeptide of the invention In another embodiment, the invention provides a composition that comprises a modulator (as will be discussed below) of the level or activity of the mutant IDE polypeptide of the invention (e.g., an inhibitor or an activator), or a molecule that comprises a modulator.

Such compositions may be pharmaceutical compositions. Typically, a pharmaceutical composition comprises a therapeutically effective amount of an active agent and is formulated with a suitable excipient or carrier. The invention also provides pharmaceutical compositions for the treatment of various disorders relating to IDE including neurological disorders. These compositions may include a protein and/or nucleic acid of the invention, and can be formulated as described herein. Alternately, these compositions may include an antibody which specifically binds to a protein of the invention and/or an antisense polynucleotide which is complementary to a polynucleotide of the invention and can be formulated as described herein.

The pharmaceutical compositions of the invention can be prepared in any suitable manner known in the pharmaceutical art. The carrier or excipient may be a solid, semisolid, or liquid material that can serve as a vehicle or medium for the active ingredient. Suitable carriers or excipients are well known in the art and include, but are not limited to saline, buffered saline, dextrose, water, glycerol, ethanol, and combinations thereof. The pharmaceutical compositions may be adapted for oral, inhalation, parenteral, or topical use and may be administered to the patient in the form of tablets, capsules, aerosols, inhalants, suppositories, solutions, suspensions, powders, syrups, and the like.

The vector of the invention can also be incorporated into pharmaceutical compositions suitable for administration to a subject. A pharmaceutical composition may comprise the vector of the invention and a pharmaceutically acceptable vector carrier. The term "pharmaceutically acceptable vector carrier" includes any and all solvents, dispersion media, coatings, antibacterial and antifungal agents, isotonic and absorption delaying agents, and the like that are physiologically compatible. Examples of pharmaceutically acceptable vector carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In one embodiment, the vector is administered by intravenous infusion or injection. In another embodiment, the vector is administered by intramuscular or subcutaneous injection. In another embodiment, the vector is administered perorally. In the most preferred embodiment, the vector is delivered to a specific location using stereostatic delivery.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The vector of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. Sustained and Controlled Release Drug Delivery Systems, J. R. Robinson, ed., Marcel Dekker, Inc., New York, 1978. The pharmaceutical compositions of the invention may include a "therapeutically effective amount" or a "prophylactically effective amount" of the vectors of the invention. A "therapeutically effective amount" refers to an amount effective, at dosages and for periods of time necessary, to achieve the desired therapeutic result.

A therapeutically effective amount of the vector may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

In general, a therapeutically effective daily oral or intravenous dose of the agents (including mutant IDEs or compounds or peptides capable of modulating the activity of native or mutant IDEs) of the present invention is likely to range from 0.01 to 50 mg/kg body weight of the subject to be treated, preferably 0.1 to 20 mg/kg. The agents of the present invention may also be administered by intravenous infusion, at a dose which is likely to range from 0.001 10 mg/kg/hr.

Tablets or capsules of the agents may be administered singly or two or more at a time, as appropriate. It is also possible to administer the agents of the present invention in sustained release formulations.

Thus, the present invention also provides a method of treating an individual in need of same due to IDE activity comprising administering to said individual an effective amount of the pharmaceutical composition of the present invention.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the agents of the present invention may typically be from 10 to 500 mg (in single or divided doses). Thus, and by way of example, tablets or capsules may contain from 5 to 100 mg of active agent for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

In some applications, generally, in humans, oral administration of the agents of the present invention is the preferred route, being the most convenient and can in some cases avoid disadvantages associated with other routes of administration—such as those associated with intracavernosal (i.c.) administration. In circumstances where the recipient suffers from a swallowing disorder or from impairment of drug absorption after oral administration, the drug may be administered parenterally, e.g. sublingually or buccally.

For veterinary use, the agent of the present invention is typically administered as a suitably acceptable formulation in accordance with normal veterinary practice and the veterinary surgeon will determine the dosing regimen and route of administration which will be most appropriate for a particular animal. However, as with human treatment, it may be possible to administer the agent alone for veterinary treatments.

Typically, the pharmaceutical compositions—which may be for human or animal usage—will comprise any one or more of a pharmaceutically acceptable diluent, carrier, excipient or adjuvant. The choice of pharmaceutical carrier, excipient or diluent can be selected with regard to the intended route of administration and standard pharmaceutical practice. As indicated above, the pharmaceutical compositions may comprise as—or in addition to—the carrier, excipient or diluent any suitable binder(s), lubricant(s), suspending agent(s), coating agent(s), solubilizing agent(s).

In some embodiments of the present invention, the pharmaceutical compositions will comprise one or more of: an agent that has been screened by an assay of the present invention; an agent that is capable of interacting with a mutant IDE of the present invention and modulating its activity.

Methods of Treatment—

In another aspect, the present invention encompasses treating diseases and disorders associated with IDE such as Alzheimer's disease, diabetes type 2, chronic schizophrenia, neurodegenerative disorders, metabolic syndrome, hypo or hyper insulin disorders, and many others. In one embodiment of this aspect, the present invention is directed to a method of treating a condition or disease associated with abnormal IDE levels or activity in a subject in need thereof, said method comprises administering to the subject a pharmaceutical composition comprising a therapeutically effective amount of a mutant IDE having at least one amino acid substitution at any of amino acid residues 332, 339, 341, 359, 360, 361, 374, 429, 609, 898, 899 or 901 of SEQ ID NO:1 or SEQ ID NO:2. In a related embodiment, the mutant IDE has an altered (i.e., increased or decreased) IDE activity relative to a native IDE of said subject.

In another embodiment, the present invention is directed to a method of treating a condition or disease associated with abnormal IDE levels or activity in a subject in need thereof, said method comprises administering to the subject a pharmaceutical composition described above. In a related embodiment, the pharmaceutical composition includes one or more of: an agent that has been screened by an assay of the present invention; an agent that is capable of interacting with a mutant IDE of the present invention and modulating its activity. Various modes of administration and dosages of the contemplated pharmaceutical compositions are described above.

In another embodiment, the treatment method can be a gene therapy method. The use of mutant IDE of the invention in vector constructs for gene therapy is contemplated in one embodiment of this invention. In a similar embodiment, mutant IDE polypeptide can be in a fusion construct wherein the mutant IDE of the invention is fused to another peptide which facilitates the increased serum half-life or serum stability of the polypeptides of the instant invention and which is suited to gene therapy treatments (e.g., modified transferrin fusion constructs disclosed in U.S. Pat. No. 7,176,278, the content of which is hereby incorporated by reference in its entirety).

The successful use of gene therapy to express a soluble fusion protein is known in the art. Briefly, gene therapy via injection of an adenovirus vector containing a gene encoding a soluble fusion protein consisting of cytotoxic lymphocyte antigen 4 (CTLA4) and the Fc portion of human immunoglobulin G1 was recently shown in Ijima et al. *Human Gene Therapy,* 12(9):1063-77 (2001). Gene therapy is also described in a number of U.S. patents including U.S. Pat. No. 6,225,290 (issued May 1, 2001); U.S. Pat. No. 6,187,305 (issued Feb. 13, 2001); and U.S. Pat. No. 6,140,111 (issued Oct. 31, 2000), the contents of which are hereby incorporated by reference in their entirety.

U.S. Pat. No. 6,225,290 provides methods and constructs whereby intestinal epithelial cells of a mammalian subject are genetically altered to operatively incorporate a gene which expresses a protein which has a desired therapeutic effect. Intestinal cell transformation is accomplished by administration of a formulation composed primarily of naked DNA, and the DNA may be administered orally. Oral or other intragastrointestinal routes of administration provide a simple method of administration, while the use of naked nucleic acid avoids the complications associated with use of viral vectors to accomplish gene therapy. The expressed protein is secreted directly into the gastrointestinal tract and/or blood stream to obtain therapeutic blood levels of the protein thereby treating the patient in need of the protein. The transformed intestinal epithelial cells provide short or long term therapeutic cures for diseases associated with a deficiency in a particular protein or which are amenable to treatment by over-expression of a protein.

U.S. Pat. No. 6,187,305 provides methods of gene or DNA targeting in cells of vertebrate, particularly mammalian, origin. Briefly, DNA is introduced into primary or secondary cells of vertebrate origin through homologous recombination or targeting of the DNA, which is introduced into genomic DNA of the primary or secondary cells at a preselected site.

U.S. Pat. No. 6,140,111 (issued Oct. 31, 2000) describes retroviral gene therapy vectors. The disclosed retroviral vectors include an insertion site for genes of interest and are capable of expressing high levels of the protein derived from the genes of interest in a wide variety of transfected cell types. Also disclosed are retroviral vectors lacking a selectable marker, thus rendering them suitable for human gene therapy in the treatment of a variety of disease states without the co-expression of a marker product, such as an antibiotic. These retroviral vectors are especially suited for use in certain packaging cell lines. The ability of retroviral vectors to insert into the genome of mammalian cells have made them particularly promising candidates for use in the genetic therapy of genetic diseases in humans and animals. Genetic therapy typically involves (1) adding new genetic material to patient cells in vivo, or (2) removing patient cells from the body, adding new genetic material to the cells and reintroducing them into the body, i.e., in vitro gene therapy. Discussions of how to perform gene therapy in a variety of cells using retroviral vectors can be found, for example, in U.S. Pat. Nos. 4,868,116, issued Sep. 19, 1989, and 4,980,286, issued Dec. 25, 1990 (epithelial cells), WO89/07136 published Aug. 10, 1989 (hepatocyte cells), EP 378,576 published Jul. 25, 1990 (fibroblast cells), and WO89/05345 published Jun. 15, 1989 and WO90/06997, published Jun. 28, 1990 (endothelial cells), the disclosures of which are incorporated herein by reference.

Screening Methods—

Any compound interacting with a mutant IDE of the present invention, and thereby promoting or interfering with its activities can also be used as a method of treating any of the pathologies associated with IDE. Such compounds can be identified, e.g., using interaction-screening approaches such as, but not limited to, co-immunoprecipitation, two-hybrid methods. Further, compounds can be screened for the ability to modulate the activity of the present protein by providing a cell expressing the present protein, or providing lipid bilayers reconstituted with the present protein, and detecting the ability of a compound to modulate the activity of the present protein in the cell or in the bilayer. Such activity can be detected in any of a large number of ways, including but not limited to detecting calcium flux or calcium signaling in the cells or membranes, e.g. as manifest in the activity of downstream members of the signal transduction pathway. The present invention also provides an in vitro method to identify any compound/agent able to promote or interfere with some or all activities of the mutant IDEs of the present invention, the method comprising the steps of contacting a mutant IDE with a test compound/agent and detecting the ability of the compound/agent to bind to or modulate the activity of the mutant IDE. Also in this embodiment, the present protein or any effective compound identified by this way of investigation useful for the treatment of disorders described above can be used in combination with other drugs or compounds.

Thus, in another aspect, the present invention relates to a method of screening for a modulator of IDE wherein the method includes the use of a mutant IDE with at least one amino acid substitution at any of amino acid residues 332, 339, 341, 359, 360, 361, 374, 429, 609, 898, 899 or 901 of SEQ ID NO:1 or SEQ ID NO:2, according to the present invention. In one embodiment, the method comprises the steps of: (a) employing the allosteric site and/or the allosteric regulatory site of IDE or physical properties thereof to design or select or synthesize a putative modulator of IDE; (b) contacting the putative modulator of IDE with IDE or a mutant thereof with at least one amino acid substitution at any of amino acid residues 332, 339, 341, 359, 360, 361, 374, 429, 609, 898, 899 or 901 of SEQ ID NO:1 or SEQ ID NO:2 in the presence of a substrate; and (d) screening the putative modulator of IDE in an assay for the potential to modulate IDE's activity or substrate binding specificity.

In another embodiment, the present invention relates to a method of screening agents that bind to a mutant IDE; said method includes the steps of (a) contacting an agent with the mutant IDE, wherein the mutant IDE has at least one amino acid substitution at any of amino acid residues 332, 339, 341, 359, 360, 361, 374, 429, 609, 898, 899 or 901 of SEQ ID NO:1 or SEQ ID NO:2; and (b) screening for the binding of the agent to the mutant IDE; and (c) selecting the agent that binds to the mutant IDE. In another embodiment, the present invention relates to a method of screening agents modulate the activity of a mutant IDE; said method includes the steps of (a) contacting an agent with the mutant IDE in the presence of a substrate, wherein the mutant IDE has at least one amino acid substitution at any of amino acid residues 332, 339, 341, 359, 360, 361, 374, 429, 609, 898, 899 or 901 of SEQ ID NO:1 or SEQ ID NO:2; and wherein the agent binds to the recombinant IDE; (b) screening the agent for its modulating the activity of the mutant IDE, wherein the modulation comprises an equal, increased, or decreased catalytic activity relative to the catalytic activity of a native or wild-type IDE of SEQ ID NO: 1 or SEQ ID NO:2 or variants thereof; and (c) selecting the agent that can modulate the activity of the mutant IDE.

In another embodiment, the present invention relates to an in vitro method of identifying a candidate compound for use in reducing formation or growth of amyloid plaque or for reducing amyloid peptide neurotoxicity, including: (a) assessing the effect of a test compound/agent on activity of a mutant insulin degrading enzyme (IDE), wherein the mutant IDE has an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence, and wherein activity is measured as effect of the test compound/agent on the affinity of the mutant IDE for an IDE substrate or the test compound/agent, rate of IDE substrate cleavage, or stability of the IDE, relative to a control lacking the test compound/agent, wherein the test compound/agent is selected from the group consisting of: a peptidomimetic, analog of a peptide activators, peptide derivative or analog of Aβ, saccharide, fatty acid, purine, pyrimidine, nucleic acid, derivative or analog thereof, complex organic or simple or complex inorganic molecules, metal-containing compounds, steroids, or steroid analog, fluorogenic peptide, or derivative or analog thereof and any such molecules in combination; and (b) identifying the test compound/agent as a candidate compound for use in reducing formation or growth of amyloid plaque or for reducing amyloid peptide neurotoxicity if it enhances the activity or stability of said mutant IDE. In a related embodiment, said test compound/agent is fluorogenic peptide Abz-GGFLRKHGQ-EDDnp (SEQ ID NO:3). In another related embodiment, the activity is assessed by measuring the effect of the test compound/agent on the affinity of the mutant IDE for an IDE substrate. In another related embodiment, the substrate is labeled with a detectable label. In another related embodiment, the substrate is monitored via high performance liquid chromatography.

In another embodiment, the present invention relates to a method of assessing the effect of a test compound/agent on a mutant IDE activity and ability to degrade Aβ, including contacting said test compound/agent with a mutant IDE which has an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence; and identifying a test compound/agent that enhances the mutant IDE activity or stability wherein the activity is measured as effect of the test compound/agent on the affinity of the mutant IDE for a substrate or the test compound/agent, rate of the IDE substrate cleavage, or stability of the IDE, relative to a control lacking the test compound/agent, wherein the test compound/agent is selected from the group consisting of: a peptidomimetic, analog of a peptide activator, peptide derivative or analog of Aβ, saccharide, fatty acid, purine, pyrimidine, nucleic acid, derivative or analog thereof, complex organic or simple or complex inorganic molecules, metal-containing compounds, steroids, or steroid analog, fluorogenic peptide, or derivative or analog thereof and any such molecules in combination. In a related embodiment, said test compound/agent is peptide Abz-GG-FLRKHGQ-EDDnp (SEQ ID NO:3).

By way of example, the structure co-ordinates or physical properties of the allosteric site and/or the allosteric regulating site of IDE, in accordance with this invention, can be used to design compounds or agents that bind to the enzyme and modulate or alter the physical properties (e.g., substrate binding specificity, ATP, anion or polyanion binding ability, enzyme activity, enzyme solubility, etc.) of the enzyme. The designed modulators, in accordance with the methods of the invention, can then be screened for their action as competitive activators of IDE with binding specificity to amyloid β or their action as competitive inhibitors of IDE with binding specificity to insulin. Compounds can also be designed that act as non-competitive activators or inhibitors of IDE. Similarly, non-competitive modulators that bind to the allosteric site of IDE whether or not it is bound to another chemical entity/substrate may be designed using the structure co-ordinates or characteristics of IDE's allosteric site as described herein.

For example, according to the Examples of the present invention, it has been found that the allosteric site of IDE, which includes amino acid residues 429, 898, 899 and 901 of SEQ ID NO:1, is positively charged. This may present an opportunity for covalent modification, by, for example, the introduction of an alkyl halide or halo-ketone functionality into the modulators that can alkylate the lysine amine, or a-ketone or aldehyde that can form a Schiff's base with the lysine amine, or the use of activated ester or thioester groups, or other modified carboxyl groups susceptible to nucleophilic attack.

An IDE crystal may be probed with a variety of different chemical entities or test compounds/agents to determine the interaction between modulators of IDE and the enzyme at its allosteric site disclosed herein. For example, X-ray diffraction data collected from crystals grown in the presence of chemical entities or test compounds/agents may allow the elucidation of how the chemical entities or test compounds/agents interact with IDE at its allosteric site. Molecules that bind to the allosteric site, in accordance to the present invention, can then be designed and synthesized and tested for their IDE modulating activity.

Small molecule databases or test compounds/agents may be screened for chemical entities or compounds that can bind to IDE at its allosteric site and/or allosteric regulatory site, involving amino acid residues 332, 339, 341, 359, 360, 361, 374, 429, 609, 898, 899 or 901 of SEQ ID NO:1 or SEQ ID NO:2 or variants thereof. Thus, in an embodiment, the putative IDE modulator is from a library of compounds or a database. In this screening, the quality of fit of such entities or compounds to the allosteric site can be judged by various methods such as shape complementarity or estimated interaction energy (Meng, E. C. et al., J. Comp. Chem., 13, pp. 505-524 (1992)). A same screening method can be used to identify compounds that can bind to the allosteric sites of other IDE homologs with at least 95% sequence homology to SEQ ID NO:1 or SEQ ID NO:2.

The design of compounds that bind to IDE's allosteric site and/or allosteric regulatory site and modulate same according to the present invention generally involves consideration of two factors. First, the compound must be capable of physically and structurally associating with IDE at its allosteric site. Second, the compound must be able to assume a conformation that allows it to associate with IDE at its allosteric site. Although certain portions of the compound may not directly participate in the association with IDE at its allosteric site, those portions may still influence the overall conformation of the molecule.

The potential modulating or binding effect of a chemical compound on IDE through its allosteric site and/or allosteric regulatory site may be analyzed prior to its actual synthesis and testing by the use of computer modeling techniques. If the theoretical structure of the given compound suggests insufficient interaction and association with IDE through its allosteric site and/or allosteric regulatory site, then synthesis and testing of the compound may be obviated. However, if computer modeling indicates a strong interaction, the molecule may be synthesized and tested for its ability to bind to IDE through its allosteric site and modulate (eg. Activate or inhibit IDE's activity or substrate binding specificity) using the fluorescent substrate assay of Thornberry et al., Methods Enzymoi. 322, pp 100-110 (2000). In this manner, synthesis of inactive compounds may be avoided.

Once a compound has been designed or selected by the above methods, the efficiency with which that compound may bind to IDE through its allosteric site may be computationally evaluated. Specific computer software may be used to evaluate the efficiency of binding (e.g., to evaluate compound deformation energy and electrostatic interaction) such as QUANTA/CHARMM (Accelrys Inc., USA).

Once an IDE-modulating compound has been selected or designed, as described above, substitutions may be made (e.g., in atoms or side groups) to improve or modify the binding properties. Test compounds/agents or modulators of IDE which are identified using the allosteric site of IDE in accordance to the findings of the present invention may be screened in assays.

Screening assays can be, for example in vitro, in cell culture, and/or in vivo. Biological screening assays preferably center on activity-based response models, binding assays (which measure how well a compound binds), and bacterial, yeast and animal cell lines (which measure the biological effect of a compound in a cell). The assays can be automated for high capacity-high throughput screening (HTS) in which large numbers of compounds can be tested to identify compounds with the desired activity. Current screening technologies are described in Handbook of Drug Screening, edited by Ramakrishna Seethala, Prabhavathi B. Fernandes. New York, N.Y., Marcel Dekker, (2001).

In one embodiment, the screening methods involve assessing the effect of a test compound/agent on activity of a mutant IDE. In particular embodiments, the method involves assessing the effect of a test compound/agent on activity of a mutant IDE of the present invention. As used herein, the term "assessing" with respect to "activity" of a mutant IDE, refers to the process of determining, either qualitatively or quantitatively, the amount of a biological activity of the IDE. A compound that enhances activity relative to a suitable control, such as a sample that is untreated, or which is treated with a vehicle, is identified. A compound that "enhances" activity can be a compound that increases activity by any detectable amount, such as an increase of at least 1%, 2.5%, 5%, 10%, 25%, 50%, or more. Such an increase in activity can be a result of the compound acting by any mechanism. For example, the compound can affect the affinity of the enzyme for its substrate, the affinity of the enzyme for the product, the rate of substrate cleavage, the stability of the enzyme, or the like. In a particular embodiment, an identified compound can be one that increases activity to a statistically significant extent relative to a control.

Methods of assessing activity of a mutant IDE of the present invention can take advantage of any biological activity of an IDE, including the ability of the IDE to cleave a substrate. For example, as disclosed herein, IDE cleaves amyloid β peptides initially between the $His^{13}$-$His^{14}$, $His^{14}$-$Gln^{15}$ and $Phe^{19}$-$Phe^{20}$ bonds, and also cleaves insulin, glucagons and atrial naturitic peptide. Thus, a mutant IDE activity assays can involve the step of measuring the cleavage of an Aβ peptide, or of a synthetic peptide containing amino acids flanking a cleavage site of an Aβ peptide. Either the reduction in the amount of substrate, or the increase in the amount of one or more cleavage products, can be assessed in such assays.

Methods such as HPLC or mass spectrometry can be used to directly monitor substrates and cleavage products. Alternatively, an IDE substrate sequence can be detectably labeled in such a manner that the substrate and product have qualitatively or quantitatively different properties. For example, an IDE substrate sequence can be flanked by a donor fluorescent moiety and an acceptor quencher moiety. The uncleaved substrate has low fluorescence due to quenching of the donor by the acceptor. Upon cleavage by the mutant IDE, the donor and acceptor moieties are no longer in proximity, and the donor fluoresces strongly because it is no longer quenched. The amount of donor fluorescence is directly proportional to the mutant IDE activity. An exemplary peptide substrate containing donor and acceptor moieties and its use in peptidase activity assays, Abz-GGFLRKHGQ-EDDnp (SEQ ID NO:3), is described in the Examples. Another fluorogenic assay may be by using the peptide substrate glutaryl-Ala-Ala-Phe-4-methoxy-2-naphthylamide. In that assay, cleavage of the peptide substrate by a peptidase yields Phe-4-methoxy-2-naphthylamide which in turn yields a fluorescent 4-methoxy-2-naphthylamine when cleaved by an aminopeptidase (see also Thompson et al. (2003) Arch. Biochem. Biophys. 413:236-242). Other assays for determining peptidase activity are well known in the art and can be adapted for use in assessing mutant IDE activity, based on knowledge of the substrates and cleavage sites therein.

The screening assays described herein can involve contacting either an in vivo or in vitro sample with a test compound/agent, and assessing binding or activity. As used herein, "contacting" refers to bringing into association, either directly or indirectly, two or more substances. Contacting may occur in vivo, ex vivo or in vitro. A sample that is a human or other animal can be contacted with a compound, for example, by therapeutic or prophylactic administration of the compound. A sample that is a tissue, tissue extract or cell can be contacted with a compound, for example, by introduction of the compound into the culture medium. A sample that is a fluid, such as extracellular medium, can be contacted with a compound, for example, by admixing the compound with the fluid.

The screening methods and therapeutic methods described herein involve the use of compounds. As interchangeably used herein, the term "compound(s)" or "agent(s)," in connection with binding to or modulating the activity of a mutant IDE, includes any biomolecule such as a peptide, polypeptide, peptidomimetic, saccharide, fatty acid, steroid, purine, pyrimidine, nucleic acid, derivative or analog thereof, and any such molecules in combination. Such biomolecules can be substantially purified, or can be present in a mixture, such as a cell extract or supernate. The terms "compound(s)" or "agent(s)" further includes synthetic or natural chemical compounds, such as simple, small molecules or complex organic or inorganic molecules, metal-containing compounds, and the like. Also included are known pharmacological compounds, which optionally can be subjected to directed or random chemical modifications, such as acylation, alkylation, esterification, amidation, etc., to produce structural analogs. Test compounds or agents suitable for use in the invention can optionally be contained in compound libraries. Methods for producing compound libraries by random or directed synthesis of a wide variety of organic compounds and biomolecules are known in the art, and include expression of randomized oligonucleotides and oligopeptides. Methods of producing natural compounds in the form of bacterial, fungal, plant and animal extracts are also known in the art. Additionally, synthetically produced or natural compounds and compound libraries can be readily modified through conventional chemical physical and biochemical means to produce combinatorial libraries. Compound libraries are also available from commercial sources.

In certain embodiments, the compounds or agents are steroids, or steroid analogs. As used herein, the term "steroid" refers to structural derivatives of cholesterol or of retinoic acid, which generally contain the same cyclopentanophenanthrene ring as cholesterol or contain the core structure of Vitamin D. The term "steroid" includes all human, mammalian, other vertebrate, insect and plant steroids, as well as synthetic steroids. Major classes of mammalian steroid hormones include progestagens (progestational hormones), glucocorticoids (anti-stressing hormones), mineralcorticoids (Na+ uptake regulators), androgens (male sex hormones), and estrogens (female sex hormones). Exemplary steroids include pregnenolone, estrogen (e.g. 17 beta-estradiol), aldosterone, testosterone, androstenedione, progesterone, cortisol, deoxycortisol, corticosterone, dehydroepiandosterone, calcitriol, ecdysone and vitamin D.

In another aspect, the present invention relates to a diagnostic kit which includes (a) a probe for detecting the mutations of IDE at any of amino acid residues 332, 339, 341, 359, 360, 361, 374, 429, 609, 898, 899 or 901 of SEQ ID NO:1 or SEQ ID NO:2 or variants thereof.

In one aspect of the invention, a diagnostic kit may comprise a first container containing a nucleic acid probe that hybridizes under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridized RNA. In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease associated with IDE such as Alzheimer's disease or diabetes.

In another aspect, the present invention relates to an antibody which binds to a mutant insulin degrading enzyme (IDE) having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence, but does not bind to an IDE whose amino acid sequence consists of the sequence set fort in SEQ ID NO: 1 or SEQ ID NO:2.

The antibodies may be of any suitable source, e.g. monoclonal, polyclonal, chimeric, bispecific, single-chain or fragments thereof. Antibody fragments include, but are not limited to. Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals, or derived from phage or ribosome display libraries. Preferably, the antibodies are human, murine (e.g. mouse or rat), donkey, rabbit, goat, guinea pig, camel, horse, or chicken. The antibodies of the invention may be monospecific, bispecific, trispecific or of greater multispecificity.

The antibodies may be labeled in any suitable manner, thus allowing for detection in a suitable assay.

Subtraction methods for the isolation of antibodies which bind to a mutant IDE having an amino acid sequence that is at least 90% identical to SEQ ID NO:1 over its entire length and has at least one amino acid substitution at any of amino acid residues 332, 339, 341, 359, 360, 361, 374, 429, 609, 898, 899 or 901 of the sequence, but does not bind to an IDE whose amino acid sequence consists of the sequence set fort in SEQ ID NO: 1 or SEQ ID NO:2 are well known in the art.

Further aspects and advantages of the present invention will be disclosed in the following examples, which should be considered as illustrative only, and do not limit the scope of this application.

Example 1

Anion Activation Site of Insulin-Degrading Enzyme

Insulin-degrading enzyme (IDE) (insulysin) is a zinc metallopeptidase that metabolizes several bioactive peptides, including insulin and the amyloid β peptide. IDE is an unusual metallopeptidase in that it is allosterically activated by both small peptides and anions, such as ATP. Here, it is shown that the ATP binding site is located on a portion of the substrate binding chamber wall arising largely from domain 4 of the four-domain IDE. Two variants having residues in this site mutated, $IDE^{K898A,K899A,S901A}$ and $IDE^{R429S}$, both show greatly decreased activation by the polyphosphate anions ATP and PPPi.

$IDE^{K898A,K899A,S901A}$ is also deficient in activation by small peptides, suggesting a possible mechanistic link between the two types of allosteric activation. Sodium chloride at high concentrations can also activate IDE. There are no observable differences in average conformation between the IDE-ATP complex and unliganded IDE, but regions of the active site and C-terminal domain do show increased crystallographic thermal factors in the complex, suggesting an effect on dynamics. Activation by ATP is shown to be independent of the ATP hydrolysis activity reported for the enzyme. In this Example, it is also shown that $IDE^{K898A,K899A,S901A}$ has reduced intracellular function relative to unmodified IDE, consistent with a possible role for anion activation of IDE activity in vivo. Together, the data indicates a model in which the binding of anions activates by reducing the electrostatic attraction between the two halves of the enzyme, shifting the partitioning between open and closed conformations of IDE toward the open form.

Experimental Procedures:

Preparation of IDE Mutants— residues 41-1019 of Rat IDE (SEQ ID NO:1, FIG. 12), bearing the mutations K898A,K899A,S901A ($IDE^{K898A,K899A,S901A}$) or R429S ($IDE^{R429S}$) were prepared from the pFastBac HTb-IDE plasmid (Song et al., *Journal of Biologial Chemistry* 278, 49789-49794 (2003); Song et al., *Journal of Biological Chemistry* 280, 17701-17706 (2005), the disclosures of which are incorporated by reference in their entireties.) using the QuikChange mutagenesis kit (Stratagene). Primers used for mutagenesis are listed below with the base changes in bold and underlined:

1. K898, K899 and S901 changed to alanine—
IDE$^{K898A,K899A,S901A}$.

```
K898A:
Forward
                                  (SEQ ID NO: 4)
5'-CGACTCGACAAACCAGCGAAACTCTCTGCAGAG-3'

Reverse
                                  (SEQ ID NO: 5)
5'-CTCTGCAGAGAGTTTCGCTGGTTTGTCGAGTCG-3'

K899A:
Forward
                                  (SEQ ID NO: 6)
5'-CTCGACAAACCAGCGGCACTCTCTGCAGAGTGC-3'

Reverse
                                  (SEQ ID NO: 7)
5'-GCACTCTGCAGAGAGTGCCGCTGGTTTGTCGAG-3'

S901A:
Forward
                                  (SEQ ID NO: 8)
5'-AAACCAGCGGCACTCGCTGCAGAGTGCGCGAAG-3'

Reverse
                                  (SEQ ID NO: 9)
5'-CTTCGCGCACTCTGCAGCGAGTGCCGCTGGTTT-3'
```

2. Arg429 converted to serine—IDE$^{R429S}$.

```
R429S:
Forward
                                  (SEQ ID NO: 10)
5'-TTTAAAGATAAAGAGAGCCCACGAGGCTACACA-3'

Reverse
                                  (SEQ ID NO: 11)
5'-TGTGTAGCCTCGTGGGCTCTCTTTATCTTTAAA-3'
```

Bacmid and virus production were as discussed previously (Song et al., *Journal of Biologial Chemistry* 280, 17701-17706 (2005), Song et al., *Journal of Biological Chemistry* 276, 1152-1155 (2001)).

Purification of IDE—

IDE and the IDE$^{K898A,K899A,S901A}$ and IDE$^{R429S}$ mutants were expressed as hexahistidine fusion proteins in Sf9 cells and purified on a HIS-select Ni-Affinity Gel column (Sigma) as previously described (Song et al., *Journal of Biological Chemistry* 280, 17701-17706 (2005), Song et al., *Journal of Biological Chemistry* 276, 1152-1155 (2001), the disclosures of which are incorporated by reference in their entireties). Purity was estimated by SDS PAGE gel analysis and protein concentration was determined using the Commasssie Blue Reagent with BSA as a standard.

Crystallization of IDE in the Presence of ATP—

Co-crystallization of wild type IDE and ATP was performed using IDE at 8 mg/ml in 50 mM Tris 7.4, 1 mM DTT, 50-100 mM NaCl, 5 mM ATP and 1 mM EDTA. The enzyme was maintained for 4 days under the above conditions before being used for crystallization trials employing the sitting drop vaporization method with CompactClover plates (Emerald Biosystems). EDTA was used primarily to sequester any free Mg$^{2+}$, which has been shown to reduce activation by ATP (Song et al., *Journal of Biological Chemistry* 279, 54216-54220 (2004); Yao et al., *Archives of Biochemistry and Biophysics* 451, 175-181 (2006)). The protein/ATP solution was mixed 1:1 with well solution containing 100 mM sodium citrate 6.5, 100 mM ammonium acetate, and 20% PEG 4000, and crystals were grown at 22° C., usually accompanied by heavy precipitation. Crystals were dehydrated (Heras et al., *Acta Crystallogr. D Biol. Crystallogr.* 61, 1173-1180 (2005)) by a brief (1-5 second) transfer to 50% PEG 4000 prior to flash cooling in liquid nitrogen (Rodgers, D. W. *Methods Enzymol.* 276, 183-203 (1997)).

Data Collection and Structure Determination—

Final data were collected at Beamline-X4C of the National Synchrotron Light Source at Brookhaven National Laboratory and the data processed using HKL2000 (Otwinowski et al., *Methods Enzymol.* 276, 307-326 (1997)). The structure of IDE crystallized with ATP was determined by molecular replacement with PHASER (McCoy et al., *J. Appl. Cryst.* 40, 658-674 (2007)) using the native rat IDE coordinates and refined using REFMAC5 within CCP4 (Collaborative Computational Project, Number 4, 1994) with subsequent model building performed using COOT (Emsley et al., *Acta Crystallogr. D Biol. Crystallogr.* 60, 2126-2132 (2004)). Water molecules were assigned using PHENIX (Adams et al., *Acta Crystallogr. D Biol. Crystallogr.* 58, 1948-1954 (2002)), CCP4, and COOT. The quality of the final structure was analyzed using the Molprobity server (Lovell et al., *Proteins: Structure, Function, and Genetics* 50, 437-450 (2003)), and figures were made using PyMol. (W. L. DeLano, The PyMOL Molecular Graphics System, 2002, www.pymol.org). Crystallographic data collection and refinement statistics are summarized in Table 1.

TABLE 1

Crystallographic summary of data collection and structure determination for the IDE-ATP complex crystal structure.
Data Collection and Structure Refinement

|  | IDE-ATP |
| --- | --- |
| Resolution (Å) | 50.0-2.27 |
| Space group | C2 |
| Mol/ASU | 1 |
| a (Å) | 115.0 |
| b (Å) | 70.7 |
| c (Å) | 114.1 |
| α° | 90.00 |
| β° | 92.63 |
| γ° | 90.00 |
| λ (Å) | 0.9794 |
| Completeness (%)* | 92.0 (88.7) |
| Redundancy* | 3.3 (2.7) |
| $R_{sym}$* | 0.09 (0.48) |
| I/σ* | 11.0 (1.9) |
| R/Rfree | 0.22/0.27 |
| Bond lengths (Å) | 0.007 |
| Bond angles (°) | 1.04 |
| # water molecules | 226 |
| Ramachandran favored (%) | 96.8 |
| Ramachandran outliers (%) | 0.0 |

*indicates the statistics for the last resolution shell (2.33-2.27 Å) shown in parentheses.

Enzyme Activity Assay—

IDE activity was determined by measuring the increase in fluorescence that occurs when the enzyme cleaves the internally quenched fluorogenic substrate Abz-GGFLRKHGQ-EDDnp (SEQ ID NO:3) at the R—K bond (Song et al., *Journal of Biologial Chemistry* 276, 1152-1155 (2001)). The reaction was followed on a SpectraMax Gemini XS fluorescence plate reader using an excitation and emission wavelengths of 318 nm and 419 nm, respectively. Initial velocities were determined using SoftMax Pro 4.0 and kinetic constants calculated using GraphPad Prism 4.0. ATPase activity was measured by following Pi release with acid-molybdate as described by Harder et al. (Harder et al., *Biochemical Journal* 298 (Pt 2), 395-401 (1994)).

TNP-ATP Fluorescence Measurements—

TNP-ATP [2',3'-O-(2,4,6-Trinitrophenyl)adenosine-5'-triphosphate] fluorescence was monitored at excitation and emission wavelengths of 403 nm and 547 nm, respectively, using a Perkin-Elmer LS55 Luminescence Spectrometer at 20±0.1° C. TNP-ATP (Molecular Probes, Inc.) as supplied was diluted to 4 mM with 50 mM Tris-HCl, pH 7.4, and added to achieve the indicated concentrations.

IDE Activity Assay in Yeast—

Wild type IDE and $IDE^{K898A,K899A,S901A}$ activities were compared in *Saccharomyces cerevisiae* using both a serial dilution mating test and a spot halo assay as described previously (Kim et al., *Journal of Biologial Chemistry* 280, 27481-27490 (2005), Alper et al., *Biochemical Journal* 398, 145-152 (2006)).

The assays take advantage of the ability of IDE, in lieu of the yeast M16 metallopeptidases Ax11p and Step 23p, to participate in the proteolytic maturation of yeast a-factor mating pheromone. In the mating test, 1H1793 cells [MATα lys1 (Michaelis et al, *Mol. Cell. Biol.* 8, 1309-1318 (1988))] were mixed with decreasing numbers of strain Y272 cells (MATa trp1 leu2 ura3 his4 can1 ax11::LEU2 step23::LEU2) bearing expression plasmids encoding IDE (pWS839; 2μ URA3 $P_{PGK}$-6×HISn::TEV::$IDE_{(41-1019)}$), $IDE^{K898A,K899A,S901A}$ (pWS841; 2μ URA3 $P_{PGK}$-6×HISn:: TEV::$IDE_{(41-1019)}$K898A,K899A,S901A), or an empty expression vector [pRS316 (Sikorski et al., *Genetics* 122, 19-27 (1989))]. The initial ratio of MATa to MATα cells was 9:1 in a 100 μl volume, with subsequent mixtures having sequentially 10-fold less MATα cells. Portions of mating mixtures (10 μl) were spotted on minimal media. Growth of diploid colonies, indicative of mating, was scored 3 days after incubation of plates at 30° C. For the halo assay, yeast bearing the expression plasmids listed above were cultured in 5 ml selective media for 3 days at 30° C. in 15 ml conical polypropylene tubes, which adsorb a-factor on their walls. The adsorbed a-factor was extracted by voiding the contents of the culture, washing the tubes several times with deionized water, and desorbing a-factor with methanol. Recovered a-factor samples were dried by speed-vac, and samples reconstituted in methanol (50 μl). Two-fold serial dilutions of the samples were prepared in YEPD liquid media, and a portion (2 μl) of each dilution spotted onto a lawn of RC757 cells [MATα lys1 sst2-1 (Chan et al., *Mol. Cell. Biol.* 2, 11-20 (1982))] that had been spread on YEPD solid media; RC757 yeast undergo a strong growth arrest phenotype in the presence of a-factor (Marcus et al., *Mol. Cell. Biol.* 11, 1030-1039 (1991)). Halo formation was allowed to proceed for 18 hr at 30° C. Results of mating tests and halo assays were recorded by scanning plates with a Microtek flatbed scanner and importing digitized images into Photoshop and PowerPoint.

Construction of Yeast Expression Vectors Encoding IDE— pWS839 and pWS841 were created by plasmid-based PCR directed recombination (Oldenburg et al., *Nucleic Acids Research* 25, 451-452 (1997)). In brief, the IDE encoding sequences were amplified by PCR from the pFastBac HTb vectors described above (IDE and $IDE^{K898A,K899A,S901A}$) such that the ends of the PCR products contained the desired coding region and 39 basepair extensions on either end that were homologous to the expression vector [pSM703 (Zhang et al., *Mol. Biol. Cell.* 12, 1303-1314 (2001)), 2μ URA3 $P_{PGK}$] at sites on opposite sides of the polylinker. The PCR product was co-transformed into Y272 yeast along with pSM703 that had been digested with XmaI and NotI. Plasmids were isolated from yeast colonies surviving selection and screened for the presence of an appropriate insert by restriction digest analysis.

Preparation of Yeast Cell Extracts and Immunoblotting—

Yeast extracts for immunoblot analysis were generated by alkaline lysis and TCA precipitation as described previously (Fujimura-Kamada et al., *J. Cell. Biol.* 136, 271-28544 (1997)). The recovered protein precipitates were resuspended in hot (100° C.) urea sample buffer (250 mM Tris, pH 8.0, 6 M urea, 4% SDS, and 0.01% bromophenol blue) and clarified by centrifugation before use (16,000×g, 1 min). An equivalent percentage amount of each sample was subject to SDS-PAGE followed by immunoblot analysis using an IDE-specific antibody, an appropriate secondary antibody, and chemiluminescence detection methods (BM Chemiluminescence Blotting Substrate, Roche).

IDE-ATP Complex Crystal Structure:

Previous studies have shown that the polyphosphate anions ATP and PPP, act as heterotropic activators of IDE towards the hydrolysis of small peptides including the fluorogenic substrate Abz-GGFLRKHGQ-EDDnp (SEQ ID NO:3) (Song et al., *Journal of Biological Chemistry* 279, 54216-54220 (2004), Song et al., *Journal of Biological Chemistry* 276, 1152-1155 (2001)). In order to determine the interactions important for ATP binding in IDE, we crystallized rat IDE in the presence of ATP and determined the structure of the enzyme at 2.27 Å by molecular replacement using our previously determined native rat IDE coordinates. A difference electron density map revealed the presence of two bound ligands. The first region of strong positive difference density was at the previously described distal binding site (Shen et al., *Nature* 443, 870-874 (2006)). Attempts to model in the triphosphate moiety of ATP into the positive electron density at this site resulted in several unfavorable contacts with the enzyme. We have found that cleavage of the N-terminal His-tag from inactive IDE leads to binding of the cleaved peptide at the distal site, and a three-residue poly-alanine peptide modeled into this site accounted for most of the observed electron density.

The second ligand site is located on the inner surface of domain 4 (the loop between helices α31 and α32) near the interfaces with domains 2 and 3. The observed difference electron density was consistent with bound ATP, and a model for the ligand was placed at this site (FIG. 1). Electron density for the adenine ring of the ATP molecule was absent, indicating that this portion of the molecule is disordered. This observation is consistent with previous studies suggesting that ATP binding occurs primarily if not exclusively through the triphosphate moiety (Song et al., *Journal of Biological Chemistry* 279, 54216-54220 (2004), Yao et al., *Archives of Biochemistry and Biophysics* 451, 175-181 (2006)).

Figure 2:
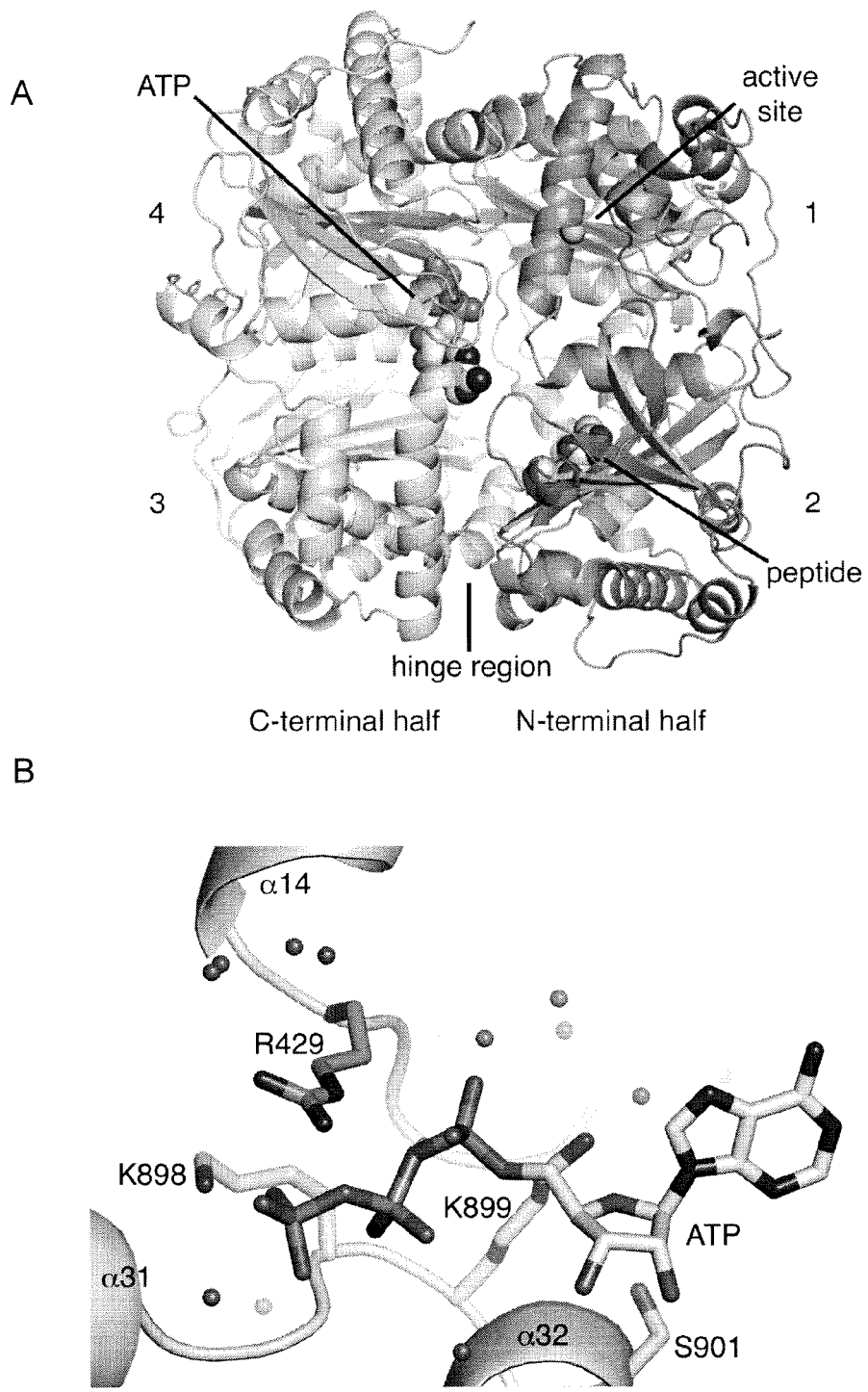
FIG. 2 depicts an overview of the IDE structure and details of the ATP binding site (i.e., allosteric site) in this enzyme. In panel A, the backbone trace of IDE crystallized in the presence of ATP is shown in a ribbons representation with the four structurally related domains numbered and the N- and C-terminal halves of the molecule colored in cyan (right) and yellow (left), respectively. The expected position of the active site zinc ion is shown as a sphere, but the metal is absent in the crystal structure. The region believed to act as a hinge for a conformational change is also indicated. Modeled ATP and a 3-mer polyalanine peptide are shown in a space filling representation and indicated by labels. In panel B, the proposed ATP binding site is shown with selected side chains in a stick representation and ordered water as red spheres. ATP modeled into difference density present in the site is also show in stick representation.

The model of ATP binding indicates several potential interactions with the enzyme (FIG. 2). The side chains of residues R429, K898, K899, S901 are in position to make hydrogen bond interactions with the modeled ATP ligand. Also the amide nitrogen of K898 is well positioned to hydrogen bond with the phosphate groups in the model. R429 is the only domain 2 residue that can contribute to ATP binding. It is somewhat analogous to an arginine finger found in some other GTP and ATP hydrolyzing proteins, where the charge on the guanidinium group stabilizes additional negative charge development during the transition state of ATP hydrolysis. It should be noted that the millimolar affinity of IDE for ATP/polyphosphates suggests that these residues do not make strong contacts with the bound ligand.

Figure 3:
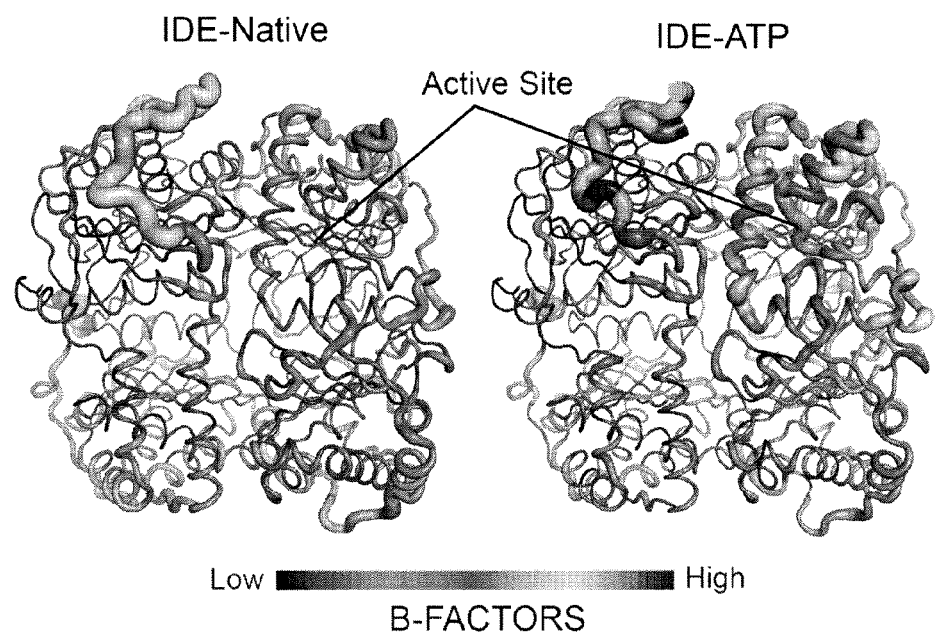
FIG. 3 shows IDE thermal factors in absence or presence of ATP. Relative thermal factors for C-alpha atoms are color coded as indicated for unliganded IDE and IDE crystallized in the presence of ATP. The thickness of the backbone worm also indicates the relative thermal factors.

A structural alignment of the IDE-ATP complex with the native IDE crystal structure did not reveal any significant changes in average conformation at the ATP binding site. However, a comparison of the thermal factors for native IDE and the IDE-ATP crystal structures (which are essentially isomorphous and were determined at nearly the same resolution) suggest a global change in dynamics of IDE upon binding ATP (FIG. 3). In particular, higher thermal factors were observed for many of the residues within the catalytic domain of IDE. The average thermal factors on all atoms of the catalytic domain (residues 42-285) of IDE is 29.5 Å$^2$ as compared to a value of 49.9 Å$^2$ for the same residues of IDE-ATP.

Figure 4:
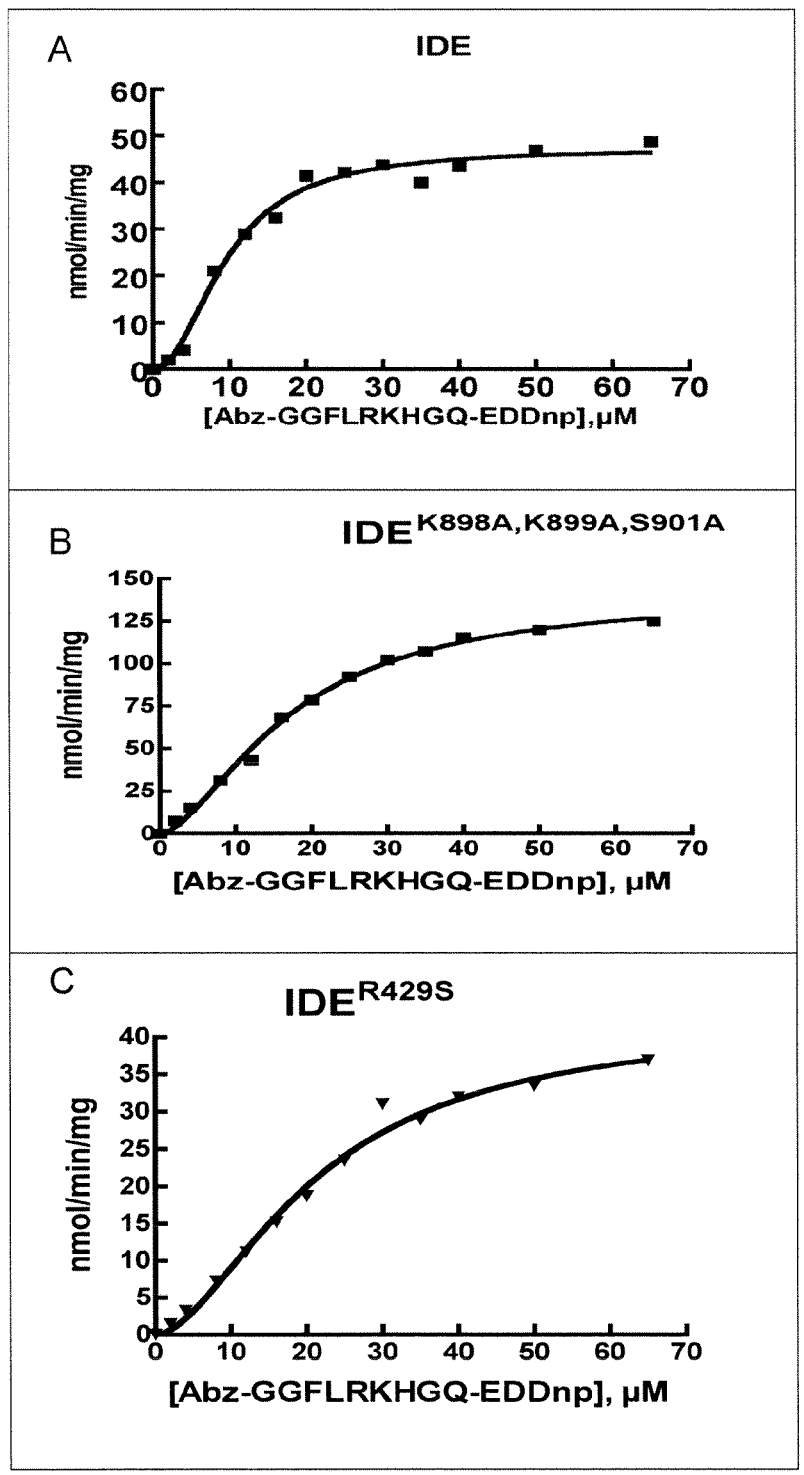
FIG. 4 shows the comparison of the kinetics of IDE and IDE containing ATP binding site mutations using Abz-GG-FLRKHGQ-EDDnp (SEQ ID NO:3) as the substrate. Reactions were conducted in 50 mM Tris-HCl, pH 7.4. Panel A shows the kinetics of unmodified IDE (0.5 µg). Panel B shows the kinetics of $IDE^{K898A,K899A,S901A}$ mutant (0.5 µg). Panel C shows the kinetics of $IDE^{R429S}$ mutant (1.0 µg).

Mutagenesis and Biochemical Analysis of the ATP Binding Site of IDE:

Site-directed mutagenesis was used to eliminate possible binding interactions identified in the crystal structure. Two mutant forms of IDE were generated, the first with mutations K898A, K899A, and S901A (IDE$^{K898A,K899A,S901A}$) and the second with the single mutation R429S (IDE$^{R429S}$). With the synthetic substrate Abz-GGFLRKHGQ-EDDnp (SEQ ID NO:3), both mutants retained the sigmoidal substrate versus velocity response observed with wild type IDE, which is characteristic of allosteric homotropic activation (FIG. 4). Hill coefficients of 1.7 were calculated for both mutants. The IDE$^{K898A,K899A,S901A}$ mutant showed a 3-fold increase in k$_{cat}$ relative to wild-type IDE, while IDE$^{R429S}$ had essentially the same k$_{cat}$ as wild type IDE (Table 2). Both mutants had a roughly 2 fold higher K$_M$ than wild-type IDE.

TABLE 2

Summary of kinetic properties of IDE, IDE$^{R429S}$, and IDE$^{K898A,K899A,S901A}$ with Abz-GGFLRKHGQ-EDDnp as a substrate.

|  | IDE | IDE$^{R429S}$ | IDE$^{K898A,K899A,S901A}$ |
| --- | --- | --- | --- |
| Vmax (nmol/min/mg) | 47.2 ± 1.7 | 42.3 ± 3.2 | 140.8 ± 5.5 |
| k$_{cat}$ (min$^{-1}$) | 5.2 ± 0.2 | 4.7 ± 0.3 | 15.5 ± 0.6 |
| K$_m$ (mM) | 9.6 ± 0.7 | 21.3 ± 2.4 | 17.3 ± 1.0 |
| Hill Coefficient | 2.1 ± 0.3 | 1.7 ± 0.2 | 1.7 ± 0.1 |

Figure 5:
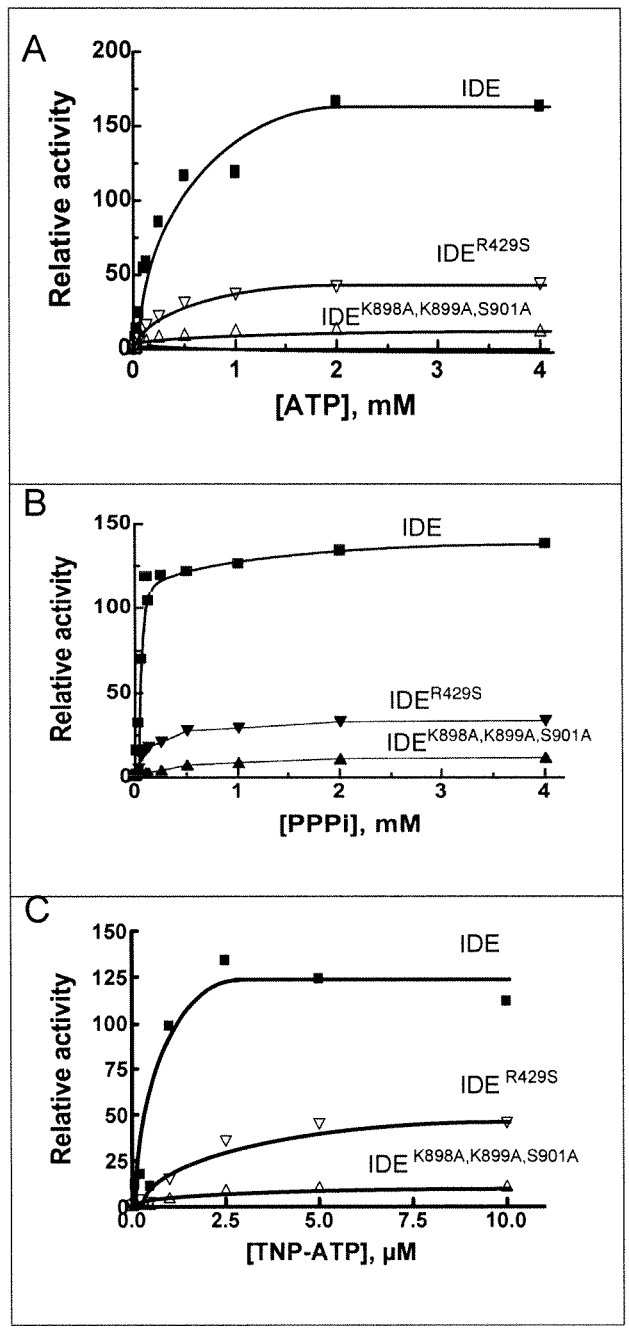
FIG. 5 shows the effect of ATP binding site mutations on the ability of ATP, PPPi and TNP-ATP to increase the rate of Abz-GGFLRKHGQ-EDDnp (SEQ ID NO:3) hydrolysis. Activity was determined in 50 mM Tris-HCl, pH 7.4 with 10 µM Abz-GGFLRKHGQ-EDDnp (SEQ ID NO:3) as substrate at the indicated concentrations of ATP (panel A), PPPi (panel B) or, TNP-ATP (panel C). Each reaction contained 0.5 µg of enzyme.
Figure 6:
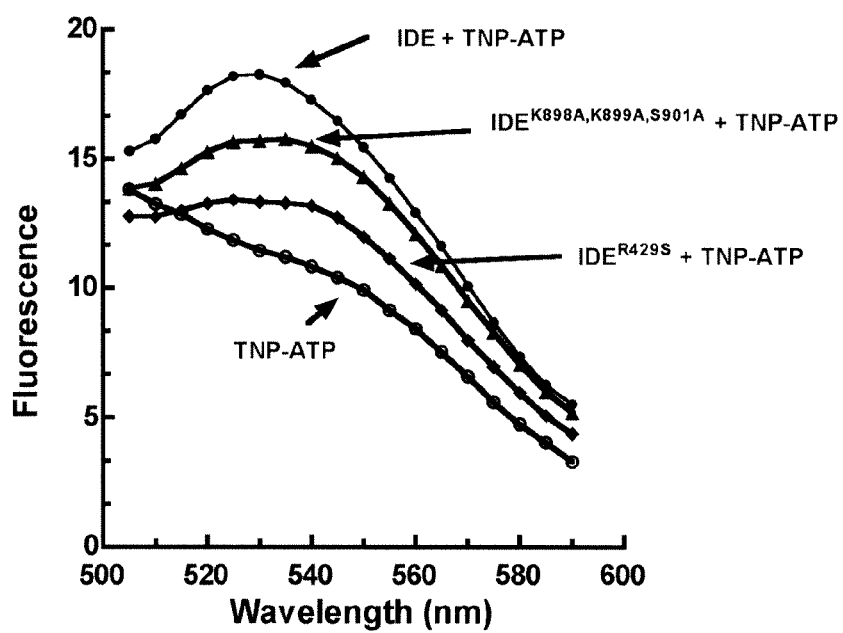
FIG. 6 shows the binding kinetics of TNP-ATP to IDE and ATP binding site mutants. Fluorescence emission spectra were recorded on a Perkin-Elmer LS 55 Luminescence spectrometer with 1.5 µM of IDE, $IDE^{R429S}$ or $IDE^{K898A,K899A,S901A}$ in 50 mM Tris-HCl, pH 7.4 with 10 µM TNP-ATP. Fluorescence spectra were recorded with a λexc=403 nm.

Significantly, the ability of ATP to activate both IDE mutants was greatly reduced relative to the wild type enzyme (FIG. 5). ATP activates wild type IDE roughly 150 fold with Abz-GGFLRKHGQ-EDDnp (SEQ ID NO:3) as a substrate. However, the level of IDE$^{R429S}$ activation is only about 15% of the wild type value, and there is even less activation of IDE$^{K898A,K899A,S901A}$ by ATP. Similar results were observed with PPP, and the fluorescent analog TNP-ATP. Both mutants also show alterations in the fluorescence increase at 530 nm associated with TNP-ATP binding (FIG. 6). IDE$^{R429S}$ and IDE$^{K898A,K899A,S901A}$ have a lower fluorescent yield and a shift in the fluorescence maximum to a longer wavelength relative to wild type IDE. These kinetic and analog binding results were consistent with an alteration in the nature of the ATP/polyanion binding site in the mutant versions of IDE.

Figure 7:
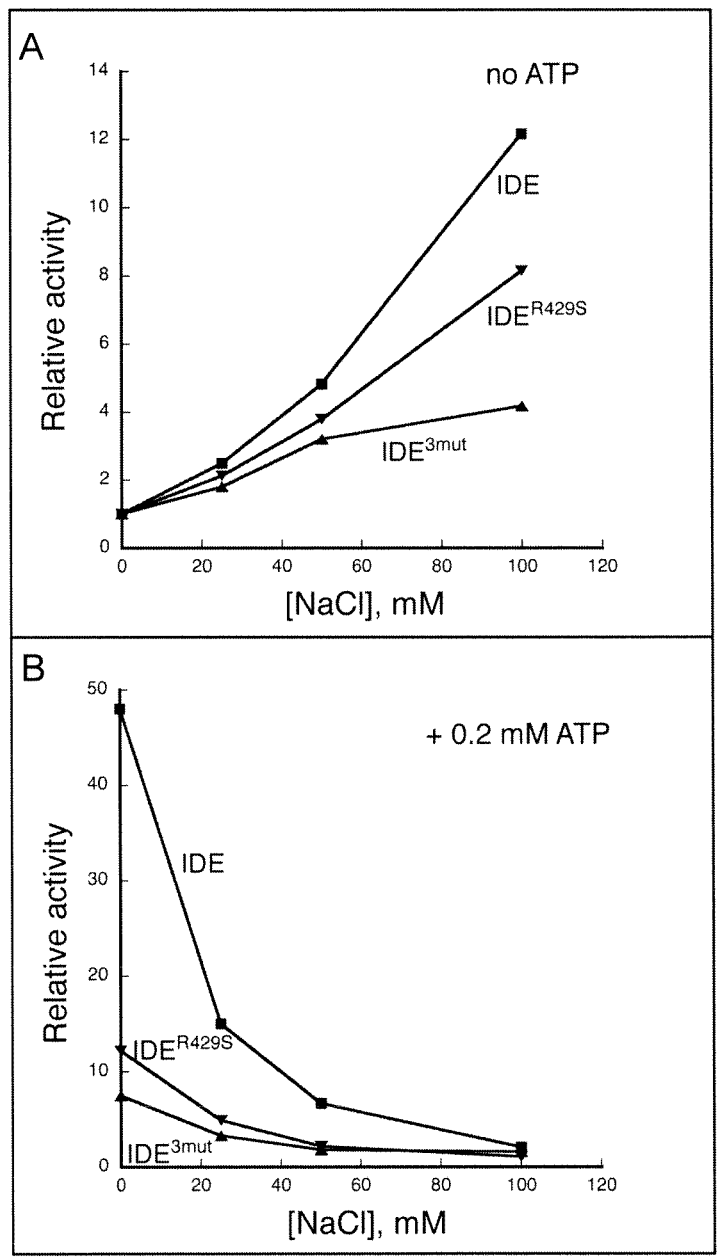
FIG. 7 shows the effect of NaCl on IDE and Abz-GGFL-RKHGQ-EDDnp (SEQ ID NO:3) hydrolysis and activation by ATP. Activity was determined in 50 mM Tris-HCL, pH 7.4 with 10 µM Abz-GGFLRKHGQ-EDDnp (SEQ ID NO:3) as substrate for IDE, $IDE^{K898A,K899A,S901A}$, or $IDE^{R429S}$ either without (panel A) or with 0.2 mM ATP (panel B).

It was further found that the activity of wild type IDE and the two mutants with the Abz-GGFLRKHGQ-EDDnp (SEQ ID NO:3) substrate was increased with increasing NaCl concentration (FIG. 7A). It was observed that increasing the salt concentration correspondingly reduced the ability of ATP to activate the enzyme (FIG. 7B). At an ATP concentration (0.2 mM) producing approximately one third of the maximal activation of wild type IDE, heterotropic activation was progressively reduced to below measurable levels over the NaCl concentration range of 0-100 mM. The effects of increasing salt concentration on enzyme activity were suggestive of an electrostatic mechanism for polyanion activation, which is discussed more fully below.

Figure 8:
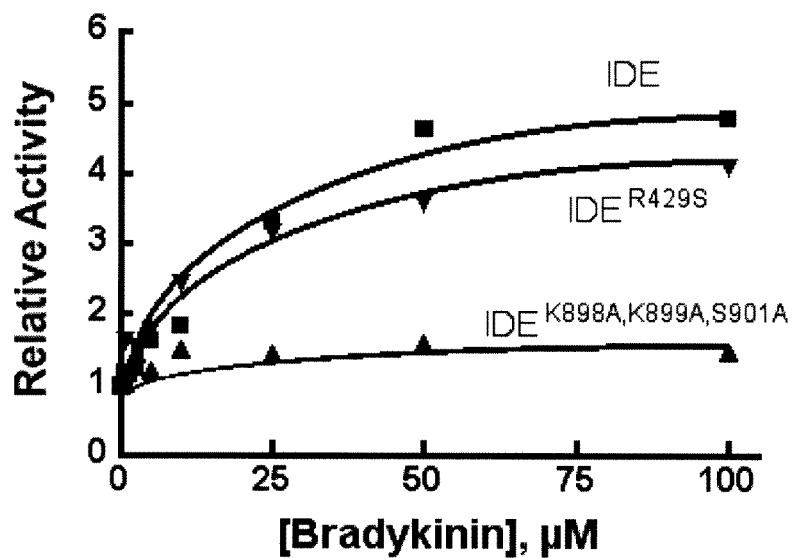
FIG. 8 shows the effect of bradykinin on Abz-GGFL-RKHGQ-EDDnp (SEQ ID NO:3) hydrolysis by IDE, $IDE^{K898A,K899A,S901A}$, or $IDE^{R429S}$. Activity was determined in 50 mM Tris-HCl, pH 7.4 with 10 µM Abz-GGFLRKHGQ-EDDnp (SEQ ID NO:3) as substrate and indicated concentrations of bradykinin. Reactions contained 0.5 µg of protein.

It has previously been shown that small peptides like bradykinin can act as activators of Abz-GGFLRKHGQ-EDDnp (SEQ ID NO:3) hydrolysis, and interactions between peptide and polyanion activation have been suggested (Song et al., *Journal of Biologial Chemistry* 278, 49789-49794 (2003)). We thus determined the effect ATP binding site mutations would have on the ability of bradykinin to increase the rate of Abz-GGFLRKHGQ-EDDnp (SEQ ID NO:3) hydrolysis. Similar rates were observed for IDE$^{R429S}$ and wild type IDE, while the observed rate for IDE$^{K898A,K899A,S901A}$ was significantly reduced, suggesting that ATP and peptide dependent activation may be mechanistically linked (FIG. 8).

Figure 9:
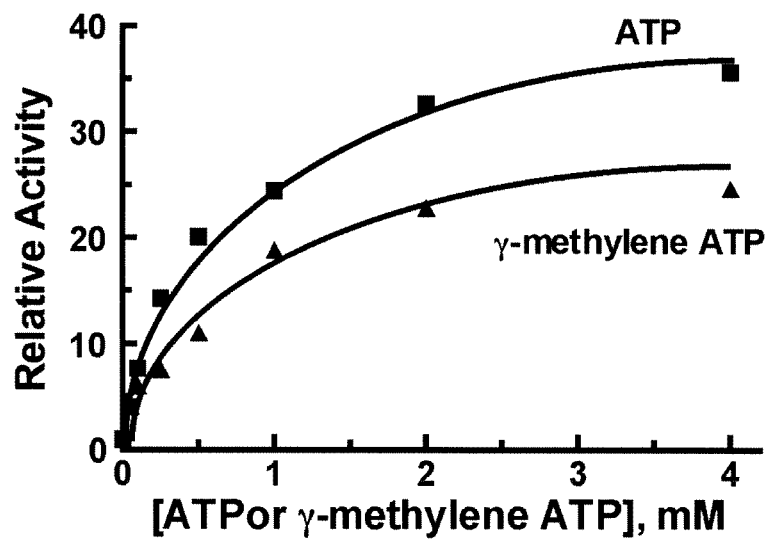
FIG. 9 shows the ability of γ-methylene-ATP versus ATP to increase the IDE-dependent hydrolysis of Abz-GGFL-RKHGQ-EDDnp (SEQ ID NO:3). Activity was determined in 50 mM Tris-HCl, pH 7.4 with 10 µM Abz-GGFLRKHGQ-EDDnp (SEQ ID NO:3) as substrate and indicated concentrations of ATP or γ-methylene-ATP. Reactions contained 0.1 µg of protein.

IDE has been reported to exhibit ATPase activity (Del Carmen Camberos et al., *Exp. Biol. Med.* (*Maywood*) 232, 281-292 (2007)). Thus the question arises as to whether activation of IDE by ATP is coupled to its hydrolysis. We found that the nonhydrolyzable ATP analog γ-methylene ATP is able to activate Abz-GGFLRKHGQ-EDDnp (SEQ ID NO:3) hydrolysis nearly as well as ATP (FIG. 9), demonstrating that ATP hydrolysis is not necessary for IDE activation. IDE-dependent ATPase activity was estimated to be less than 1 nmol/min/mg IDE using 1 mM ATP as substrate, and this rate did not change in the presence of Abz-GGFLRKHGQ-EDDnp (SEQ ID NO:3) substrate. The much higher rate of peptide cleavage (see Table 2) also supports the conclusion that ATPase activity is not coupled to activation.

Figure 10:
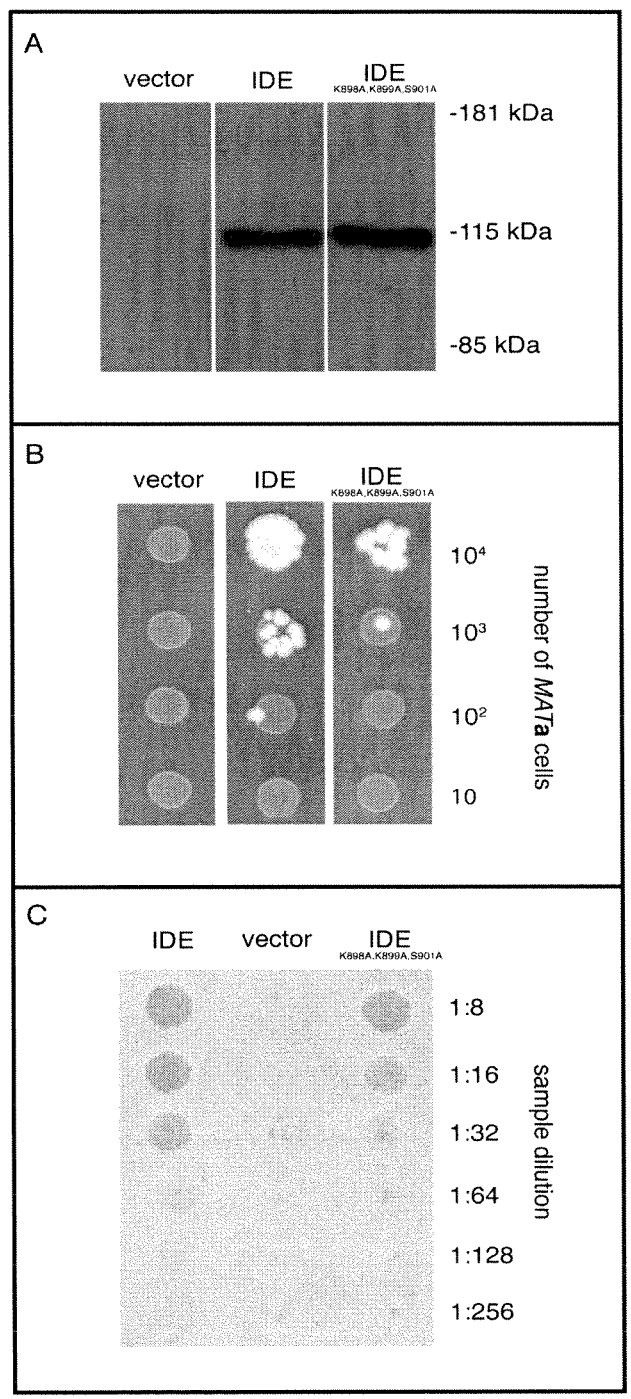
FIG. 10 shows the activity of wild type IDE and the ATP binding-site mutant $IDE^{K898A,K899A,S901A}$ in the yeast *Saccharomyces cerevisiae*. Panel A depicts immunoblot of yeast-expressed IDE and $IDE^{K898A,K899A,S901A}$. Equivalent percentage amounts of total cellular extracts from yeast containing an empty expression vector or plasmids encoding IDE or the $IDE^{K898A,K899A,S901A}$ mutant were analyzed by SDS-PAGE and immunoblotting using an IDE-specific antibody. Panel B shows a mating test for IDE activity. An excess of MATa yeast were mixed with decreasing numbers of MATa cells deficient for Axl1p and Step 23p that were transformed with either an empty expression vector or a vector encoding IDE or $IDE^{K898A,K899A,S901A}$ as indicated. Mating, which leads to colony growth, is dependent on production of mature a-factor pheromone by plasmid-encoded IDE. Panel C shows a spot halo assay for a-factor production. Concentrated samples of a-factor recovered from yeast bearing the indicated expression vector were spotted at the indicated dilutions on a lawn of RC757 MATa cells, which undergo growth arrest upon exposure to a-factor pheromone. The zones of growth arrest are the dark circular regions within the yeast lawn.

Effect of ATP-Binding Site Mutation on the Intracellular Activity of IDE:

An established yeast system for functional studies of IDE (Kim et al., *Journal of Biological Chemistry* 280, 27481-27490 (2005), Alper et al., *Biochemical Journal* 398, 145-152 (2006)) was used to assess the significance of polyphosphate/polyanion activation on IDE activity in a cellular environment. The assay is based on the ability of IDE to support production of mature a-factor mating pheromone in the absence of yeast metallopeptidases (i.e., Axl1p and Step 23p) that normally promote its maturation. When expressed in this yeast system, IDE and the ATP binding-site mutant IDE$^{K898A,K899A,S901A}$ were produced at approximately the same protein levels (FIG. 10A). Wild type IDE, however, promoted mating to a greater extent than IDE$^{K898A,K899A,S901A}$ (FIG. 10B). Similarly, a spot halo assay revealed greater production of a-factor by yeast expressing wild type IDE relative to yeast expressing the ATP binding-site mutant (FIG. 10C). The results indicate that an intact polyphosphate/polyanion binding site is required for maximal IDE activity in yeast, suggesting that heterotropic activation by polyanions influences IDE activity in vivo.

The ATP Binding Site of IDE:

Difference electron density calculated from data collected with IDE crystals grown in the presence of ATP indicates a ligand-binding site located mainly on the inner surface of domain 4 near the interfaces with domains 2 and 3. The binding site, primarily the surfaces of domains 3 and 4 that face the enclosed chamber, carries a positive surface charge, and several basic residues (R429, K898, K899) are in position to interact with bound ATP in the model of the complex. Mutating these residues, as well as S901, in the IDE$^{R429S}$ and IDE$^{K898A,K899A,S901A}$ variants, profoundly disrupts heterotropic activation by ATP. In addition, these mutations affect the electronic environment of the fluorescent trinitrophenyl group of TNP-ATP. Taken together these data show that the site identified by crystallography was indeed the ATP/polyanion binding site.

Figure 11:
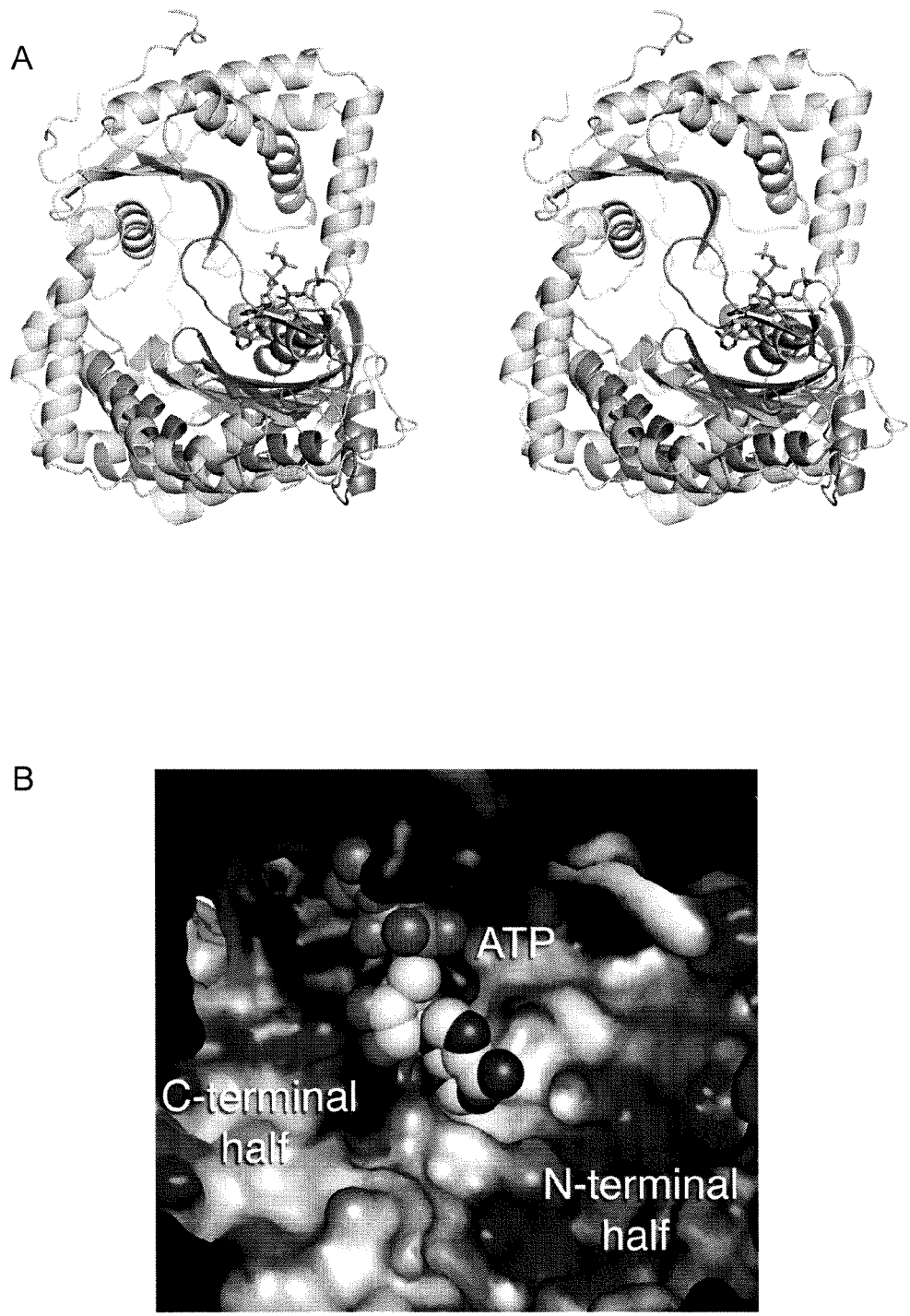
FIG. 11 shows a structural relationship of the IDE ATP/polyanion binding fold to palm domain containing enzymes and surface electrostatics. Panel A shows a stereo view of a ribbons representation of domains 3 and 4 of IDE is shown (cyan or lighter gray in Black & White) superimposed with the C1a domain of adenylyl cyclase (purple or darker gray in B&W; Tesmer et al., 1999; PDB entry 1CJU). ATP ligands for both molecules are shown in stick representation with carbon atom colors matching the corresponding ribbon model. IDE is oriented as viewed from the substrate-binding chamber of the enzyme with domain 4 at the top of the figure. Panel B shows the surface electrostatic potential on the walls of the substrate-binding chamber of IDE. The molecular surface is colored according to electrostatic potential (blue, positive (areas around ATP and C-terminal half); red, negative (areas around N-terminal half)) with modeled ATP shown in a sphere representation and the N-terminal and C-terminal halves of IDE indicated.

A structural similarity search (DaliLite v.3) using domains 3 and 4 of IDE identified a number of structurally related enzymes that have nucleotide substrates (FIG. 11A). In particular, IDE has structural similarity with polymerases and other nucleotidyltransferases, adenylyl cyclase, and GTP cyclohydrolase III, all palm domain-containing enzymes. Importantly, the nucleotide binding positions in these enzymes at least partially overlap the identified ATP binding site in IDE. While the details of binding interactions differ, the similarity of the fold and nucleotide location increases confidence in the IDE polyanion binding assignment and suggests an evolutionary relationship. The presence of R429 near the triphosphate group in the model of bound ATP is reminiscent of arginine fingers observed in some GTPases and ATPases. In many of these enzymes, the arginine residue involved arises from an interacting protein or a subunit not principally involved in nucleotide binding, again an interesting similarity to IDE, in which R429 comes from domain 2 rather than the main ATP-binding domain (domain 4). The data indicates that R429 plays a similar role in stabilizing extra charge development during the transition state in ATP hydrolysis by IDE.

We anticipated that mutating IDE residues in the polyphosphate/polyanion binding site would decrease affinity and thus alter the concentration dependence of activation by ATP. Instead, we found that only the extent of heterotropic activation was affected, while the dependence on ATP concentration was not greatly changed. One possible explanation for this unexpected observation is that the mechanism of activation, but not ATP binding itself, is disrupted in these mutants. This interpretation seems unlikely, however, since the crystallographic and TNP-ATP fluorescence data strongly suggest that the identified site binds ATP. Importantly, the difference electron density could not be interpreted as a conformational change in the enzyme at the identified site. The density for the enzyme itself in that region is strong and unambiguous.

Our observations provide an alternative explanation for the properties of the IDE mutants. The proposed ATP binding site is roughly centered in the positively charged inner surface formed by domains 3 and 4 (FIG. 11B). While ATP binds to this site specifically, giving rise to the observed electron density, it does so with relatively low affinity, only in the millimolar range. There are a number of potential nonspecific sites for ATP/polyanion binding on the positively charged surface surrounding the specific binding site. At the high ATP/polyanion concentrations that result in occupancy at the specific site, at least partial occupancy at sites on the surrounding surface might occur, enhancing IDE activity. In this model, however, binding at the specific site would activate IDE to a greater extent than binding at nonspecific sites. This would account for the sharp decrease in the extent of activation when the specific site is ablated. Activation would still occur, but only to the lower extent supported by binding to the nonspecific sites.

Activation of the wild type enzyme would, in the proposed model, have contributions from polyphosphate/polyanion occupancy at both the specific and nonspecific sites. The nonspecific sites would not be observed by crystallography, since occupancy would be distributed over the surface in different IDE molecules and thus averaged to the noise level of the electron density maps. Also, the orientation of the bound ligand at any particular nonspecific site would vary across the molecules in the crystal, again causing the loss of observable density upon averaging.

The greater activity of wild type IDE over IDE$^{K898A,K899A,S901A}$ in the yeast assays indicated that polyanions are important in determining the level of IDE activity in vivo. Typical intracellular nucleotide concentrations (Beis et al., *Biochemical Journal* 152, 23-32 (1975)) match the observed activation range for IDE, indicating that they may play a significant role in promoting this heterotropic activation in yeast cells. Most nucleotides in the cell are complexed with divalent cations, however, and this may reduce their effectiveness in activating IDE. Other small polyanionic species present in cells (Jones et al., *Mol. Cell. Proteomics* 3, 746-769 (2004)), including inositol and other sugar phosphates, small glycosaminoglycans, and peptides, may contribute as well. It will be of some interest in future work to determine the importance of polyphosphate/polyanion activation in the physiological roles proposed for IDE in mammals.

A Potential Activation Mechanism:

The location of the ATP binding site determined in this work provides a possible mechanism for activation by polyphosphate/polyanion binding. Previous studies by Tang and coworkers (Shen et al., *Nature* 443, 870-8749, 20 (2006), Im et al., *Journal of Biologial Chemistry* 282, 25453-25463 (2007)) have indicated that the proposed hinge-like conformational change necessary for substrate entry/product release is likely rate limiting. In addition, heterotropic activation may occur through a shift in the conformational equilibrium toward the open state of the enzyme, since ATP binding is accompanied by an increase in the hydrodynamic radius of IDE (Song et al., *Journal of Biologial Chemistry* 279, 54216-54220 (2004)). The inner surface of the IDE substrate-binding chamber contributed by domains 3 and 4 carries a strong positive electrostatic potential, while the inner surface contributed by domains 1 and 2 is strongly negative (FIG. 11B). Thus binding of ATP or other polyanions to the positively charged half of the chamber likely reduces the electrostatic attraction between the two chamber walls, increasing the open state population. This electrostatic mechanism is consistent with the activation of IDE by salt, since higher ionic strength would also reduce the electrostatic attraction between the two walls of the binding chamber. It also can explain why IDE$^{K898A,K899A,S901A}$, which reduces the overall charge on the positively charged half of the chamber, shows an approximately 3-fold higher $k_{cat}$ than the wild type enzyme. In addition, the increased thermal motion seen for the catalytic domain in the crystal structure reflects a loosening of the interface between the two halves of IDE. Interestingly, monomeric IDE is not activated by ATP or PPP$_i$, indicating that dimer contacts may be required for the proposed electrostatic activation within each monomer. Alternatively, the dependence on dimerization indicates a more complicated activation mechanism in which an allosteric signal is transmitted from one monomer to its dimer partner.

The lack of polyphosphate/polyanion activation with large IDE substrates such as amyloid β peptides and insulin (Song et al., *Journal of Biologial Chemistry* 279, 54216-54220 (2004)) reflects the ability of the larger substrates to effectively shield electrostatic attraction between the chamber walls. The larger substrates may also block polyphosphate/polyanion binding to the specific site.

The conformation of the structurally related enzyme pitrilysin is of interest regarding the proposed activation mechanism. The two inner chamber walls of this enzyme (PDB accession code 1Q2L) both carry an overall negative surface charge, and the enzyme has been crystallized only in the open conformation that is envisioned to allow substrate biding and product release by IDE. Thus in pitrilysin, repulsion between two negatively charged surfaces likely plays a role in stabilizing an open conformation, just as attraction between two oppositely charges surfaces may stabilize the closed form of IDE. Bacterial pitrilysin is a secreted enzyme localized to the periplasm *Journal of Bacteriology* 149, 1027-1033 (1982)). This difference in environment with the cytosolic IDE, particularly differences in polyphosphate/polyanion concentrations, accounts for the variation in charge on the substrate binding chamber walls.

Possible involvement of R429 in ATP binding seems at first glance incompatible with a mechanism that promotes the open enzyme conformation. That residue arises from domain 2, which would move away from the main binding site on domain 4 as the enzyme adopts the open conformation. The interaction with R429 is weak and is more than compensated for by the reduction in electrostatic attraction resulting from ATP binding. In that sense, it is important to note that mutating this residue reduced activation less than the mutations in the triple IDE mutant. Interestingly, unlike IDE$^{K898A,K899A,S901A}$, IDE$^{R429S}$ did not show a change in base activity relative to wild type IDE and did not lose activation by small peptides. An electrostatic activation mechanism would suggest, simplistically, that loss of R429 from domain 2 would enhance electrostatic attraction between the chamber walls and therefore decrease $k_{cat}$ relative to wild type.

Although ATP hydrolysis as a driving force for a conformational change is an attractive mechanism, our observation that a non-hydrolyzable ATP analog is nearly as effective as ATP proves that this is not the case for IDE. Furthermore, the rate of ATP hydrolysis is slower than the rate of peptide cleavage, demonstrating that ATP hydrolysis cannot occur with every turnover of the enzyme.

Im et al. (supra) reported that ATP induced a conformational change in human IDE, specifically an increase in beta-sheet character as determined by CD spectroscopy. Although we noted increased thermal factors largely in the catalytic domain, we did not detect any significant change in the IDE structure when ATP was bound. Furthermore, Im et al. (supra) found that triphosphate, which is as effective as ATP at increasing IDE activity [FIG. 5 and Song et al., *Journal of Biologial Chemistry* 279, 54216-54220 (2004)], did not produce the same conformational changes as ATP. This suggests that the conformational effects produced by ATP observed by Im et al. are likely not related to its ability to increase substrate hydrolysis.

The electrostatic activation mechanism we propose does not readily explain why binding of polyphosphates/polyanions to the specific site activates to a greater extent than nonspecific binding to the positively charged surface. Without being bound by theory, it may be that the electrostatic attraction is most affected by positioning a polyanion near the center of the positive surface where the specific site is located. Another possibility is that electrostatic changes do not represent the only activation mechanism. The increased thermal motion seen in the catalytic domain of IDE, for example, can reflect not just a loosening of the interface between the two halves of the enzyme but a separate effect on the dynamics of that domain caused by polyphosphate/polyanion binding at the specific site. Binding at the nonspecific sites would not then produce this change in dynamics. Monovalent ions, such as those from the NaCl used here, likely are able to increase IDE activity by shielding the surface charge in the same way as polyphosphate/polyanion binding to the nonspecific sites. They also would disrupt binding to the specific site, preventing the greater activation produced by polyphosphate/polyanion binding at that position. The observations in yeast, however, indicate that polyphosphate/polyanion activation is a factor in determining effective IDE activity even at the ionic strength of the cytosol, and that this heterotropic activation also affects IDE activity in higher eukaryotes.

Example 2

Identification of the Allosteric Regulatory Site of IDE

Insulin degrading enzyme (IDE) is responsible for the metabolism of insulin and plays a role in clearance of the Aβ peptide associated with Alzheimer's disease. Unlike most proteolytic enzymes, IDE, which consists of four structurally related domains and exists primarily as a dimer, exhibits allosteric kinetics, being activated by both small substrate peptides and polyphosphates such as ATP.

The crystal structure of a catalytically compromised mutant of IDE has electron density for peptide ligands bound at the active site in domain 1 and a distal site in domain 2. Mutating residues in the distal site eliminates allosteric kinetics and activation by a small peptide, as well as greatly reducing activation by ATP, demonstrating that this site plays a key role in allostery. Comparison of the peptide bound IDE structure (using a low activity E111F IDE mutant) with unliganded wild type IDE shows a change in the interface between two halves of the clamshell-like molecule, which can enhance enzyme activity by altering the equilibrium between closed and open conformations. In addition, changes in the dimer interface suggest a basis for communication between subunits. These findings indicate that a region remote from the active site mediates allosteric activation of IDE by peptides. The activation appears to involve a small conformational change that weakens the interface between two halves of the enzyme.

Experimental Procedures:

IDE Expression and Purification—

Native rat IDE (rIDE, residues 42-1016, 95% identical and 98% similar to the human ortholog), E111F-rIDE, and IDE distal site mutants were expressed as hexahistidine fusion proteins in SF9 insect cells. All enzymes produced begin at methionine 42, which is believed to be the in vivo start site, and extend through the native C-terminal residue leucine 1019. Selenomethionine incorporation was achieved by pre-incubating Sf9 insect cells with rIDE-baculovirus for 10 hours in methionine-depleted SF-900 II SFM media (Invitrogen). Selenomethionine was then added to the media and the cells were allowed to incubate another 72 hours before harvesting.

IDE was purified using HIS-select Ni-NTA agarose (Sigma) utilizing the N-terminal hexahistidine affinity tag (hexahistidine sequence and a linker containing a TEV protease cleavage site), eluting by proteolytic removal of the hexahistidine sequence with TEV protease. Protein was estimated using Coomasssie Blue Reagent (BioRad) with BSA as a standard.

Preparation of IDE Distal Site Mutants—

IDE distal site mutants were generated by site-directed mutagenesis using the QuikChange kit (Stratagene) with the wild type rIDE cDNA in pFastBac HTb as a template. Oligonucleotides used for mutagenesis with the base changes in bold and underlined were:

```
Y609F:
Forward
                                         (SEQ ID NO: 12)
5'-CTCAACGACTATGCATTTGCAGCAGAGCTAGCA-3'
Reverse
                                         (SEQ ID NO: 13)
5'-TGCTAGCTGTGCTGCAAATGCATACTCGTTGAG-3'
```

-continued

V360S:
Forward
                                (SEQ ID NO: 14)
5'-TGGGTAAACACCCTGTCTGGGGGACAGAAGGAA-3'
Reverse
                                (SEQ ID NO: 15)
5'-TTCCTTCTGTCCCCCAGACAGGGTGTTTACCCA-3'

I374S:
Forward
                                (SEQ ID NO: 16)
5'-GGTTTTATGTTTTTTTCCATTAATGTGGACTTA-3'
Reverse
                                (SEQ ID NO: 17)
5'-TAAGTCCACATTAATGGAAAAAAACATAAAACC-3'

Crystallization and Structure Determination—

Enzyme at 8 mg/ml in 50 mM Tris 7.4, 1 mM DTT, and 100 mM NaCl was crystallized by sitting drop vapor diffusion. Protein was mixed 1:1 with well solution containing 100 mM sodium citrate pH 6.5, 100 mM ammonium acetate, and 20% PEG 4000, and crystals grown at 20 or 22° C. Full-sized (0.2 mm longest dimension) crystals grew reproducibly within two weeks. Crystals produced in this manner diffracted only to low resolution, but dehydration by brief (1-5 second) transfer to 50% PEG 4000 prior to flash cooling in liquid nitrogen gave high resolution diffraction.

Data were collected at the Southeast Regional Collaborative Access Team (SERCAT) 22-ID and 22-BM beamlines at the Advanced Photon Source (APS), Argonne National Laboratory. Se-MAD data sets were collected at both SERCAT 22-ID at APS and X25A at the National Synchrotron Light Source (NSLS) through each of their mail-in crystallography programs. X-ray data were processed using HKL2000 and the space group of the crystals found to be C2 with one molecule per asymmetric unit and cell parameters of a=115.8 Å, b=71.2 Å, c=114.6 Å, α=90.00, β=92.46, and γ=90.00 for the wild type enzyme and a=115.5 Å, b=71.0 Å, c=114.4 Å, α=90.00, β=92.97, and γ=90.00 for the E111F mutant. The data sets were checked for possible pseudomerohedral twinning, but no significant twinning was detected using PHENIX XTRIAGE.

Molecular replacement was performed using Phaser and CCP4 using the deposited hIDE structure in complex with the amyloid beta peptide (Protein Data Bank code 2G47) as a search model. The Rfree value of the model after molecular replacement was 0.42. Anomalous density maps calculated using phases from selenomethionine data showed peaks consistent with methionine residue positions in the model, confirming the molecular replacement solution. Model building and refinement using the molecular replacement solution was done using COOT and REFMAC5. Water picking was done using PHENIX with manual editing of all additions in COOT. Six TLS groups, determined using the TLS Motion Server, were used in atomic displacement refinement for each structure. Final refinement was performed using CNS and PHENIX. Molecular structure figures were made using PyMOL (www.pymol.org). The final wild type model contains residues 42-963 and residues 980-1011 with 232 ordered solvent molecules and one zinc ion. The rIDEE111F model contains residues 42-965 and 978-1011 with 185 ordered solvent molecules and two peptides, one comprised of seven alanine residues and the other of eight alanine residues. Data and refinement statistics are listed in Table 3. Protein-protein interfaces were analyzed using the program PISA.

TABLE 3

Summary of crystallographic data and model refinement

| | unliganded IDE | rIDE-E111F |
|---|---|---|
| Crystallographic data | | |
| Wavelength (Å) | 0.9718 | 1.0000 |
| Resolution (Å) | 50-2.08 | 50-2.14 |
| Last shell (Å) | 2.16-2.08 | 2.24-2.14 |
| Average redundancy (last shell) (%) | 4.6 (2.9) | 2.8 (2.0) |
| $R_{merge}$ (last shell) (%) | 0.10 (0.47) | 0.088 (0.41) |
| I/σI (last shell) (%) | 11.9 (2.1) | 14.96 (3.98) |
| Completeness (last shell) (%) | 97.5 (87.9) | 98.7 (99.6) |
| Refinement | | |
| Resolution (Å) | 50-2.08 | 50-2.14 |
| Number of reflections included in refinement | 52364 | 47228 |
| $R_{work}/R_{free}$ | 0.19/0.26 | 0.19/0.26 |
| estimated coordinate error (Å)[a] | 0.31 | 0.33 |
| r.m.s.d. bond lengths (Å) | 0.008 | 0.009 |
| r.m.s.d. bond angles (°) | 1.11 | 1.16 |
| r.m.s.d. chirality (°) | 0.07 | 0.08 |
| r.m.s.d. planarity (°) | 0.005 | 0.005 |
| r.m.s.d. dihedral angles (°) | 14.9 | 16.4 |
| B[b] r.m.s.d. bonded atoms | 3.8 | 4.3 |
| Average B for all protein atoms (Å²) | 39 | 56 |
| Average B for ordered solvent (Å²) | 37 | 48 |
| Number of protein molecules in the asymmetric unit | 1 | 1 |
| Number of protein residues in the asymmetric unit | 954 | 958 |
| Number of peptide residues in the asymmetric unit | 0 | 15 |
| Number of protein and peptide atoms in the asymmetric unit | 7802 | 7909 |
| Solvent content (%) (Matthews coefficient) | 41.8 (2.1) | 41.7 (2.1) |
| Number of solvent molecules | 232 | 185 |
| Number of metal ions | 1 | 0 |

[a]Maximum likelihood method in Phenix [43, 44].
[b]Isotropic thermal factor.

Identification of Bound Ligand—

The identity of the unknown ligand observed in the rIDE-E111F structure was determined by MALDI-TOF analysis using a crystallization drop from which crystals were harvested. In addition, a fresh sample of rIDE-E111F was analyzed at specific steps during purification. To verify that the unknown ligand was not introduced with the TEV protease added during purification, a TEV sample was also analyzed as a control. MS/MS analysis was performed using the precursor peak at 2896 from the HIS-tag alone sample in order to determine sequence information. MALDI-TOF and MS/MS experiments (scan range 500-4000) were performed at The Scripps Center for Mass spectrometry and at The University of Kentucky Proteomics Core Facility. Data analysis was performed using MS-Product and Data Explorer Software (Applied Bosystems).

Enzyme Activity Assay—

The activity of IDE was measured by following the increase in fluorescence upon hydrolysis at the L-R bond of the fluorogenic peptide Abz-GGFLRKHGQ-EDDnp (SEQ ID NO:3) on a SpectraMax Gemini XS fluorescence plate reader using an excitation wavelength of 318 nm and emission wavelength of 419 nm. Reactions were carried out in 200 μl volumes containing 50 mM Tris-HCl, pH 7.4, 1.92 μg of wild type rIDE, 4.6 μg of rIDE-V360S, 4.3 μg rIDE-I374S, or 1.63 μg of rIDE-Y609F. For measurements of activation by bradykinin, IDE activity was determined with 10 μM Abz-GGFLRKHGQ-EDDnp (SEQ ID NO:3) as substrate in 50 mM Tris-HCl buffer, pH 7.4. The amount of protein was 0.5

μg for wild type rIDE and 5 μg for each of the IDE distal-site mutants. Data were analyzed using Softmax 4.0 (Molecular Devices) and kinetic parameters calculated with Prism (Graphpad Software). Specific activity with the Abz-GGFL-RKHGQ-EDDnp (SEQ ID NO:3) substrate is 8,131 nmol/min/mg for the wild type enzyme and 5.2 nmol/min/mg for the E111F mutant. Under these assay conditions, both wild type and mutant rIDE are almost completely dimeric.

Fluorescence Measurements—

Fluorescence measurements of TNP-ATP binding were performed on a Perkin-Elmer LS55 Luminescence Spectrometer. Titrations were monitored at an excitation wavelength of 403 nm and emission wavelength of 547 nm. The temperature of the sample was maintained at 20±0.1° C. by circulating thermostatically controlled water through the cuvette holder. Assays were conducted in 200 μL reaction mixtures containing 50 mM Tris-HCl, pH, 7.4, 10 μM Abz-GGFLRKHGQ-EDDnp (SEQ ID NO:3) as substrate, and 0.5 μg wild type rIDE, 2.3 μg rIDE-V360S, 2.0 μg rIDE-I374S or 1.62 μg rIDEY609F and the indicated concentration of ATP. The fluorescence of TNP-ATP was subtracted from the total fluorescence of enzyme+TNP-ATP to yield specific fluorescence enhancement (ΔF).

Results and Discussion

Overview of the rIDE Structure:

The structures of wild type (SEQ ID NO:1) and E111F rIDE are very similar to the published structures of peptide bound and unliganded human IDE (hIDE) (SEQ ID NO:2). An alignment of wild type rIDE and hIDE from the amyloid beta peptide complex (Protein Data Bank code 2G47) yields an r.m.s.d. of 0.6 Å for 954 Cα atoms. The four structurally similar domains each have an α+β fold and arrange to form the same closed clamshell conformation as hIDE, with the N- and C-terminal halves of the clamshell connected by a single polypeptide chain. In the closed conformation, the two halves of the clamshell are in contact with one another forming an enclosed cavity, and the active site of the enzyme is accessible from this internal substrate-binding chamber. The two rIDE structures show similar local variations in isotropic atomic displacement factors (B factors), although the values for the peptide bound enzyme are generally higher, particularly for the first two domains.

Location and Identification of Ligands Bound to rIDE-E111F:

The E111F mutation greatly reduces catalytic activity while maintaining the ability to bind substrates. We began work with this mutant with the intention of using it to obtain structural information on a variety of complexes between the enzyme and substrate peptides. Interestingly, though, a difference (Fo-Fc) map made with the rIDEE111F data in the absence of added substrate peptides revealed two regions of positive electron density located within the central cavity of the enzyme (FIG. 14a) consistent with bound peptide ligand. One segment of difference density was found adjacent to the active site of the enzyme in domain 1, and the second segment was found in the structurally equivalent region of domain 2.

Figure 14:
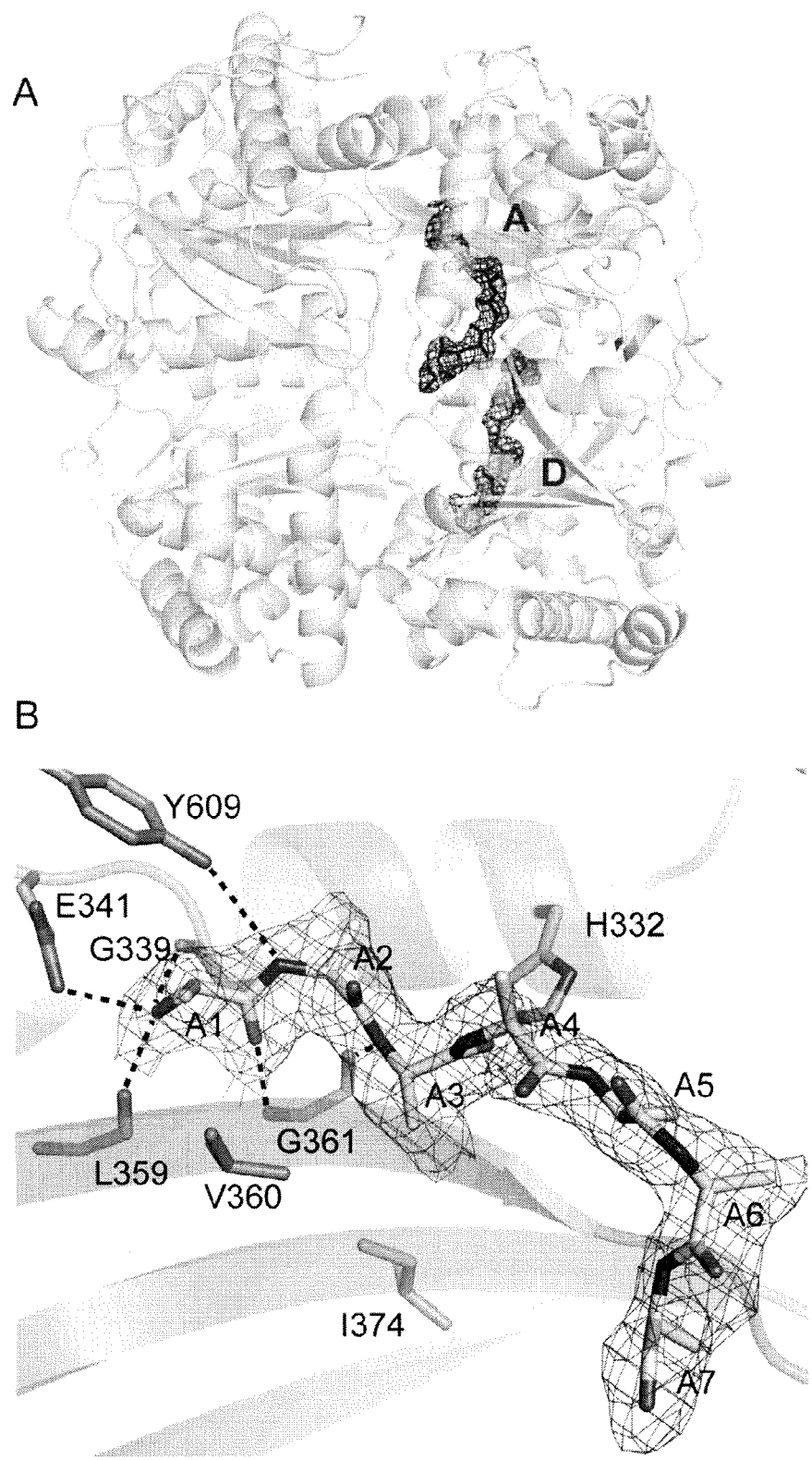
FIG. 14 shows the rIDE-E111F crystal structure. Panel A shows an overview of the structure. A ribbons representation of the enzyme is shown together with polyalanine ligands (red sticks) built into difference density (Fo-Fc, blue mesh, 2.0 sigma contour) at the active (A) and distal (D) sites. Difference density was produced with phases from a refined model of the enzyme prior to adding peptide models and so is not biased by the peptide models. Panel B shows the interaction of bound peptide with the domain 2 distal site of rIDE-E111F. The polyalanine peptide ligand is shown (residues 1-4 of the seven residues in the model) in a stick representation with difference density calculated as described above (blue mesh, 2.0 sigma contour). Likely hydrogen bonds to the peptide backbone are indicated by dashed lines.
Figure 15:
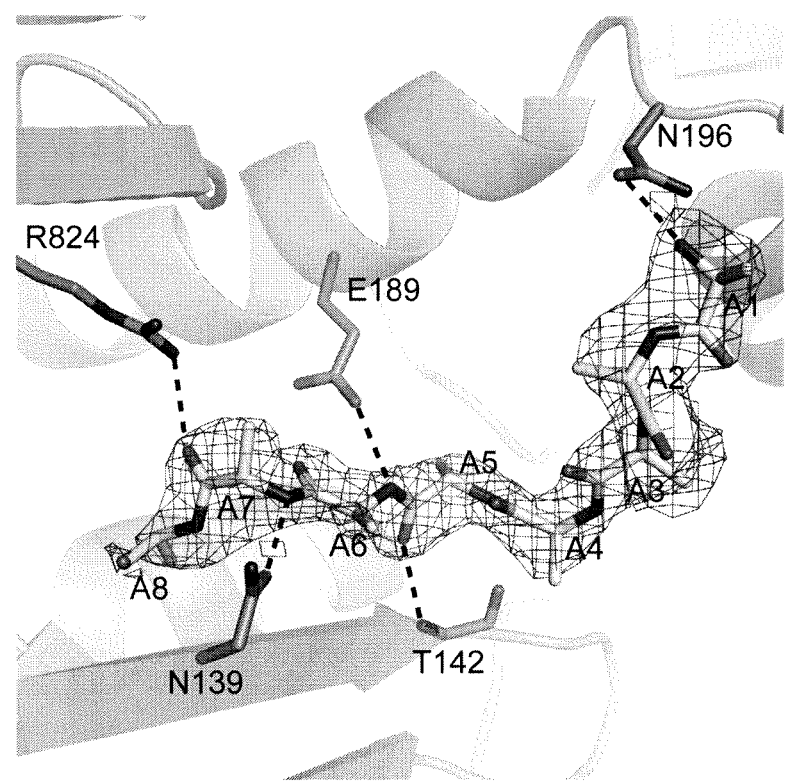
FIG. 15 shows the interaction of bound peptide with the active site (domain 1). The polyalanine peptide is shown as a stick representation in difference density (blue mesh, 2.0 sigma contour). Hydrogen bonds to backbone groups in residues 1, 5, 6, and 7 are indicated by dashed lines.

Two separate polypeptide chains were modeled into the ligand density. The ligands were built as polyalanine, since density for the peptide side chains was weak and fragmented. The first ligand was modeled as an eight-residue peptide bound at the active site, where it is positioned to interact with the enzyme through a series of hydrogen bonds with the peptide backbone (FIG. 15). The second ligand, located at the vestigial active site present in domain 2, the distal site, was modeled as a seven-residue peptide that is also positioned to make a number of hydrogen bond interactions with the enzyme (FIG. 14B). Both peptides adopt an extended conformation, aligning along the last strand of the central sheet of their respective interacting domains consistent with the usual location of substrate peptides in zinc metallopeptidases. For the peptide in the distal site, the main chain carbonyl groups of Gly339 and Leu359 as well as the side chain of Glu341 are in position to interact with the N-terminal amino group.

Figure 16:
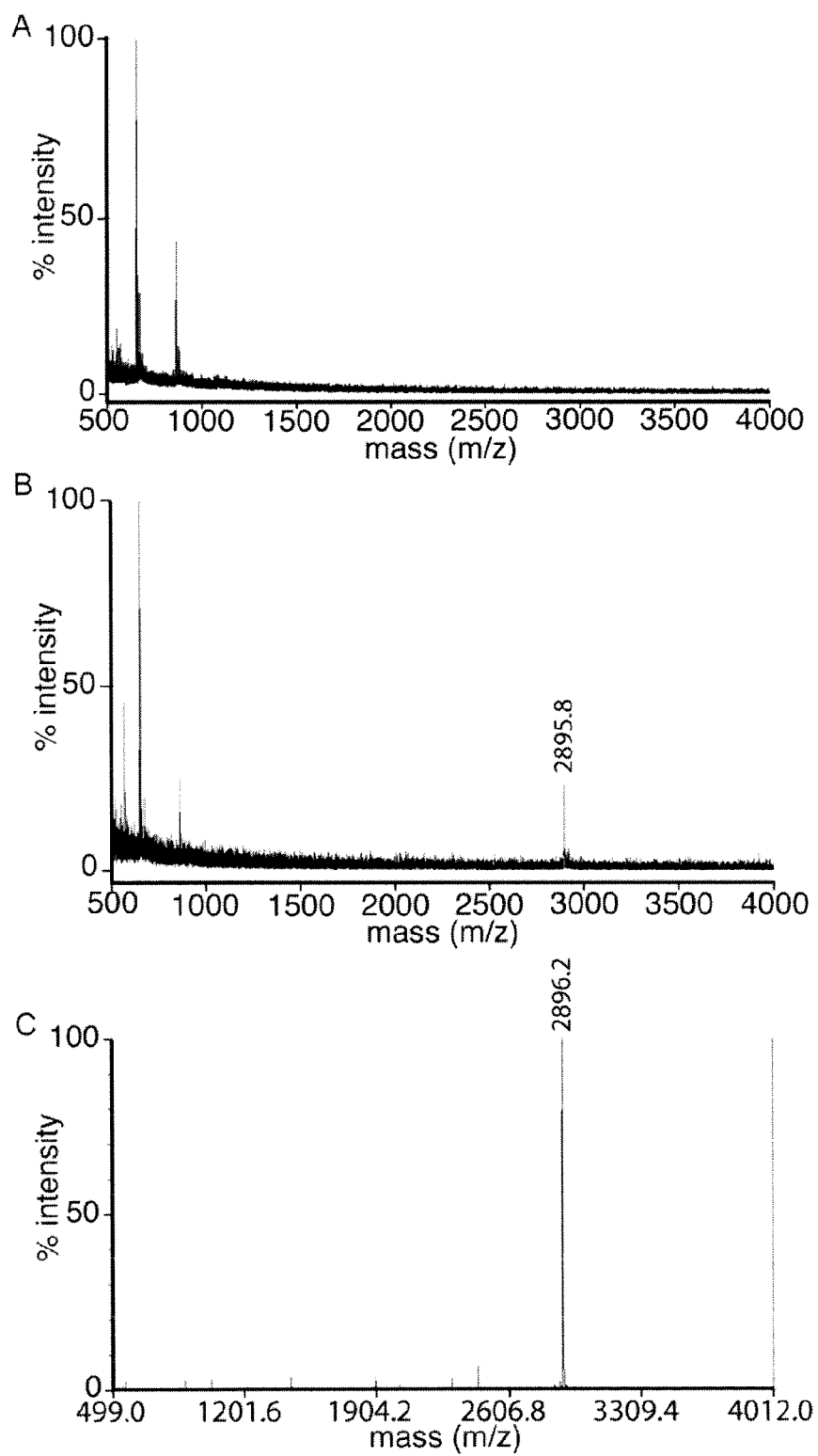
FIG. 16 shows a mass spectrometry identification of ligand bound to rIDE-E111F. (A) MALDI-TOF analysis of purified rIDE-E111F before removal of the polyhistidine fusion sequence. Only matrix peaks are observed. (B) MALDI-TOF analysis of rIDE-E111F after cleavage of the polyhistidine fusion sequence. A peak representing bound ligand is evident. (C) MALDI-TOF analysis of the polyhistidine fusion tag eluted from Ni-NTA agarose resin after normal rIDE-E111F purification. This peak matches the peak representing ligand bound to purified rIDE-E111F in panel B and is consistent with the expected mass of the fusion sequence.

Additionally, the side chains of Tyr609 and H332 and the main chain carbonyl of Gly361 can make hydrogen bonds with the peptide backbone. To identify the bound ligand, samples were analyzed by mass spectrometry at various steps during the purification of rIDE-E111F: (1) the enzyme before proteolytic removal of the polyhistidine fusion sequence used in purification, (2) purified enzyme after elution from the Ni-NTA resin by proteolytic removal of the polyhistidine sequence, and (3) imidazole eluate from the metal affinity resin containing any polyhistidine fragment remaining bound after IDE elution. No significant mass peaks consistent with the observed ligands were observed before the cleavage of the polyhistidine fusion sequence (FIG. 16A), suggesting that the unknown ligand was not being co-purified from cell lysates. However, a mass peak at 2895.8 Da was seen in the sample after cleaving the fusion sequence with TEV protease to elute the enzyme from the Ni-NTA resin (FIG. 16B). No such peak was observed for the wild type rIDE purified in the same manner or in a control containing only the TEV protease. A sample containing N-terminal polyhistidine fusion sequence eluted from the Ni-NTA agarose gave a peak at 2896.2 Da (FIG. 16C), closely matching the peak in the enzyme sample. MS/MS analysis of the 2896.2 Da peak gave 18 of 20 expected b-ions, 12 of 21 expected y-ions, and at least 3 of 22 expected y*-ions, allowing unambiguous identification of the ligand sequence. This result is consistent with the bound ligand being the polyhistidine fusion sequence after removal of its N-terminal methionine residue and acetylation of the new N-terminal serine (N-Ac-SYYHHHHHHDYDIPTTEN-LYFQ (SEQ ID NO: 18), expected mass of 2895.9 Da). Posttranslational modification of this type for polyhistidine fusion sequences of proteins expressed in insect cells has been noted previously.

These data indicate that the ligands observed in the crystal structure are the cleaved polyhistidine fusion sequence bound to rIDE-E111F. Given the positions of the two modeled peptides, it is possible that they represent two portions of a single polyhistidine fusion sequence with the joining residues disordered and therefore not visible in the crystal structure. This type of binding at the active and distal sites of IDE has been seen with other peptides. It is also possible, however, that different peptides are bound at the active and distal sites, with only eight of 22 residues ordered in the active site peptide and seven of 22 residues ordered in the distal site peptide. Bound peptides are presumably not seen associated with wild type rIDE because the polyhistidine fusion sequences are degraded by the active enzyme.

Mutations in the Distal Site Eliminate Allosterism:

Our previous work showed that IDE displays allosteric kinetics and that small peptides can act as activators of the enzyme. The finding in this study of peptide ligand bound to the distal site indicates that this site can be involved in mediating the allosteric regulation of rIDE. To test this hypothesis, we mutated several distal site residues in close proximity to the bound peptide. Three mutant versions of rIDE, Y609F, V360S, and I374S were prepared and the mutant constructs analyzed for allosteric kinetics and activation by a small peptide. The side chain of Y609 is positioned to hydrogen bond to the backbone of bound peptide as noted previously, and V360 and I374 are positioned to interact with side chains of a peptide bound at the distal site.

Initial velocity versus substrate concentration plots (FIG. 17A) for activity on the fluorogenic peptide substrate Abz-GGFLRKHGQ-EDDnp (SEQ ID NO:3) show that the allostery present in the wild type enzyme is lost in each of the three distal site mutants. Fitting the data with a sigmoidal function gives Hill coefficients (See Table 4) of 1.80 for the wild type enzyme and 1.04, 1.07, and 1.12 for the Y609F, V360S, and I374S mutants. Vmax values for the mutants were all decreased approximately 10 fold relative to wild type, consistent with the loss of activation, while apparent Km values remain roughly the same. Heterotropic activation with the small peptide bradykinin (approximately 4-fold for the wild type enzyme) is also lost in all three mutants (FIG. 17B), showing directly the absence of allosteric activation.

TABLE 3

Kinetics of IDE and distal site mutants.

|  | Wild Type | Tyr609Phe | Val360Ser | Ile374Ser |
| --- | --- | --- | --- | --- |
| Vmax (nmol/min/mg) | 35.5 ± 11.6 | 2.6 ± 0.56 | 2.01 ± 0.08 | 3.45 ± 0.22 |
| Hill coefficient | 1.8 ± 0.16 | 1.04 ± 0.14 | 1.07 ± 0.30 | 1.12 ± 0.2 |
| Km (μM) | 15.87 ± 1.19 | 6.86 ± 1.18 | 8.61 ± 0.81 | 8.5 ± 1.74 |
| $K_D^{TNP-ATP}$ (μM) | 1.0 ± 0.1 | 2.0 ± 0.3 | 3.7 ± 0.8 | 2.1 ± 0.5 |

Figure 17:
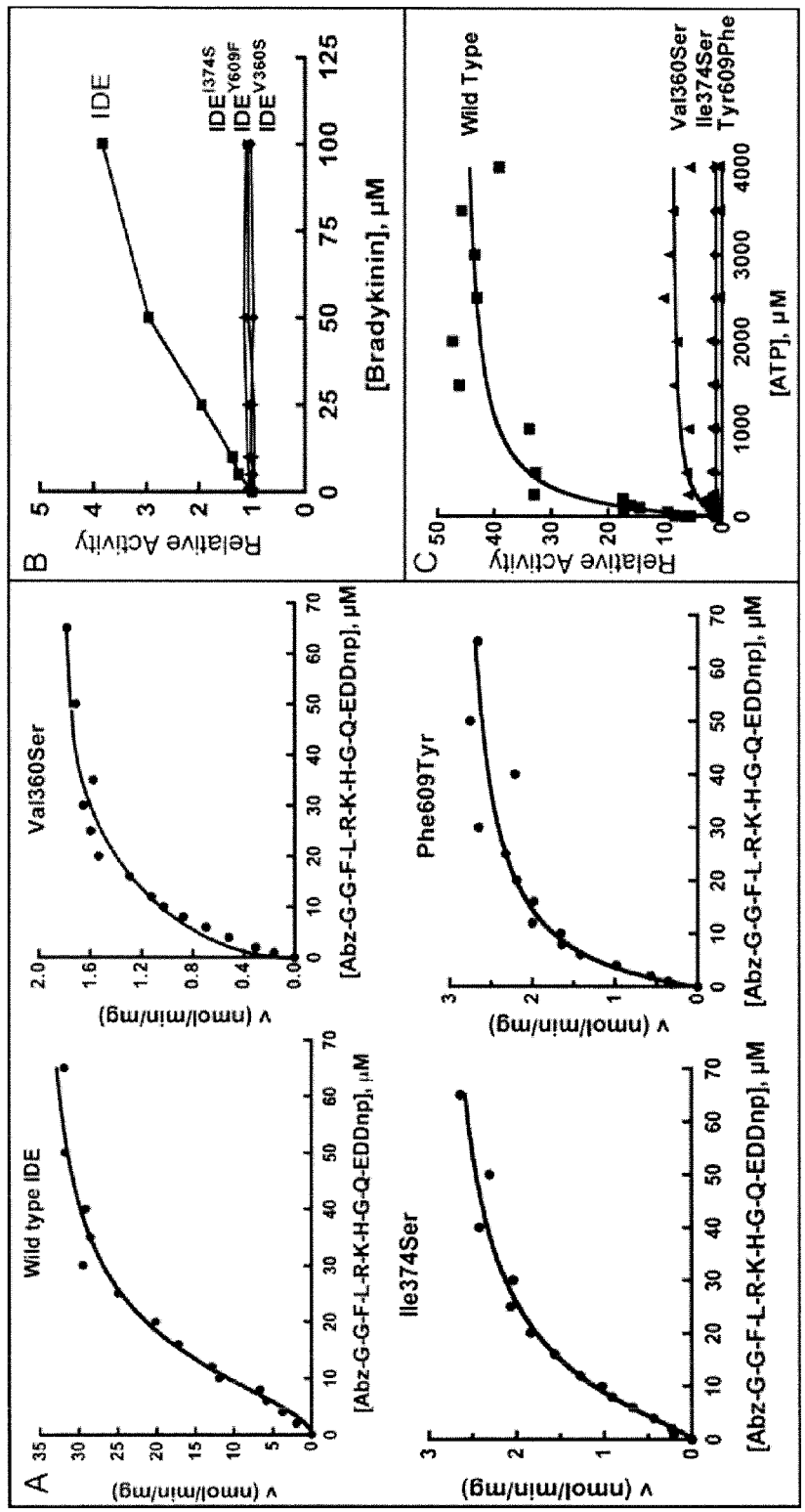
FIG. 17. Effects of distal site mutations. (A) Comparison of the kinetics of wild type IDE with the distal site mutants. Activity was measured with varying amounts of Abz-GGFL-RKHGQ-EDDnp (SEQ ID NO:3) substrate as indicated. Either hyperbolic (Michaelis-Menten equation) or sigmoidal curves (Hill equation) were fit to the data. (B) Effect of bradykinin on the activity of wild type IDE and the distal site mutants. (C) Activation of wild type IDE and distal site mutants by ATP. Relative activity is the fold activation above the level of the wild type enzyme alone.
Figure 18:
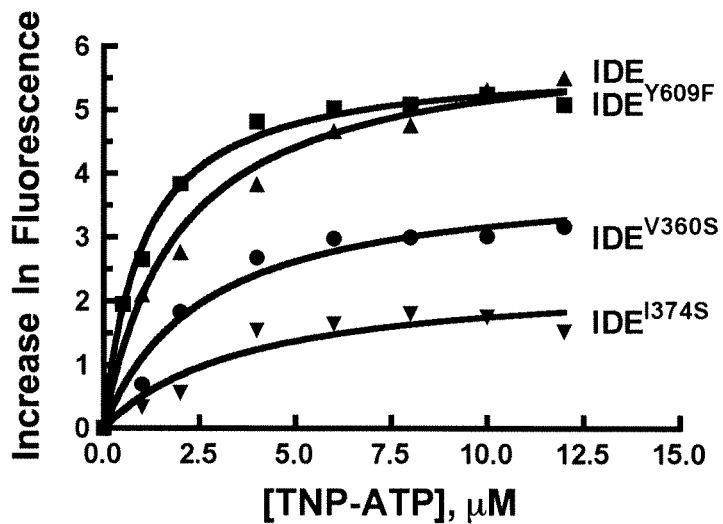
FIG. 18 shows the kinetics of ATP analog binding to wild type and distal site mutant IDE. The fluorescence increase on binding of (2,4,6-trinitrophenyl)ATP (TNP-ATP) is plotted for the indicated IDE constructs as a function of ligand concentration. Data were fit to a hyperbolic one site binding mechanism.
Figure 19:
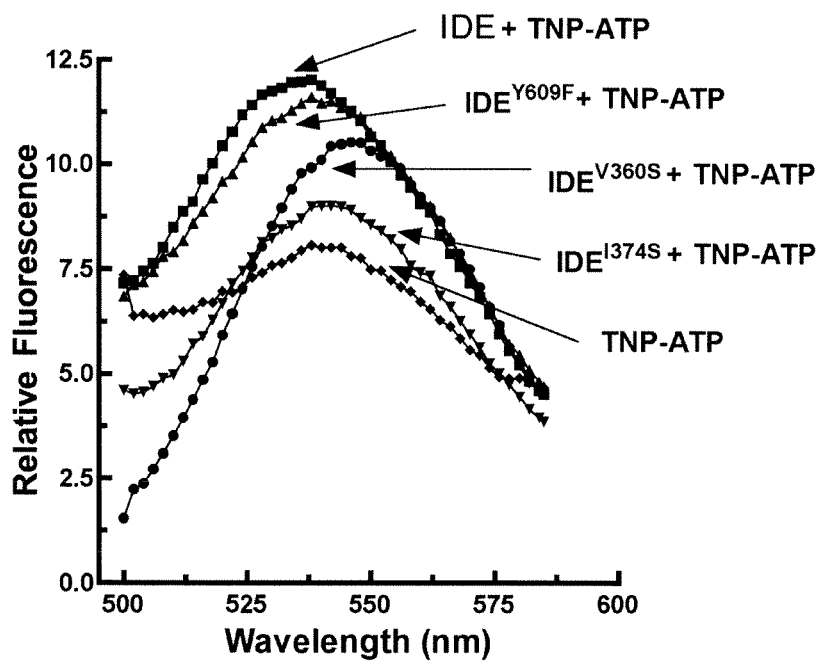
FIG. 19 shows the fluorescence spectra of TNP-ATP bound to wild type IDE and the distal mutant IDEs. Fluorescence emission spectra of 10 µM TNP-ATP in 50 µM Tris-HCl, pH7.4, was measured in the presence of 1.5 µM of each wild type IDE and the indicated IDE distal mutants. Fluorescence spectra were recorded with a λexc=403 nm on a Perkin-Elmer LS55 Luminescence Spectrometer.

ATP also acts as a heterotropic activator of IDE, increasing the cleavage rate of the fluorogenic peptide substrate Abz-GGFLRKHGQ-EDDnp (SEQ ID NO:3) more than 40 fold [15]. However, ATP activation of the V360S mutant was reduced to 8 fold, and activation by ATP was not significant for the I374S and Y609F mutants (FIG. 17C). In all three mutants, enhancement of TNP-ATP fluorescence emission indicates that they still bind the ATP analog, although with lower affinity than the wild type enzyme (Table 3, FIG. 18). However, the degree of TNP-ATP fluorescence enhancement is diminished in the mutants, as is the blue shift in the emission peak observed upon binding to the wild type enzyme (FIG. 19). These differences in the emission spectrum of bound TNP-ATP indicate a change in the local environment in the mutants relative to the wild type enzyme, which may result from the loss or alteration of a conformational change associated with allosteric activation.

Figure 20:
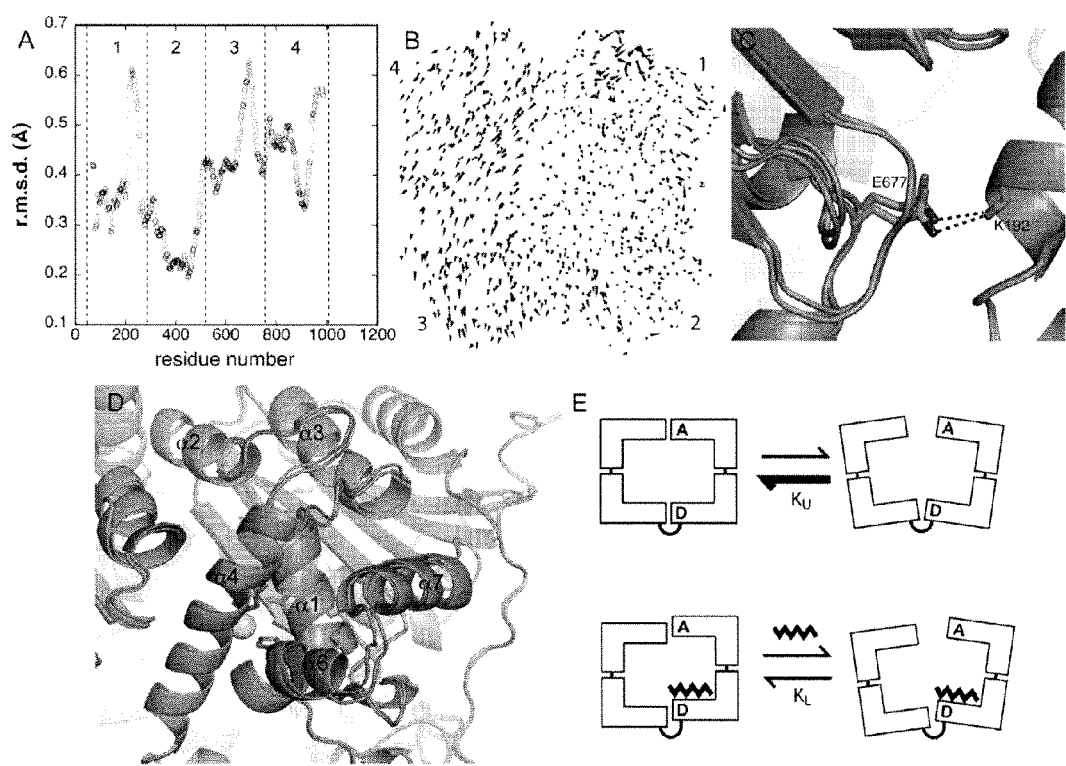
FIG. 20 shows basis for allosteric activation. (A) Plot of r.m.s. main chain atom positional differences between unliganded IDE and rIDE-E111F with bound peptide ligands at the active and distal sites. Boundaries for domains 1-4 are indicated by the vertical dashed lines. The two structures were superimposed on Cα positions in domains 1 and 2. (B) A porcupine type diagram illustrating the conformational change between unliganded IDE and rIDE-E111F superimposed on domains 1 and 2. Cones indicate the direction and magnitude of differences between Cα positions. Domains are labeled. The size of the cones has been scaled by a factor of 3 relative to the dimensions of IDE to make the conformational change visible in a small diagram. (C) Example of a change in an interface contact between two halves of IDE comparing aligned unliganded IDE (green) and rIDE-E111F (cyan) structures. (D) Conformational changes in the active site domain (domain 1). Superimposed structures of unliganded IDE (green) and rIDE E111F (cyan) are shown. Residues at the active site are shown in a stick representation, and the zinc ion cofactor is drawn as a yellow sphere. (E) Model of IDE allosteric activation. In the absence of bound peptide at either the active or distal sites, the equilibrium between the closed and open forms of IDE (KU) is shifted toward the closed form, which prevents substrate binding and product release. With peptide bound at the distal site (and possibly the active site), the equilibrium (KL) shifts to increase the population in the open form, enhancing peptide binding and product release.

Structural Basis for Allosterism:

Comparison of the ligand free rIDE structure and the rIDE-E111F structure with ligand bound at the distal and active sites suggests a likely structural basis for allosterism. Alignment of the two enzyme structures on Cα positions in the N-terminal halves (domains 1 and 2) of the molecules reveals a difference in the relative positions of the C-terminal portions of the molecule (FIG. 20A, B). Binding ligand appears to induce a small shift of domains 3 and 4 relative to domains 1 and 2. While the observed structural rearrangement is small, with a maximum amplitude of 1.5 Å (r.m.s.d. of 0.58 Å for domain 3 and 4 main chain atoms), it is largely concerted, with nearly all Cα positions moving in the same direction (FIG. 20B). Interactions across the interface between the N- and C-terminal halves of the molecule are affected (FIG. 20C). The number of residues involved in the interface increases from 133 in the wild type enzyme to 135 in the mutant, although the total solvent accessible surface area buried decreases slightly from 2402 Å2 for the wild type to 2324 Å2 for the mutant. Overall, both the total number of hydrogen bonds and salt bridges across the interfaces decreases in the peptide bound mutant (wild type: 29 H-bonds, 13 salt bridges; IDEE111F: 28 H-bonds, 11 salt bridges). It is important to note that while the total number of residues and polar contacts change modestly on peptide binding, there are even more extensive differences in particular residues involved in the interface and those making polar contacts.

Given the number of changes in the interface between the two halves of the molecule, its stability is also likely altered. Destabilizing the interface would increase partitioning of the enzyme into an open conformation (with the two halves hinging about the chain linking domains 2 and 3) necessary for substrate binding and product release. Since it is believed that the rate of adopting the open conformation limits IDE activity, weakening the interface by peptide binding in the distal site (and possibly the active site) would be expected to activate the enzyme. The relative shift of the two halves of the enzyme is also is evident when comparing the liganded and unliganded hIDE structures determined by Tang and coworkers, providing additional evidence for the significance of the observation in this study. As already noted, the crystallographic thermal factors for the first two domains of the ligand bound mutant are consistently higher than those for the unliganded enzyme. This difference may reflect a higher relative mobility of the two halves of the peptide bound enzyme, which would be consistent with a weakening of the interface.

In addition to the largely translational shift between the two halves of the enzyme, other changes in conformation between the unliganded enzyme and rIDE-EIIIF are evident. Elements within the active site domain (domain 1) rotate with respect to the remainder of the domain as well as domains 2-4. The rotation, which occurs roughly about an axis through the domain 1-domain 2 interface, involves helical elements on one side of the central sheet of the domain. In particular, helices 1 (containing the catalytic and two zinc ion binding residues) and 2 (residues 105-135) as well as helices 3-7 (residues 157-247) rotate largely as a rigid body (~5°). Helices 3-7 are positioned over the active site shielding it from solvent. Since the helical elements that rotate border on the substrate-binding site, it is possible that the change in orientation accompanies peptide binding at the active site in rIDE-E111F. Interestingly, helices 2 and 4 form part of the interface between the two halves of the molecule, largely interacting with elements in domain 4. Thus the conformational change in domain 1 may play a role in the shift in the two halves between the unliganded and ligand-bound IDE structures. Alternatively, the change in the interface might drive the conformational change in the active site domain.

One other conformational change occurs between the unliganded wild type enzyme and rIDE-E111F. IDE functions as a dimer, and one of the contacts in the human IDE crystals has been identified as the dimer interface. This interface has also been confirmed as the dimer interface with the rat enzyme.

Figure 21:
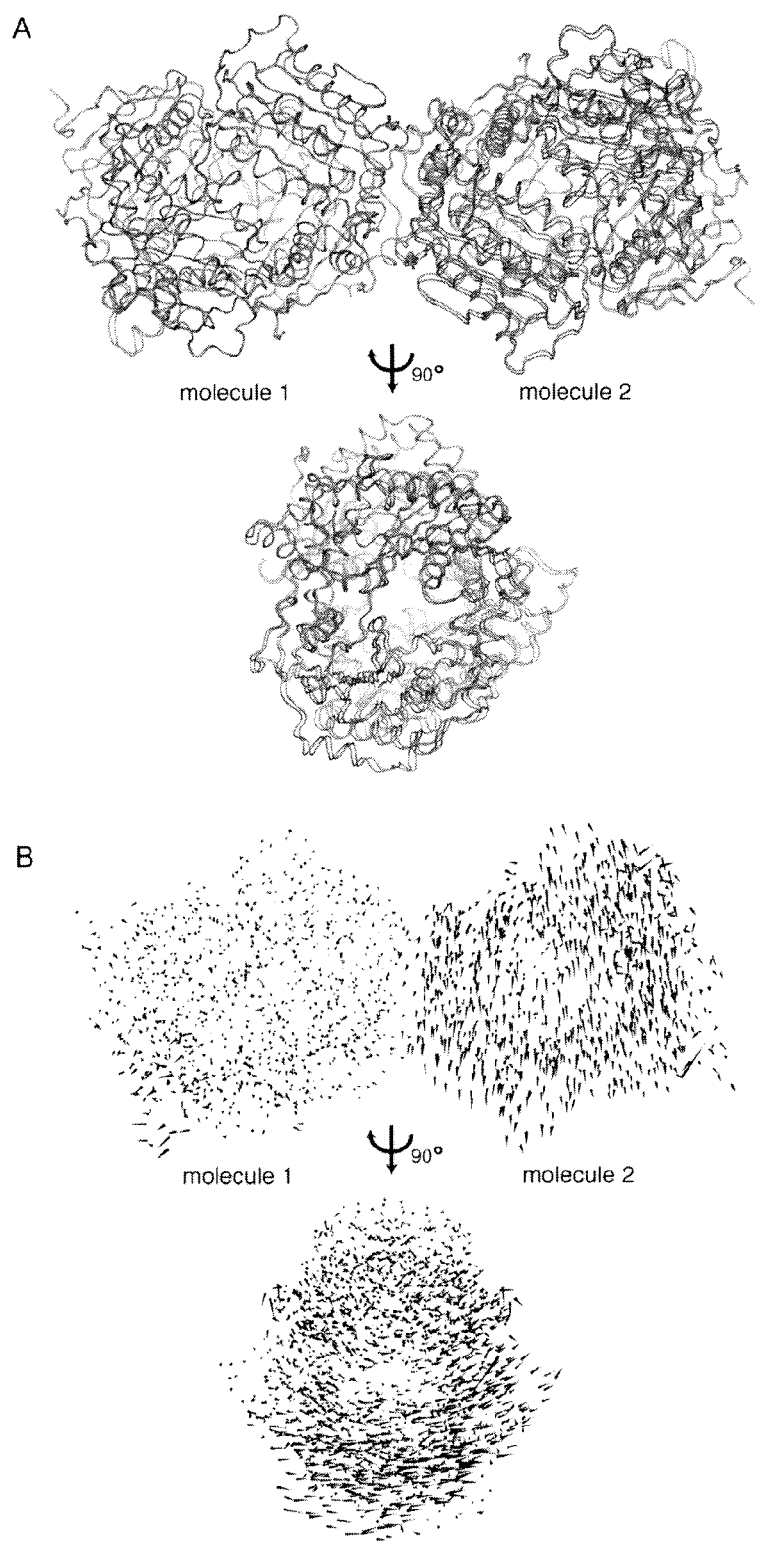
FIG. 21 shows the changes at the dimer interface. (A) Superimposed dimer structures of unliganded IDE (green) and rIDE-E111F with peptide ligand bound at the active and distal sites (cyan). Dimers are aligned based on Cα positions of one monomer (molecule 1). (B) Porcupine type representation of the change in Cα positions between the two structures aligned on molecule 1. Cones represent the magnitude and direction of Cα positional changes. The size of the cones has been scaled by a factor of 2.5 relative to the dimensions of IDE to emphasize the conformational shifts. The orientations of the molecules are the same as those in panel A.

In rIDE-E111F, the subunits undergo a relative rotation compared to the unliganded enzyme (FIG. 21). This rotation occurs about an axis roughly orthogonal to the dimer axis, giving maximum shifts of about 2.5 Å when the structures are aligned on one monomer, The changes reduce the number of residues involved in the interface (per monomer) from 45 in the wild type enzyme to 42 in the mutant (residues Pro760, Tyr766, and Phe1005 no longer participating), although the total surface area actually increases slightly from 1392 Å2 in the wild type to 1432 Å2 in the mutant. The pattern of polar contacts is also altered somewhat, with differences at positions 586, 706, 756, 914, 1001, and 1009. In total, the number of interfacial hydrogen bonds changes from 14 in the wild type to 12 in the mutant, and the number of salt bridges remains at four, although different residues are involved.

Overall, the conformational changes between the wild type and peptide-bound mutant IDE do not greatly disturb the packing in the crystal.

Discussion

The results of the present study illuminate the mechanism of allosteric regulation in IDE. The crystal structure of rIDE-E111F shows peptide binding contacts at two distinct locations, the active site in domain 1 and a distal site located in domain 2. Changing the distal site through mutagenesis reduces the activity of the enzyme and converts its kinetics from allosteric to classical Michaelis-Menten. Mutations at the distal site also eliminate the previously observed heterotropic activation produced by small peptide substrates and reduce or eliminate activation by ATP.

In earlier work, we noted that the substrate bradykinin acts as an activator of the reaction of IDE with Abz-GGFL-RKHGQ-EDDnp (SEQ ID NO:3), while other peptide substrates, such as β-endorphin and dynorphin A(1-17), show activation at low concentrations and inhibition at higher concentrations. This can be explained by their relative affinity for the distal site versus the active site. The higher the affinity for the distal site relative to the active site the more the peptide acts as a pure allosteric activator, while binding at the active site produces competitive inhibition. It is interesting to note that the crystal structure of IDE in the presence of bradykinin shows peptide bound only at the distal site. This observation is consistent with bradykinin having a higher affinity for the distal site than the active site and therefore acting as a pure activator.

IDE crystallizes in a closed conformation in which the active site and substrate binding surfaces are inaccessible, and it seems likely that it is present primarily in the closed form in solution. The enzyme therefore must undergo a hinge-like motion to an open conformation in order to bind substrate and release products. Tang and coworkers have shown that destabilizing the interface between the N- and C-terminal halves of IDE by mutagenesis increases its activity, indicating that adopting an open conformation is rate limiting. The conformational change induced by peptide binding seen in this study suggests that allosteric activation occurs by destabilizing the N- and C-terminal domain interface. For small substrates, peptide binding at the distal site increases the population in the open conformation, enhancing both substrate binding and product release. Larger substrates can bind at both the active and distal sites simultaneously, and the enzyme does not therefore exhibit allosteric kinetics or heterotropic activation with these molecules.

Figure 22:
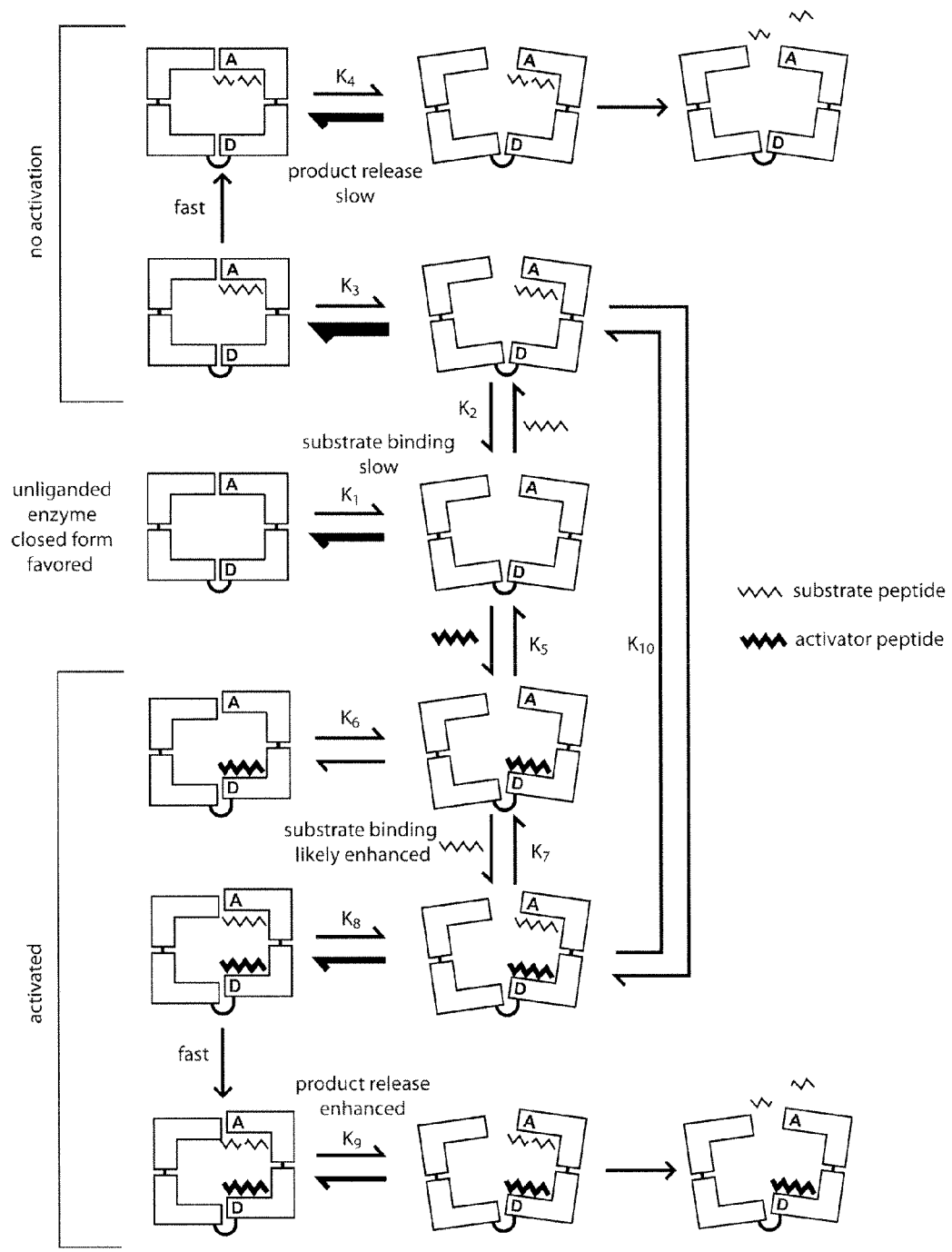
FIG. 22 shows the allosteric mechanism of IDE. A mechanistic model based on functional and structural observations is given. The two halves (domains 1 and 2, and domains 3 and 4) of an IDE monomer are shown schematically in closed and open forms with schematic representations of bound substrates and ligands. The active (A) and distal (D) sites are labeled. Substrate peptide is shown as a narrow zigzag line, and allosteric peptide as a heavy zigzag line. In the absence of bound ligand, the closed form of the molecule predominates (equilibrium K1). Binding substrate shifts the population distribution even more toward the closed form (K3) because the peptide interacts with both halves of the enzyme. The subsequent cleavage step is fast, but product release is likely rate limiting, since the closed form is still strongly favored (K4). Binding of peptide at the distal site alters the interface to increase the proportion of enzyme in the open conformation (K6). Substrate binding (K7) is therefore likely enhanced. Importantly, product release is also enhanced by the shift in distribution toward the open conformation (K9), effectively activating the enzyme at the substrate concentrations used for assays.

Since IDE functions as a dimer, a relevant question is whether activation occurs within or between subunits. Free monomeric IDE does not show allosteric kinetics and is not activated by added small peptides, indicating that the dimmer is required for allostery. At first glance, these results would seem to suggest that activation occurs across the dimer interface. However, work with mixed dimers carrying combinations of mutations at the active or distal sites in one or both subunits demonstrates that the primary allosteric effect occurs within each subunit of the dimmer. Without being bound by theory, we therefore favor a model in which binding of peptide to the distal site induces a conformational change in the same monomer that shifts the equilibrium toward the open form (FIG. 20E). The conformational change is, however, dependent on the monomer participating in dimer contacts with its partner subunit. Without this interaction, peptide binding at the distal site does not greatly alter the equilibrium between open and closed forms. A full scheme diagramming this model for IDE activation is given in FIG. 22.

How does peptide binding drive alteration of the interface between monomer halves? At the distal site, bound peptide lies close to the hinge region connecting the two halves of the molecule. It also interacts with Tyr609 from domain 3, which is located on the opposite side of the hinge. Without being bound by theory, binding of peptide in this region might influence the conformation of the hinge region and surrounding interface surfaces by direct interactions with residues on either side of the hinge. It is also possible that more general electrostatic effects, for example peptide binding changing the charge-charge interactions between the halves of the molecule, play a role in altering the interface.

Although activation within a monomer likely accounts for IDE allostery, previous data with mixed dimers indicate that some communication between the subunits occurs. In particular, mutations at the active site of one monomer appear to affect the activity of the other monomer, and it is possible that this occurs in the E111F mutant. The observed conformational shift at the dimer interface between ligand free wild type enzyme and ligand bound rIDE-E111F reported here suggests a possible structural basis for this communication. The conformational change in the active site domain (domain 1) of rIDE-E111F observed in this study may induce changes in the dimmer interface, which in turn cause corresponding changes in the active site of the other subunit. Since the active site domains of the two subunits do not participate in the dimmer contacts, conformational changes may be transmitted through domain 4, which is in close contact with the active site domain and forms a large part of the dimer interface. If so, the changes in that domain are too subtle to be discerned by comparing the two structures described in this report. It should be noted that there is some evidence that bound ligands affect the oligomerization state of IDE. The possibility remains open, therefore, that the conformational shifts observed in this study changes the affinity of the dimer interface and affect activity by altering oligomerization. We also note that the absence of the metal ion in the peptide bound mutant enzyme could potentially play a role in altering conformation. However, loss of the metal ion in zinc metallopeptidases has been found to not alter structure, and it seems unlikely that it is influencing the observed differences in conformation.

It has previously been established that polyanions, including ATP, strongly activate IDE toward hydrolysis of small peptides by binding to a site distinct from the active site. The finding that mutations in the distal site greatly reduce or eliminate activation by ATP implies a mechanistic linkage between the two forms of activation. A difference in the bound TNP-ATP emission spectrum caused by mutations in the distal site indicates that changes at that site affect the environment of the ATP binding site. The distal site does not have a concentration of basic residues and therefore seems an unlikely location for ATP binding, suggesting that the effect of mutations there may propagate to another site on the enzyme. One possibility is that the interface between the N- and C-terminal halves of IDE is affected by ATP binding and that mutations at the distal site affect the ability of bound ATP to induce these changes.

Identification of the allosteric site of IDE and possible mechanisms of activation allows those of skill in the art to develop selective activators of IDE or modified versions of the enzyme that may be used as therapeutics for the treatment of Alzheimer's disease and other disorders associated with abnormal levels or activity of IDE.

Throughout this application various publications (including, e.g., patents, patent applications or journal articles) have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

We claim:

1. An isolated mutant insulin degrading enzyme (IDE) comprising at least one amino acid substitution at any of amino acid residues 332, 339, 341, 359, 360, 361, 374, 429, 609, 898, 899 or 901 of SEQ ID NO:1 or SEQ ID NO:2; wherein the isolated mutant IDE has peptidase activity.

2. The isolated mutant IDE of claim 1, wherein the mutant IDE has a substantially similar, increased, or decreased peptidase activity relative to the peptidase activity of a wild-type IDE set forth in SEQ ID NO: 1 or SEQ ID NO:2.

3. The isolated mutant IDE of claim 1, further comprising a chemical modification that increases stability of the mutant IDE.

4. The isolated mutant IDE of claim 3, wherein the chemical modification comprises addition of a component selected from the group consisting of a polymer and a second polypeptide.

5. The isolated mutant IDE of claim 4, wherein the polymer is PEG.

6. An isolated mutant insulin degrading enzyme (IDE) comprising an amino acid sequence that is at least 90% identical to SEQ ID NO:1 over its entire length and comprises at least one amino acid substitution at any of amino acid residues 332, 339, 341, 359, 360, 361, 374, 429, 609, 898, 899 or 901 of the sequence; and wherein the isolated mutant IDE has peptidase activity.

7. The isolated mutant IDE of claim 6, wherein the polypeptide has a substantially similar, increased, or decreased catalytic activity relative to a wild-type IDE of SEQ ID NO:1.

8. The isolated mutant IDE of claim 6, further comprising a chemical modification that increases the stability of the polypeptide.

9. The isolated mutant IDE of claim 8, wherein the chemical modification comprises addition of a component selected from the group consisting of a polymer and a polypeptide.

10. The isolated mutant IDE of claim 9, wherein the polymer is PEG.

11. An isolated polynucleotide comprising a sequence encoding the mutant IDE of any of claims 1 or 6.

12. The isolated polynucleotide of claim 11, wherein the polynucleotide sequence encoding the mutant IDE is operably linked to a promoter.

13. A vector comprising the polynucleotide of claim 11.

14. A recombinant host cell comprising the vector of claim 13.

15. A method of screening agents that modulate the activity of a mutant IDE; said method comprising the steps of (a) contacting a test agent with the mutant IDE in the presence of an IDE substrate, wherein the mutant IDE comprises an amino acid sequence that is at least 90% identical to SEQ ID NO:1 over its entire length and comprises at least one amino acid substitution at any of amino acid residues 332, 339, 341, 359, 360, 361, 374, 429, 609, 898, 899 or 901 of the sequence; (b) assessing the effect of a test agent on activity of the mutant IDE, wherein activity is measured as effect of the test agent on the affinity of the mutant IDE for the IDE substrate or the test agent, rate of the IDE substrate cleavage, or stability of the mutant IDE, relative to a control lacking the test agent; and (c) selecting any test agent that modulates the affinity of the mutant IDE for the IDE substrate or the test agent, the rate of the IDE substrate cleavage, or the stability of the mutant IDE.

16. The method of claim 15, wherein the test agent is selected from the group consisting of a peptidomimetic, analog of a peptide activators, peptide derivative or analog of Aβ, saccharide, fatty acid, purine, pyrimidine, nucleic acid, derivative or analog thereof, complex organic or simple or complex inorganic molecules, metal-containing compounds, steroids, or steroid analog, fluorogenic peptide or derivative or analog thereof, and any such molecules in combination.

17. The method of claim 15, wherein the activity is assessed by measuring the effect of the test agent on the affinity of the mutant IDE for an IDE substrate.

18. The method of claim 17, wherein the substrate is labeled with a detectable label.

19. The method of claim 18, wherein the substrate is monitored via high performance liquid chromatography.

* * * * *